(12) United States Patent
Yoon

(10) Patent No.: US 10,602,915 B2
(45) Date of Patent: Mar. 31, 2020

(54) TRANS-PLATFORM APPARATUS AND USE THEREOF

(71) Applicant: CATHOLIC KWANDONG UNIVERSITY INDUSTRY FOUNDATION, Gangneung-si (KR)

(72) Inventor: Chee Soon Yoon, Incheon (KR)

(73) Assignee: Catholic Kwandong University Industry Foundation, Gangneung-si (KR)

( * ) Notice: Subject to any disclaimer, the term of this patent is extended or adjusted under 35 U.S.C. 154(b) by 862 days.

(21) Appl. No.: 15/112,873

(22) PCT Filed: Jan. 21, 2015

(86) PCT No.: PCT/KR2015/000644
§ 371 (c)(1),
(2) Date: Jul. 20, 2016

(87) PCT Pub. No.: WO2015/111921
PCT Pub. Date: Jul. 30, 2015

(65) Prior Publication Data
US 2016/0331476 A1  Nov. 17, 2016

(30) Foreign Application Priority Data
Jan. 21, 2014 (KR) .................. 10-2014-0007189

(51) Int. Cl.
*A61B 1/00* (2006.01)
*A61B 34/30* (2016.01)
(Continued)

(52) U.S. Cl.
CPC ........ *A61B 1/00101* (2013.01); *A61B 1/0011* (2013.01); *A61B 1/00064* (2013.01);
(Continued)

(58) Field of Classification Search
CPC ........ A61B 1/00101; A61B 17/320016; A61B 1/0008
See application file for complete search history.

(56) References Cited

U.S. PATENT DOCUMENTS

| 5,305,121 A | 4/1994 | Moll |
| 9,655,502 B2 * | 5/2017 | Levy .................. A61B 1/00105 |

(Continued)

FOREIGN PATENT DOCUMENTS

| JP | 2007-007092 A | 1/2007 |
| KR | 10-1070695 B1 | 9/2011 |

(Continued)

OTHER PUBLICATIONS

International Search Report for International Application No. PCT/KR2015/000644, dated Apr. 17, 2015 (5 pages).

(Continued)

*Primary Examiner* — Andrew Yang
(74) *Attorney, Agent, or Firm* — Clark & Elbing LLP; Susan M. Michaud

(57) ABSTRACT

The present invention relates to a trans-platform apparatus including a main platform and an operating device. The trans-platform apparatus of the present invention has the advantage of performing complex and various operations by inserting a maximum number/size of operating devices through a minimal number of openings within an operating space. In addition, since the trans-platform apparatus of the present invention does not use an additional connecting member for a spin shaft, the configuration thereof is further simplified, the operation thereof is easier, and power can be efficiently transmitted to an operating means. The trans-platform apparatus of the present invention is applicable to various fields including medical devices, and an engine room or a device for operating the inside of a radiator.

47 Claims, 40 Drawing Sheets

(51) Int. Cl.
*A61B 46/27* (2016.01)
*A61B 8/12* (2006.01)
*A61B 17/00* (2006.01)

(52) U.S. Cl.
CPC .......... *A61B 8/12* (2013.01); *A61B 17/00234* (2013.01); *A61B 34/30* (2016.02); *A61B 46/27* (2016.02); *A61B 1/00* (2013.01); *A61B 2017/00296* (2013.01); *A61B 2017/00362* (2013.01); *A61B 2017/00473* (2013.01)

(56) References Cited

U.S. PATENT DOCUMENTS

| | | |
|---|---|---|
| 2007/0016119 A1 | 1/2007 | Inada et al. |
| 2007/0049796 A1* | 3/2007 | Fujikura ............ A61B 1/00082 600/116 |
| 2007/0106119 A1 | 5/2007 | Hirata et al. |
| 2013/0006052 A1* | 1/2013 | Song .................... A61B 1/0008 600/109 |
| 2013/0172670 A1 | 7/2013 | Levy et al. |

FOREIGN PATENT DOCUMENTS

| | | |
|---|---|---|
| KR | 10-1150350 B1 | 6/2012 |
| WO | WO-2013/100312 A1 | 7/2013 |

OTHER PUBLICATIONS

Office Action dated Apr. 1, 2019 for Chinese Application No. 20158005273.8, Yoon, "Trans-platform apparatus and use thereof," filed Jan. 21, 2015 (16 pages).

Office Action dated Sep. 24, 2019 for Chinese Application No. 201580005273.8, Yoon, "Trans-platform apparatus and use thereof," filed Jan. 21, 2015 (18 pages).

\* cited by examiner spin shaft hole (a)
spin shaft hole (b)

(a)

(b)

(c)

TRANS-PLATFORM APPARATUS AND USE THEREOF

TECHNICAL FIELD

The present invention relates to a trans-platform apparatus and use thereof.

BACKGROUND ART

Minimally invasive surgery is an advanced concept surgery method which can increase survival rates and the quality of life after surgery by minimizing damage to the body and improving accuracy and safety of the surgery, and various means for such minimally invasive surgery are being developed. The conventional endoscopic surgical apparatus has a problem in that, since surgery is carried out depending on only endoscopic image information, a cut range of a diseased part becomes large in order to safely and precisely perform the surgery, and thus, pain and bleeding are large during the surgery and recovery takes a long time after the surgery. Further, the three-dimensional surgery apparatus (Korean Patent Registration No. 10-2011-0142323) proposed to enable the minimally invasive surgery also has a disadvantage in that since a therapeutic tool should be necessarily inserted into a body through the interior of a main tube, the diameter of the inserted therapeutic tool should be smaller than the diameter of the main tube, and, since the main tube of the three-dimensional surgery apparatus includes an inner tube and an outer tube, the radius of the therapeutic tool which can be mounted therein should be much smaller. Further, the three-dimensional surgery apparatus has a disadvantage in that the therapeutic tool and a spin shaft are connected to each other through a separate connection member, and power is transmitted to the spin shaft through the interior of the connection member, and thus, a power transmission apparatus should be miniaturized.

In recent years, with the increase in concerns for the minimally invasive medical surgery and diagnosis method, the present inventors have developed an apparatus which may include a tool or device (hereinafter, referred to as a "device")—electronic endoscope camera, ultrasonic wave transducer, surgical tool such as robot arm, and the like—for minimally invasive surgery within a human body, the tool or device being inserted into a body of a patient, corresponding to a working space, through a small injection hole, and can perform various functions within such a working space. That is, the present inventors want to develop a trans-platform apparatus which includes an injection hole through which a device used for diagnosis and therapy is injected, and the size of which is as small as possible, and injected devices, the size and the number of which are as large as possible.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have researched and made efforts in order to develop an apparatus which can simultaneously insert one or more working devices into a working space through openings, the number of which is minimal, and reassemble the inserted working devices or change positions of the working devices, thereby performing various and complex roles. As a result, the present inventors have developed a trans-platform apparatus which includes a plurality of working devices longitudinally arranged and mounted at a tip end of a main tube inserted into a working space, and spin shafts coupled to the working devices to enable vertical motions or rotational motions of the working devices, thereby simultaneously performing various functions.

Accordingly, an aspect of the present invention is to provide a trans-platform apparatus (100).

Another aspect of the present invention is to provide a position control apparatus (200).

Another aspect of the present invention is to provide a trans-platform apparatus (300).

Other purposes and advantages of the present disclosure will become clarified by the following detailed description of the invention, claims, and drawings.

Technical Solution

In accordance with an aspect of the present invention, there is provided a trans-platform apparatus (100) comprising:

(a) a cylindrical main platform (110) inserted into a working space; and (b) a cylindrical working device (120) inserted into a tip end or a central portion of the main platform, wherein the working device can be mounted to an outside of the main platform through rotational motion or linear motion.

The present inventors have researched and made efforts in order to develop an apparatus which can simultaneously insert one or more working devices into a working space through openings, the number of which is minimal, and reassemble the inserted working devices or change positions of the working devices, thereby performing various and complex roles. As a result, the present inventors have developed a trans-platform apparatus which includes a plurality of working devices longitudinally arranged and mounted at a tip end of a main tube inserted into a working space, and spin shafts coupled to the working devices to enable vertical motions or rotational motions of the working devices, thereby simultaneously performing various functions.

The three dimensional surgical apparatus (Korean Patent Registration No. 10-2011-0142323) developed by the present inventors, which is an apparatus similar to the trans-platform apparatus according to the present invention, is similar to the present invention in that the former can be mounted to the interior of the endoscope in order to perform various therapies and is used while being radially remounted at the tip end of a main tube. However, the three-dimensional surgical apparatus has disadvantages in that ① since a therapeutic device (tool) of the three-dimensional surgical apparatus should be necessarily inserted into a human body through the interior of the main tube, the diameter of the inserted therapeutic device should be smaller than the diameter of the main tube, and ② since the main tube of the three-dimensional surgical apparatus includes an inner tube and an outer tube, the radius of the therapeutic device which can be mounted to the interior should be much smaller. ③ Further, the three-dimensional surgery apparatus has a disadvantage in that the therapeutic tool and a spin shaft are connected to each other through a separate connection member, and power is transmitted to the spin shaft through the interior of the connection member, and thus, a power transmission apparatus should be miniaturized.

In view of these points, the present inventors have developed a trans-platform apparatus having: ① a working device having a diameter larger than an opening, which can be inserted thereinto; and ② a spin shaft not connected through a separate connection member, thereby making the configuration thereof simpler and the operation thereof more convenient, wherein ③ the trans-platform apparatus can be used in a state in which one or more working devices are inserted at the same time.

The trans-platform apparatus of the present invention is characterized in that working devices, the number and the size of which are maximal, are inserted into a working space through openings, the number of which is minimal, thereby performing complex and various works.

In the present specification, the term "trans-platform apparatus" is a term obtained by abbreviating a function and an advantage of the present invention, which is a coined word created by newly combining the wording "trans" which is a root of the wording "transfer" having the meaning of movement and the wording "transform" having the meaning of transformation with the wording "platform" having the meaning of providing the basis of performance of a function. The present inventors have conceived a trans-platform apparatus 100 and a trans-platform apparatus 300.

Hereinafter, the trans-platform apparatus 100 of the present invention will be described in detail.

1. Main Platform

The trans-platform apparatus of the present invention includes a main platform 110 which is inserted into a working space. The main platform, which has an approximately cylindrical shape, is designed to be inserted into a working space while passing through a narrow opening.

Hereinafter, structural characteristics of the main platform will be described.

A. Cross-section and Recessed Region

The main platform and the working device may be manufactured such that outlines of the cross-sections thereof coincide with each other, but are not limited thereto. The cross-section thereof may have, for example, a circular shape, an elliptical shape, or a polygonal shape. When the cross-section thereof is the polygonal shape, a corner thereof may be a rounded polygon for ease of insertion into the working space.

A plurality of working devices 120 may be mounted to a tip end of the main platform as illustrated in FIGS. 4 to 6. When there are a plurality of working devices, a space should be formed in which spin shafts 130 can rotate, and in order to properly and spatially arrange working devices when the apparatus reaches a final state for an operation as illustrated in FIG. 14, the tip end of the main platform may be manufactured to have not a complete cylindrical shape but a cylindrical shape having concave grooves (or recessed regions) on the side surface thereof. The recessed regions may be manufactured in various shapes according to the sizes of the working devices and the diameters of the spin shafts (see FIG. 12). Meanwhile, recessed regions may be formed on the outer peripheral surfaces of the working devices in order to be mounted to the outer part of the main platform.

According to the present invention, the plurality of working devices are longitudinally connected to the main platform.

B. Electrical Connection Terminal

When the working devices are mounted to the main platform, electrical connection terminals may be formed on the contact surfaces of the main platform and the working devices (see FIG. 33). The electrical connection terminals are formed in the form of a thin membrane, and have a very small volume, and thus, contribute to the miniaturization of the trans-platform device. The transfer of electric energy to each working device may be performed by an electricity transfer apparatus formed in the spin shaft. However, when the electrical connection terminals are used instead of the spin shafts, the shape of the trans-platform apparatus may be further simplified.

C. Spin Shaft Hole

Spin shaft holes 140 having an approximately cylindrical shape may be formed at the tip end or a central portion of the main platform to which the working devices are mounted, such that the spin shafts may be fitted in or screw-coupled to the spin shaft holes 140, and the spin shafts mounted to the working devices are fitted in or screw-coupled to such holes. The sizes and the shapes of the holes formed at the tip end or the central portion of the main platform may be changed according to the lengths and the shapes of the spin shafts.

D. Grooves or Protrusions within Main Platform

Grooves or protrusions installed outside the working devices and grooves or protrusions installed inside the main platform are engaged with each other, thereby enabling stable control of positions of the working devices. When the working devices exist inside the main platform, this configuration serves to fix the working devices such that the working devices do not move within the main platform. It is obvious that when the main platform has a circular shape, the protrusions or grooves serves to control the positions, but when the main platform does not have a circular shape, the structure of the main platform and a portion where the working devices are engaged with each other serve to control the positions.

II. Working Devices

The trans-platform apparatus 100 of the present invention includes working devices 120 having a cylindrical shape, which can be mounted at the tip end or the central portion of the main platform 110. The working devices can be mounted at the outer side of the main platform through the rotational movement or linear movement.

In the present specification, the term "central portion" is used as meaning indicating not only the central portion of the main platform but also portions which are not the tip end or the rear end.

In the present specification, the term "vertical movement" implies the longitudinal axial directional movement of the main platform. Further, in the present specification, the term "forward movement" implies an upward movement on the longitudinal axis of the main platform, and the term "rear movement" implies a downward movement on the longitudinal axis of the main platform.

Each of the working devices includes a body, a moving system (for example, spin shaft) and other components, and a device for a unique function of each working device is installed inside the body. For example, a camera, a light source, an ultrasonic wave probe, a robot arm, a position adjustment device, a surgical device, or a surgical auxiliary device may be installed.

Hereinafter, the structures and the operational characteristics of the working devices will be described.

A. Outer Appearance of and Inserting Method for Working Devices

The outer shapes of the bodies of the working devices are designed as large as possible when the working devices pass through the same opening, and is designed such that the working devices arranged longitudinally are accurately mounted at a mounting part of the main platform.

When the apparatus of the present invention is manufactured such that the cross-section of the main platform and the cross-sections of the working devices coincide with each other, the largest device can be mounted, but the present invention is not limited thereto. The cross-section may be, for example, a circular shape, an elliptical shape, or a polygonal shape.

The one or more working devices are mounted at the tip end of the main platform, and a plurality of working devices may be mounted in a multi-stage as illustrated in FIG. 14. When there are the plurality of working devices, a space should be formed in which the spin shafts can rotate, and in order to properly and spatially arrange the working devices when the apparatus reaches a final state for an operation as illustrated in FIG. 14, the working devices except for the foremost working device may be manufactured to have not a complete cylindrical shape but a cylindrical shape having concave grooves (or recessed regions) on the side surface thereof or may be manufactured in various shapes which form a space for rotation of the spin shafts. The recessed regions may be manufactured in various shapes according to the sizes of the working devices and the diameters of the spin shafts (see FIG. 2).

After being introduced from the outside to the inside of the working spaces, the working devices rotate about the spin shafts coupled to be linked to the working devices, respectively, and thus, are located outside the outer diameter of the main platform. Thereafter, the spin shafts move rearward, and are then inserted into the spin shaft holes, so that the working devices are fixedly mounted at the tip end of the main platform.

When the working devices have various sizes, it is preferred that a working device having the largest diameter among the working devices mounted at the tip end of the main platform is installed on the front side.

The working devices mounted at the tip end of the main platform may not be mounted in a mounting order, that is, may not be mounted while rotating in order according to the numbers thereof, and the sizes of the spin shafts of all the working devices mounted at the tip end of the main platform may be changed according to the uses of the working devices, respectively. For example, as illustrated in FIG. 10, spin shafts of a first working device and a second working device are large, and spin shafts of a third working device to a fifth working device are small. When a rotationally mounted order is an order of the second working device, the third working device, the fourth working device, the fifth working device, and the first working device, the lower plan view of each working device is identical to FIG. 10.

The cross-section of the body of the first working device is identical to the cross-section of the main platform. However, since spin shafts of the first working device to the fourth working device pass through the bodies of the second working device to the fifth working device, respectively, the overall outlines thereof are approximately identical to that of the first working device, but a space (rotation avoiding space) by which the working devices can avoid the spin shafts when rotating should be designed to be an empty space. When a prior working device moves backward and is mounted to the main platform before a working device rotates, the prior working device rotates about the spin shaft by 180 degrees, and is moved backward. At this time, a portion, which protrudes towards the longitudinal sectional surface of the main platform before the prior working device rotates, passes through the working devices, and thus, the portion (rearward space) should be designed as an empty space.

The number of working devices which are mounted to the tip end of the main platform may be changed according to the sizes of the working devices and the use of the trans-platform apparatus.

Meanwhile, the plurality of working devices are longitudinally connected to the main platform and are inserted into the working space.

B. Control of Position of Working Device—Control of Rotational and Linear Movement: Rotation Wedge and Connection Wedge According to the present invention, each of the working devices may additionally include a rotation wedge. In the present specification, the term "rotation wedge" is a rotation control apparatus mounted at an outer lower portion of the working device. In the present invention, the working devices are rotated by about 180 degrees to be mounted to the outer peripheral surface of the main platform. In this case, the rotation wedge comes into contact with the outer peripheral surface of the main platform, and thus, is not rotated by a predetermined angle or more.

FIG. 28 is a schematic plan view illustrating a mechanism for adjusting a rotational angle by a rotation wedge. The rotation wedge may be formed on one side of each of the working devices, which is in contact with the outer peripheral surface of the main platform. The height of the rotation wedge is minimized, so that when the working devices are rotated, other structures are not affected or obstructed. (2) is a view illustrating a state before the rotation, and (3) to (8) are views illustrating changes in positions of the working devices (blue color) when viewed from above. Each of the working devices is rotated about the spin shaft thereof in a clockwise direction.

During the rotation, the rotation wedge of each of the working devices is caught on the outer peripheral surface of the main platform. At this time, the rotation angle of each of the working devices is 180 degrees (8). Thereafter, when the spin shafts continuously perform a screw motion, the rotation motion is blocked by the rotation wedge, and the spin shafts perform only a vertical linear motion. Since the spin shafts are designed to move backward when the working devices are rotated in a clockwise direction, the spin shafts move backward so that the working devices can be mounted on the main platform.

When the spin shafts are rotated in a counterclockwise direction in order to move the working devices to their original positions, the working devices and the outer peripheral surface of the main platform are in close contact with each other, and thus, the rotation motion is blocked, so that the spin shafts perform linear motions. At this time, the rotation direction is a counterclockwise direction, the working devices move forward. When the working devices continuously move forward by the spin shafts, a close contact surface between the main platform and the working devices disappears, and thus, force for blocking the rotation motion disappears, so that the spin shafts perform rotation motions. When the working devices continuously rotate by the spin shafts in a counterclockwise direction, and the rotation wedge comes into contact with a device just below the same or the outer peripheral surface of the main platform, the working devices stop rotating, are at positions just as they pass through the opening, and thus, are at positions where the trans-platform apparatus can be collected.

Thereafter, when it is necessary that the rotation wedge moves forward enough not to be in contact with the main platform, if the connection wedge and the guiding bar are coupled to each other, the screw motion of the spin shafts can be converted into the vertical linear motion.

According to the present invention, each of the working devices may additionally include a connection wedge. In the present specification, the term "connection wedge" is a connection unit formed below each of the working devices or a positioner, or in a recessed region, which serves to connect and couple the guiding bar and the working device to each other.

It is obvious that the position control scheme for the rotation wedge may be applied to spin shafts for applying rotational force to the back side of the main platform as well as spin shafts performing the screw motion.

C. Position Control for Working Devices—Control of Rotational and Linear Motion: Spin Shafts The trans-platform apparatus of the present invention includes the spin shafts 130 which can be inserted into the spin shaft holes 140 formed on the main platform, and operate as linkage axes of the working devices.

The spin shafts, which are connection means for connecting the main platform and the working devices to each other, are inserted into and installed in the inside of the main tube or the inside of the main tube and the insides of the working devices, thereby enabling the vertical motions and the rotation motions of the working devices. The spin shafts may be variously changed and manufactured according to the use of the working devices, a power transmission method for the working devices, an arrangement order of the working devices, and the like. For example, when the working devices operate by rotating the spin shafts outside the opening and moving the spins shafts forward and backward, or electricity or power energy is transmitted through the spin shafts, the spin shafts should be connected up to the rear end of the entire trans-platform apparatus, and thus, should be long. Except for this case, the spin shafts may be configured to be short.

The spin shaft is slantingly formed on one side of the outside of each of the working devices, and is manufactured to be inserted into the spin shaft hole of the main tube (a hole may be installed in the outside and the inside of the main tube or on a tube wall). The spin shaft is designed to minimize a rotation avoiding space and a backward space. Further, the flexibility of each of the spin shafts may be partially differently configured. For example, portions thereof inserted into the main tube are configured by soft portions, and portions thereof coupled to corresponding working devices may be configured by hard portions. Since the spin shafts should be manufactured so as to perform vertical and rotational motions, a portion engaged with a driving nut among the portions thereof inserted into the inside of the main tube is configured to be hard, thereby achieving easy driving.

In order to drive the spin shafts, some hard portions should be included. When the trans-platform apparatus of the present invention is an endoscope apparatus, the trans-platform apparatus should be inserted into a human body, and thus, should be easily bent in the human body. Therefore, it is preferred that the spin shafts minimally include hard portions. In order to minimize the hard portion of the spin shafts, the above-mentioned guiding bar is proposed.

Although the spin shafts may have a smooth cylindrical shape, screw grooves or position fixing protrusion wedges may be formed on the outer peripheral surfaces of the spin shafts according to the use of the working devices and driving devices of the spin shafts, respectively. The position fixing protrusion wedges are used to securely fix the spin shafts at more accurate positions.

The spin shafts may be insert-coupled or screw-coupled to the spin shaft holes, respectively, and when the spin shafts are screw-coupled to the spin shaft holes, respectively, screw threads are formed on the spin shafts and in the spin shaft holes.

Electric power transmission apparatuses or power transmission apparatuses may be additionally included in the spin shafts in order to transfer power or electric power for driving the working devices, respectively.

Further, fluid transfer tubes for removing foreign substances or product materials generated in the working space may be formed in the spin shafts, respectively. Such fluid transfer tubes discharge materials to be removed from the working space, to the outsides of the working devices, by spraying fluid.

Further, when the working devices are mounted not in the inside of the main platform but at the tip end of the main platform as in the present invention, a rotary shaft (spin shaft) is installed more advantageously than the conventional three-dimensional endoscopic surgical apparatus (Korean Patent Registration No. 10-2011-0142323). When the working devices are included in the trans-platform apparatus, the spin shafts and the working devices are connected to each other through separate connection parts, respectively. In order to transfer power through these small connection parts, rotary shafts, which are equally as precise, are required. Meanwhile, when the working devices are mounted at the tip end of the main platform, the rotary shafts (spin shafts) are formed on sides of the working devices, respectively, so as to directly transfer power. Thus, a relatively large and stable power transmission apparatus can be used to rotate the spin shafts.

D. Positions Conversion for Working Devices: Moving System

In the present invention, the working devices are required to be subjected to position conversion in order to be mounted to the main platform. The position conversion method includes, for example, (i) a method for converting positions by moving the spin shafts forward and rearward by rotating the spin shafts at the rear side of the main platform, and (ii) a method for converting positions at the tip end or the central portion of the main platform. The reason why the position conversion is performed at the tip end of the main platform is that when the main platform or the spin shafts are made of flexible materials, if the positions of the working devices are controlled by the movement of the spin shafts, it is difficult to perform the position control due to the torque absorption phenomenon. In order to perform the position conversion at the tip end or the central portion of the main platform, the positions should be converted in a state in which the working devices have moving systems, respectively, or the positions should be converted by separate transfer systems of the working devices (hereinafter, a device, the position of which is converted in a state in which the device has a moving system, is referred to as an "active device", and a device, the position of which is converted by another transfer system, is referred to as a "passive device").

A driving device for driving the active (working) device may be installed on the main platform or may be installed in a body of the working device.

Hereinafter, the moving system of the working device will be described in detail.

1) Configuration of Moving System

Basically, the moving system of the working device performs the linear vertical motion and the rotation motion. A means therefor may include a motor performing a linear motion, and a combination of various motors or various position control apparatuses, that is, the moving system, which performs a rotational motion.

According to the present invention, the moving system may be selected from the group consisting of (i) the spin shafts 130 which are formed on the main platform or sides of the working devices, adjust the rotational and vertical motions of the working devices, and operate as linkage axes of the working devices, (ii) capturers which are formed on the main platform or sides of the working devices, and can be coupled to the working devices, and (iii) linear motion units, linear motion guiding units, or a combination thereof which are formed on the main platform or sides of the working devices, and adjust the working devices or a linear motion in the horizontal axis direction (direction vertical to central axis of main platform).

According to the present invention, the linear motion unit is a horizontal shaft (shaft installed in horizontal direction), and the linear motion guiding unit is a horizontal directional sliding channel. The sliding channel may be formed on the upper surface or the lower surface of a working device in contact with the main platform.

The spin shafts may be insert-coupled or screw-coupled to the main platform, and the spin shafts are inserted and installed inside the main platform or inside the main platform and inside the working devices, thereby enabling the vertical motion and the rotation motion of the devices.

Each of the spin shafts may include a soft portion and a hard portion, and may additionally include an electric signal transmission apparatus, an electric power transmission apparatus, a fluid transmission tube, and a power transmission apparatus. In the trans-platform apparatus of the present invention, a space in which the spin shafts can rotate, and the spin shaft holes may be formed outside the main platform.

The capturers, which may be formed on the working devices in order to perform position control of the working devices or may be coupled to the working devices, respectively, may be insert-coupled, screw-coupled, ratchet-coupled, rack-pinion-coupled or magnetic-coupled to the working devices, respectively. Basically, the capturers operate in the same principle as that of a capturer included in a positioner described below.

The sliding channels, which are formed on contact surfaces of the main platform and the working devices, enable the linear motions of the working devices, respectively.

According to the present invention, the moving system may additionally include a configuration selected from the group consisting of (a) a driving or fixing nut, (b) a guiding tube which has a cylindrical tube, and controls the linear and rotational motion of the spin shafts, (c) a guiding bar including an upper cylinder, a lower cylinder, and a body for connecting the upper cylinder and the lower cylinder to each other, the guiding bar being mounted to a recessed region formed on the outer peripheral surface of the main platform and guiding the linear motions of the working devices, (d) a spin shaft, and (e) a combination thereof.

For example, when a motor for driving the driving nut is mounted to the main platform, male screws are installed in the spin shafts connected to the bodies of the working devices, respectively, and a rotational nut engaged with the male screws is installed in the main platform (see FIG. 18), the spin shafts perform the screw motions by the rotation of the driving nut. ① A guiding tube for converting these screw motions into a linear motion and a rotational motion is mounted to the main platform (FIG. 20), ② the rotation wedges are mounted to the bodies of the working devices, respectively, or ③ the working devices may be mounted on the outer peripheral surface or the inner peripheral surface (hereinafter, mounting part) of the main platform, using the guiding bar.

According to the present invention, the nut is a driving nut or fixing nut. The driving nut has a female screw installed therein so as to be engaged with a male screw installed on the outer peripheral surface of each of the spin shafts. Further, gears are installed outside the spin shafts, respectively, and transfer rotational force of a driving motor to the spin shafts, thereby performing the screw motions. The driving nut may be designed to enable the rotational motion but disable the linear motion. The gear may be installed outside the driving nut as illustrated in (4) of FIG. 18. In this case, the driving nut is driven by the driving force transferred from the gear. The fixing nut serves as a simple nut in the screw motion of each of the spin shafts which perform the rotational motions.

According to the present invention, the spin shafts as configurations of the moving systems of the working devices have male screw grooves for the screw motions, respectively, and can perform the screw motions by direct connection to the gears of the driving motor or driving of the nuts themselves.

As needed, a guiding boss, a power transmission gear, a spin shaft tip, and the like may be formed at the end of the spin shaft, respectively.

In the present specification, the term "guiding boss" is a rod formed at the end of a spin shaft and has an approximately cylindrical shape, and the guiding boss may perform a linear motion or a rotational motion along a guiding groove, which is a guiding groove of the guiding tube (see FIG. 19 and FIG. 20). Spherical catching steps for preventing the guiding bosses from being moved within the guiding tubes may be formed at ends of the guiding bosses, respectively (see FIG. 20).

In the present specification, the term "spin shaft tip", which is an approximately cylindrical fixing unit, is formed at an end of a spin shaft, is inserted into a groove of a lower cylinder of a guiding bar, and fixes the spin shaft and the guiding bar while not disturbing the rotational motion of the spin shaft, thereby serving to move the guiding bar together when the spin shaft moves forward and rearward.

In the present specification, the term "guiding tube" has an approximately cylindrical shape having a guiding groove formed therein, a spin shaft is located within the tube, and the guiding boss and the guiding groove of the spin shaft are engaged with each other, thereby controlling the linear motion and the rotation motion of the spin shaft (see FIG. 20). The guiding tube is used together with the rotatable driving nut. The guiding groove, which is a space where the guiding boss can move, is formed on the outer peripheral surface of the guiding tube, and such a guiding groove may be designed variously according to the motional direction of the spin shaft.

In the present specification, the term "guiding bar" is a configuration mounted in a recessed region formed on the outer peripheral surface of the main platform, and serves to guide the linear motion of a corresponding working device (see FIG. 21). The guiding bar is used while being mounted to the recessed region formed on the main platform, and thus, is designed in accordance with the shape of the recessed region. Thus, the guiding bar has not a complete cylindrical shape but an approximately cylindrical shape having an elliptical bottom surface, both ends of which are sharp, as illustrated in FIG. 21.

According to the present invention, the guiding bar includes an upper cylinder, a lower cylinder, and a body for connecting the upper cylinder and the lower cylinder. The upper cylinder and the lower cylinder are mounted to both ends of the body. A hole through which each of the spin shafts can pass is formed in the upper cylinder, and a groove to which the connection wedge is coupled is formed on the upper surface of the upper cylinder. A groove into which the spin shaft can be inserted is formed on the upper surface of the lower cylinder, and a space where the spin shaft tip can be located is formed below the hole. The spin shaft tip is coupled to the groove of the lower cylinder so as to perform the vertical motion together. Even when the spin shaft is coupled to the guiding bar, the rotational motion is not disturbed. The spin shaft is designed to perform the rotational motion inside the lower cylinder.

The body of the guiding bar may be generally designed to be an approximately cylindrical shape, or may be designed to be a minimum of two columns for connecting the upper and lower cylinders. For example, in FIG. 21, the guiding bar includes upper and lower cylinders and two columns for connecting the upper and lower cylinders to each other.

FIG. 23 is a schematic view illustrating a configuration in which a spin shaft, a connection wedge, and a rotation wedge are formed in a working device. The connection wedge serves to connect and couple the guiding bar and the working device. In order to transfer power to the spin shaft, a motor or a gear may be additionally mounted. These elements transfer rotational force to the spin shaft or the driving nut coupled to the spin shaft. The recessed region, which is a space where the guiding bar and the working device are engaged with each other, has a connection wedge for mechanically connecting the guiding bar and the working device to each other. The spin shaft tip is coupled to the lower cylinder of the guiding bar.

(1) of FIG. 24 illustrates the shape of the main platform when a space through which the guiding bar and the spin shaft pass is formed (see (1) of FIG. 24). (2) of FIG. 24 illustrates the inside of the main platform when a nut in addition to the guiding bar is formed additionally. A nut having a female screw formed therein to be engaged with the spin shaft is formed in a recessed region of the main platform.

2) Example of Formation of Moving System

Meanwhile, the moving system of the working device may be formed on the main platform, the working device, or the main platform and the working device. FIG. 20 illustrates a case where the moving system is formed on the main platform. The working device is driven by operations of the spin shaft and the nut performing the screw motion, the motor, the gear, and the guiding tube. The working device is coupled to the upper portion of the spin shaft, and the driving nut, the motor, and the guiding tube are located inside the main platform. The screw motion of the spin shaft is generated by rotating the driving nut, and the rotational motion and the vertical linear motion of the spin shaft are determined by the guiding tube.

FIGS. 25 to 26 illustrate cases where the moving system is complexly formed on the main platform and the working device. The fixing nut is formed on the recessed region of the main platform, and a space into which the guiding bar and the spin shaft are inserted is formed on the recessed region of the main platform. The rotation wedge and the connection wedge are formed in the working device, and the spin shaft tip is formed at an end of the spin shaft coupled to the working device.

FIG. 27 schematically illustrates driving of the working device when the moving system of the working device is complexly formed on the main platform and in the working device in FIG. 26. (A-1) to (A-2) are views illustrating a state in which the spin shaft transfers the working device while moving vertically, and illustrating a state in which the working device, the spin shaft, the guiding bar, and the connection wedge move while being coupled to each other. The guiding bar linearly moves while disturbing the rotational force of the spin shaft, and the connection wedge serves to mechanically couple the guiding bar and the working device so as not to rotate the working device arbitrarily. Accordingly, the working device may move the vertical linear motion without the rotational motion. (A-3) illustrates a state in which the connection wedge is separated from the guiding bar in order to mount the working device to the outer peripheral surface of the main platform. Accordingly, the spin shaft can perform the rotational motion. (A-4) illustrates a state in which when the working device is rotated by 180 degrees, the rotation wedge comes into contact with on the outer peripheral surface of the main platform, so that the working device stops rotation. The screw motion of the spin shaft is converted into the linear motion again, so that the working device can move a downward direction of the main platform. When the working device moves backward, and reaches a position of (A-5), the working device is completely mounted to the outer peripheral surface of the main platform. Thereafter, when the working device is retrieved, (A-1) to (A-5) are performed reversely.

E. Position Conversion of Working Device: Transfer System

In order to perform position conversion at the tip end or the central portion of the main platform, a separate transfer system of the working device may be included.

According to the present invention, the trans-platform apparatus of the present invention may additionally include a positioner 140 for controlling a position of the working device (see FIG. 29). The working device mounted to the main platform moves actively or manually. A case where the working device is driven by an electrical signal while including the moving system formed in the trans-platform apparatus in order to move the working device corresponds to an active motion, and a case where a position is converted by a different separate transfer system, for example, a positioner without a motion control device corresponds to a passive motion. In this case, the working device is a device, the position of which is converted by the separate different transfer system, and corresponds to a passive device.

In the present specification, the term "positioner" implies a device which is a transfer system, is used as the same meaning of the position control apparatus 200 for controlling positions of the working devices longitudinally connected to each other, and mounts the working device not including the moving system to the main platform. The positioner serves to mount the working devices to the main platform through the vertical reciprocating motion, the horizontal reciprocating motion, and the rotational motion, and may be installed in the tip end, the central portion or the inside of the main platform. In general, the positioner is advantageously installed at the tip end of the main platform, but may be installed at various positions as needed. The positioner may include a separate working device therein, thereby performing an independent different function (for example, light source unit, camera unit, treatment unit, and the like) in addition to a function of mounting the working devices to the main platform. The positioner may include a camera, a light source, an ultrasonic wave probe, a robot arm, a surgical device, or a surgical auxiliary device, as the working device.

In order to mount the working device having the spin shaft to the tip end of the main platform, the working device rotates about the spin shaft so as to move to the outside of the main platform, and then moves backward so as to be mounted to the mounting part of the main platform. When the main platform or the spin shaft is made of a flexible material, if the spin shaft is rotated by applying rotational force from the rear side of the main platform, a torque absorption phenomenon occurs in the spin shaft, and thus, it is difficult to control positions of the working devices. In order to prevent this state, the positioner is designed in order to directly rotate the working device without rotating the spin shaft. Further, the positioner is designed to complement a disadvantage that the size of the working device is increased when the moving system is installed in each working device. The positioner is installed at the tip end or the central portion of the main platform or inside the main platform, so that the positions of the working devices can be controlled.

Hereinafter, the positioner will be described in detail.

1) Configuration of Positioner

The positioner of the present invention includes a cylindrical body 210 which can be mounted at the tip end of the main platform or at the upper portion or lower portion of the working devices longitudinally connected to each other inside the main platform, and transfer units formed in the body 210 to be coupled to the working devices so as to move the working devices. Further, the positioner may additionally include the spin shaft (hereinafter, referred to as a P spin shaft), the connection wedge, or the rotation wedge which is for driving the positioner, in addition to the body and the transfer unit.

According to the present invention, the transfer unit for transferring the passive device may be selected from the group consisting of (a) capturers 220 for connecting the working devices and the transfer units to each other, (b) a rotary shaft for rotating the capturer, (c) a driving shaft for vertical motion of the capturer, (d) a driving or fixing nut, (e) a guiding tube which is as a cylindrical tube and controls linear and rotational motion of a T-spin shaft, (f) a guiding bar which includes an upper cylinder, a lower cylinder and a body for connecting the upper cylinder and the lower cylinder, is mounted inside of the body of the positioner, and guides linear motion of the working device, (e) a T-spin shaft 250 capable of rotational and vertical reciprocating motion, and (g) a combination thereof. Further, one or more transfer units may be installed.

The capturer may be coupled to the rotary shaft, the driving shaft for vertical motion, or the T spin shaft, and one component thereof is selected according to a functionally required motion. For example, when only the rotational motion is required, the rotary shaft is coupled to the capturer, when only the vertical reciprocating motion is required, the driving shaft for the vertical motion is coupled to the capturer, and when the rotational motion, the vertical reciprocating motion, or the two motions are required, the T spin shaft is coupled to the capturer.

For example, the transfer unit may include the guiding tube having a guiding groove installed therein, the spin shaft (T spin shaft) which has the guiding boss installed therein and is for transferring the passive device, the driving nut, and the capturer (FIG. 34). The T spin shaft, the guiding tube, and the rotational (driving) nut are configured in one set, and these components are located inside the positioner (but, the capturer may be located outside or inside the positioner). In operation, the T spin shaft is moved so that the capturers and the working devices are coupled to each other, and the T spin shaft having the guiding boss is located inside the guiding tube, and is connected to the driving nut. Thus, the driving nut is rotated, the T spin shaft performs the rotational motion and the vertical motion along the groove installed in the guiding tube, and accordingly, the positions of the capturers and the working devices connected to the T spin shaft are controlled (See FIG. 34).

FIG. 29 is a perspective view illustrating a positioner before the operation. The guiding tube, the T spin shaft, and the driving nut inside the transfer unit are located inside the body of the positioner, and thus, are not viewed in the drawing, but the capturer is located outside the body of the positioner, and thus, is viewed (see FIG. 35, FIG. 36 and FIG. 38).

The capturer may generally have a cylindrical shape, but may be changed in various shapes in order to maximize a capturing function. Thus, the capturers may be coupled to the working devices in various schemes, respectively. For example, the capturer may be a link type, a crank type, or a ratchet type which are movable. More specifically, there are: a case where a groove 240, which can be coupled to a coupling protrusion of the working device, is formed inside the capturer, and the coupling protrusion is simply inserted into and coupled to the groove; a case where the coupling protrusion and the capturer are coupled to each other in a ratchet scheme; a case where the coupling protrusion and the capturer are coupled to each other in a rack-and-pinion scheme; a case where the coupling protrusion and the capturer are screw-coupled to each other; and a case where the coupling protrusion and the capturer are magnetically-coupled to each other. Further, the capturer may include a crank which can perform the reciprocating motion or the rotational motion.

The capturers may be coupled to the working devices by horizontally or vertically moving the transfer units, respectively, or may be coupled to the working devices by using a plurality of transfer units fixed to the body of the positioner, respectively.

According to the present invention, for the position control of the transfer unit, the positioner may additionally include a linear motion unit (for example, horizontal shaft 260 (shaft installed in horizontal axis direction)) or a linear motion guiding unit (for example, sliding channel) which enables the transfer unit to perform a linear motion in the horizontal axial direction (vertical direction of central axis of main platform) of the main platform (see FIGS. 37 and 38). Further, the positioner may additionally include a rotary shaft which is formed in the body of the position control apparatus, and is coupled to the linear motion unit or the linear motion guiding unit or is coupled to the transfer unit.

The gear is installed in the rotary shaft, and thus rotation is possible. Further, a rotary gear can be driven while being connected to a gear of a step motor, the angle of which can be adjusted. In FIG. 36, the rotary shaft and the driving device are omitted. When the rotary shaft rotates, the transfer unit connected and coupled to the rotary shaft moves along an arc, the center of which is the rotary shaft. By such motion, the position of the transfer unit is converted, and thus, the working devices at various positions are transferred by one transfer unit so as to be mounted to the main platform. In FIG. 37, the rotary shaft having the horizontal shaft installed therein and the driving device are omitted. A transfer nut is engaged with the horizontal shaft and moves linearly according to the rotation of the horizontal shaft, and a connection member connects and couples the transfer nut and the transfer unit to each other.

The connection wedge serves to connect and couple the guiding bar and the positioner. Meanwhile, in order to transfer power to the spin shaft (P spin shaft and T spin shaft), a motor or a gear may be additionally mounted, and these components transfer rotational force to the spin shaft or the driving nut coupled to the spin shaft.

The rotation wedge is a rotation control apparatus mounted to an outer lower portion of the positioner. In the present invention, the positioner is rotated by about 180 degrees so as to be mounted to the outer peripheral surface of the main platform. In this case, the rotation wedge comes into contact with the outer peripheral surface the main platform, and thus, is not rotated by a predetermined angle or more.

According to the present invention, for the position conversion of the body, the positioner may additionally include a moving system configured by (a) a driving or fixing nut, (b) a guiding tube which is a cylindrical tube and controls the linear motion and the rotational motion of the P-spin shaft, (c) a guiding bar which includes an upper cylinder, a lower cylinder and a body for connecting the upper cylinder and the lower cylinder to each other, is mounted on a recessed region formed on the outer peripheral surface of the main platform, and guides the linear motion of the working devices, (d) a P spin shaft 230 which is mounted in the body 210, adjusts the rotational motion and the vertical motion of the body, and operates as an linkage axis of the body, and (e) a combination thereof. The moving system is a device for controlling a position of the body of the positioner, and the above-described transfer unit is a device for controlling positions of the passive working devices. The two devices are mounted in the positioner, and the positions of the passive working devices can be adjusted using the two devices together or individually using the two devices.

According to the present invention, a driving device for driving the moving system and the transfer unit is additionally installed in the body of the positioner, and the driving device includes a rotary shaft gear motor, and the like. FIG. 31 is a schematic plan view illustrating positions of gears when a motor or a gear is additionally mounted in order to transfer power to the spin shaft, wherein these components transfer driving force to the spin shaft or the driving nut coupled to the spin shaft. A Connecting Gear (CG) moves along a blue curved line, and is engaged with the driving gear (PG, N-T1 or N-T2; PG; gear, N-T1, and N-T2 of moving system of positioner; and gear formed in driving nut of moving system for position control of each working device) so as to move a desired apparatus. The driving force can be transferred to the working devices, the positioner, or the spin shafts by using motors, the number of which is minimal, without mounting the respective working devices to the motor, by combining various gears.

2) Operation of Positioner (i) Operation of Capturer

FIG. 30 schematically illustrates an operation sequence of a positioner including the transfer unit (capturer and T spin shaft), and the positioner operates in the following sequence.

(1) This view illustrates a state before being firstly mounted to the side surface of the main platform, and the coupling protrusion (purple color) of the working device is inserted into the capturer. This operation can be performed by backwardly moving (downwardly moving) the P shaft or the T shaft or by forwardly moving (upwardly moving) the working device.

(2) The protrusion of the working device pushes a wedge within the capturer, and a spring coupled to a capturer arm is contracted by an elastic operation, so that the coupling boss of the working device and the capturer of the positioner are coupled to each other. In such a state, the working device is rotated by driving the T spin shaft, and after the rotation, the working device moves to the mounting part of the main platform by backwardly moving the P spin shaft or the T spin shaft.

(3) While the working device reaches the mounting part of the main platform, and thus, the device is mounted to the main platform, a protrusion formed in the mounting part of the main platform is inserted into the capturer arm, and accordingly, the capturer and the coupling protrusion of the working device are uncoupled from each other.

(4) In a state in which the protrusion of the mounting part is inserted into the capturer arm, as the P spin shaft or the T spin shaft moves upwardly, the coupling protrusion of the working device is separated from the capturer, and the wedge within the capturer is inserted into the capturer arm, so that the capturer arm is maintained in an opened state.

(5) In this state, the P shaft or the T shaft moves forwardly, and the T shaft rotates so that returns to an initially setting state.

Thereafter, a capturer of another transfer unit mounts another working device to the main platform through the processes (1)-(4). Thereafter, even when the working device located in the mounting part of the main platform is retrieved again, the processes (1)-(4) are repeatedly performed.

(ii) Transfer of Working Device Having Spin Shaft by Using Positioner Located at Tip End In order to change a position of the working device having the spin shaft, rotation using the spin shaft as a central axis and vertical motion using the spin shaft as a guiding means are used. The working device is coupled by backwardly moving the transfer unit installed in the position control apparatus, moves to a position where the mounting part of the working device can be mounted to the mounting part of the main platform, by rotating the transfer unit, and is then mounted to the main platform by backwardly moving the transfer unit. In order to perform the rotation of the transfer unit while using the spin shaft of the working device as a center, the central axis of the transfer unit and the rotary shaft of the working device coincide with each other. Otherwise, the transfer unit may rotate about the spin shaft of the working device by using the crank-type capturer. An angle of the rotation may be adjusted using the T spin shaft and the guiding tube.

The backward motion for mounting the working device to the main platform may be achieved by backwardly moving the transfer unit or the body of the position control apparatus. Thereafter, a process of retrieving the mounted working device from the main platform is performed in an inverse order of the mounting process (see FIGS. 15 to 27).

(iii) Transfer of Working Device not Having Spin Shaft within Main Platform by Using Positioner Located at Tip End.

In order to mount the working device to the outer peripheral surface of the main platform by transferring the working device located within the main platform, the driving device of the transfer unit of the present invention performs the following motion.

The capturer and the working device are coupled to each other by backwardly moving the transfer unit in a longitudinal direction, and the working device moves to the outside (outside of longitudinal section of main platform) of the main platform by forwardly moving the body of the positioner. Thereafter, the transfer unit forwardly moves to the horizontal axis of the main platform (vertical direction of central axis of main platform) to move to the outside (outside of cross-section) of the main platform, moves to a position where the working device can be mounted to the outer peripheral surface of the main platform, and is then rotated by a predetermined angle using the central axis of the main platform as a rotary shaft. Thereafter, the working device is mounted to the main platform by backwardly moving the positioner or the transfer unit. When there are a plurality of working devices, there are a plurality of predetermined angles.

Meanwhile, the mounting part of the working device mounted to the main platform has a recessed shape, and the recessed portion is located in the P spin shaft or the guiding bar of the positioner. That is, the working devices located in the main platform are configured to have the same cross-section, and are longitudinally located in the main platform such that the cross-sections thereof coincide with each other. Accordingly, the sizes of the working devices mounted inside the main platform may be maximal.

The respective working devices sequentially move forward or horizontally by the positioner, are rotated by the predetermined angles of the respective working devices, and move backward, and are mounted to other positions of the main platform.

The transfer unit is coupled to and installed in the transfer nut coupled to a screw groove, and moves according to the motion of the nut. The transfer nut and the transfer unit are coupled to each other by the connection member, the connection member is designed to be longer than the length of the nut, and the nut is fixedly coupled to an end of the connection member. The transfer unit is fixedly coupled to the opposite surface of the other end of the connection member.

The transfer nut moves along a shaft (hereinafter, referred to as a "horizontal shaft") horizontally installed in the body of the positioner, and a screw is installed in the horizontal shaft. A driving gear is installed at an end of the horizontal shaft, and thus, can be rotated, and a transfer nut moves by rotating the horizontal shaft. When the transfer nut reaches an edge of the positioner, the transfer unit moves outside the body of the positioner due to an interval between the transfer nut and the transfer unit, so that the working device coupled to the transfer unit is at a position to be mounted to the main platform (see FIGS. 37, 38 and 39).

An end of the horizontal shaft is connected and coupled to the rotary shaft which rotates about a central axis of the main platform, and this rotary shaft has a gear additionally installed therein, and thus, may be installed rotatably by the driving device. The rotary shaft is coupled to the body of the positioner.

The step motor, the angle of which can be adjusted, is used as a motor for driving the rotary shaft.

(iv) Transfer of Working Device not Having Spin Shaft within Main Platform by Using Positioner Located Inside the Main Platform The positioner, which has a cylindrical shape, has a structure in which a groove engaged with a protrusion within the main platform is formed so that the vertical motion can be performed while the position is fixed. Thus, the main platform can be received in the positioner. The positioner is located below the working device.

The transfer unit, in which the capturer is installed, is installed to be shifted to one side of the inside of the positioner, and can perform the vertical motion and the rotation. The transfer unit is coupled to a rotary shaft which rotates about the central axis of the main platform (see FIG. 40). The rotation of the rotary shaft is driven by the step motor, the rotation angle of which can be adjusted.

The transfer unit moves to an empty space formed by the recessed region of the working device, is coupled to the working device at the upper end or on the side surface of the working device, moves forwardly (toward the central axis of the main platform) to move the working device to the outside of the main platform, is rotated about the central axis of the transfer unit by 180 degrees, is rotated about the central axis of the main platform by a predetermined angle, moves backwards, and is then mounted to the main platform. Meanwhile, the rotation about the central axis of the transfer unit and the rotation about the central axis of the main platform may be performed in a reverse order.

III. Other Configurations

The trans-platform apparatus of the present invention may additionally include a cover for covering the tip end of the main platform or the working device. The cover may be manufactured in an approximately cylindrical shape which is similar to the shape of the tip end of the main platform or the working device, but is not limited thereto. When passing through the opening and reaching the working space, the cover moves backward so as to be mounted to a hole formed in the tip end of the main platform. Further, the cover is configured such that the size thereof is increased, and thus, can function to protect a space in which the working devices are mounted, from an external tissue.

The trans-platform apparatus of the present invention may additionally include a driving device which is mounted inside the working device or the main platform and enables the operation of the working device. The driving device is provided so that the speed and the direction at which the working device is inserted into the working space can be precisely adjusted. For example, the apparatus of the present invention is used as an endoscope apparatus, and the driving device is provided so as to precisely and automatically control an endoscopic surgical tool which is inserted into a human body, and precisely adjust the speed and the direction of a surgical device which is inserted into the human body, thereby minimizing injury of the human body. A motor or a gear may be employed as the driving device.

FIG. 31 is a schematic plan view illustrating positions of gears when a motor or a gear is additionally mounted in order to transfer power to the spin shaft, wherein these components transfer driving force to the spin shaft or the driving nut coupled to the spin shaft. The CG moves along a blue curved line, and is engaged with the driving gear (PG, N-T1 or N-T2; PG; gear, N-T1, and N-T2 of moving system of positioner; and gear formed in driving nut of moving system for position control of each working device) so as to move a desired apparatus. The driving force can be transferred to the working devices, the positioner, or the spin shafts by using motors, the number of which is minimal, without mounting the respective working devices to the motor, by combining various gears.

The trans-platform apparatus of the present invention may additionally include a working device which is located inside the main platform, and is later mounted to the outer peripheral surface of the main platform. As illustrated in FIG. 14, a working device (yellow color) which is coupled to the tip end of the main platform and is later mounted to the outer peripheral surface of the main platform and a working device which (green color) is located inside the main platform and is then mounted to the outer peripheral surface of the main platform may be used together. The yellow and green working devices are driven individually or are driven while being mechanically coupled to each other. When being driven while being mechanically coupled to each other, the working devices can perform more complex and various functions.

The working devices, which are mounted inside the main platform and move to the working space, are connected to the spin shafts by separate connection members, respectively, and the connection members are coupled through separate spin shaft fixing holes 150 formed in the main platform and inner and outer channels, respectively, so that the working devices may be mounted to the main platform (see FIG. 13).

The trans-platform apparatus of the present invention may be applied to all cases where the working devices should be inserted into the working space through a narrow opening, and may be applied to, for example, an endoscopic apparatus or an endoscopic apparatus including a surgical tool. When the trans-platform apparatus of the present invention is the endoscopic apparatus, the trans-platform apparatus of the present invention may include a camera, a light source, or the camera and the light source as the working devices. One or a plurality of cameras may be configured, and each camera includes a lens, an image sensor, and a lens driving apparatus. The image sensor serves to convert an image signal photographed by the lens into an electrical digital image signal, and the lens driving apparatus serves to drive the lens in order to perform a zoom function and a focus function of the camera. Meanwhile, the light source serves to provide lighting for enabling the inside of the working space to be photographed. The light source includes an LED and a reflector, and receives power through a power transmission apparatus within the spin shaft so as to emit light. The reflector serves to reflect light emitted by the LED to the front side, and may be concavely installed in order to maximize a front lighting effect.

When the trans-platform apparatus of the present invention is the endoscopic apparatus, the trans-platform apparatus may additionally include a surgical device or a surgical auxiliary apparatus as a working device.

The biggest feature of the present invention is that the working devices, the size and the number of which are as large as possible, are used while being inserted into a closed (or isolated) working space through openings or input ports, the number of which is minimal. For example, when a medical treatment tool is mounted to the apparatus of the present invention, and is then inserted into the body of a patient, a surgical tool, a surgical auxiliary tool, a camera, and the like can be inserted by minimal cutting at the same time. Particularly, two or more cameras can be inserted, thereby obtaining a three-dimensional stereoscopic image. Unlike the conventional technology, a therapeutic tool is not mounted to the endoscopic tube inserted into the body of a patient, but the therapeutic tool is coupled to the tip end of the tube, so that the therapeutic tool having a larger diameter can be inserted into the body. That is, when the apparatus of the present invention is used, the therapeutic tool having a diameter larger than the thickness of the conventional therapeutic tool by the thickness of the outer wall of the endoscopic tube can be inserted into the body of the patient.

In accordance with other aspect of the present invention, there is provided a position control apparatus (200) for controlling positions of working devices longitudinally connected to each other at a tip end of or inside a main platform, the position control apparatus comprising:

(a) a cylindrical body (210) that is mounted to an upper portion or a lower portion of one of the working devices longitudinally connected to each other; and (b) a transfer unit that is formed inside the body, is coupled to the working devices, and moves positions of the working devices.

The position control apparatus of the present invention uses a configuration and a driving principle of the above-described positioner, and common contents therebetween will be omitted in order to avoid making the present specification excessively complex.

The position control apparatus of the present invention is designed to control positions of working devices longitudinally connected to each other, and a body 210 of the position control apparatus may be mounted to the upper portion or the lower portion of the working devices longitudinally connected to each other. It is described that the body has a cylindrical shape, but the body may be changed in various well-known shapes.

The transfer unit may be selected from the group consisting of (a) a capturer 220 for connecting the working device and the transfer unit to each other, (b) a rotary shaft for rotating the capturer, (c) a driving shaft for vertical motion of the capturer, (d) a driving or fixing nut, (e) a guiding tube which is as a cylindrical tube and controls linear and rotational motion of a T-spin shaft, (f) a guiding bar which includes an upper cylinder, a lower cylinder and a body for connecting the upper cylinder and the lower cylinder, is mounted inside of the body of the positioner, and guides linear motion of the working device, (e) a T-spin shaft 250 capable of rotational and vertical reciprocal motion, and (g) a combination thereof. Further, one or more transfer units may be installed.

The position control apparatus of the present invention includes the capturer 220 connected to the T spin shaft coupled to the body 210. The capturer may be coupled to the working device in various schemes, and the capturer may be a link type, a crank type, or a ratchet type which are movable. More specifically, there are a case where a groove 240, which can be coupled to a coupling protrusion of the working device, is formed inside the capturer, and the coupling protrusion is simply inserted into and coupled to the groove; a case where the coupling protrusion and the capturer are coupled to each other in a ratchet scheme; a case where the coupling protrusion and the capturer are coupled to each other in a rack-and-pinion scheme; a case where the coupling protrusion and the capturer are screw-coupled to each other; and a case where the coupling protrusion and the capturer are magnetically-coupled to each other.

The T spin shaft operates as a linkage axis of the working device, and can perform rotational motion and vertical motion. For example, the T spin shaft is mounted inside the body 201, and moves together with the capturer to the outside of the body so as to adjust a position of the working devices, and can operate as a linkage axis of the working device.

The position control apparatus of the present invention may include one or more transfer units, and the transfer units may be formed to be shifted to one side of the body. The position control apparatus of the present invention may be used to control positions of working devices longitudinally connected to each other, such as a camera, a light source, an ultrasonic wave probe, a robot arm, a position adjustment device, a surgical device, and a surgical auxiliary device.

The spin shaft (see (1) of FIG. 29) coupled to the outside of the body 201 of the position control apparatus or the spin shaft coupled to the inside of the body 201 may be configured by a soft portion, a hard portion, or a soft portion and a hard portion, as needed.

The position control apparatus of the present invention may additionally include a driving device enabling an operation of the working devices. The driving device may additionally include a step or sub motor, the angle of which can be adjusted, which can rotate, a motor, a rack and pinion, or a gear apparatus.

According to the present invention, in order to perform position control of the transfer unit, the position control apparatus may additionally include a linear motion unit (for example, horizontal shaft 260) which enables the transfer unit to perform linear motion in the horizontal axis direction of the main platform, or the linear motion guiding unit (for example, horizontal axis sliding channel). Further, the position control apparatus may additionally include a rotary shaft which is formed in the body thereof, and is coupled to the linear motion unit or the linear motion guiding unit or is coupled to the transfer unit. The center of the rotary shaft may coincide with the central axis of the main platform.

Meanwhile, the position control apparatus may additionally include a moving system of the body 210. The moving system may be selected and used from the group consisting of (a) a driving or fixing nut, (b) a guiding tube which is a cylindrical tube and controls the linear motion and the rotational motion of the P-spin shaft, (c) a guiding bar which includes an upper cylinder, a lower cylinder and a body for connecting the upper cylinder and the lower cylinder to each other, is mounted on a recessed region formed on the outer peripheral surface of the main platform, and guides the linear motion of the working devices, (d) a P-spin shaft 230 which is mounted outside the body 210, adjusts the rotational motion and the vertical motion of the body, and operates as a linkage axis of the body, and (e) a combination thereof.

According to the present invention, the position control apparatus may additionally include a driving device enabling an operation of the transfer unit.

In accordance with other aspect of the present invention, there is provided a trans-platform apparatus (300) comprising:

(a) a cylindrical main platform (310) inserted into a working space, wherein electrical connection terminals (340) are formed on an outer peripheral surface of the main platform; and (b) a cylindrical working device (320) mounted on the outer peripheral surface of the main platform, wherein electrical connection terminals (340) are formed on a contact surface of the working device, which is in contact with the outer peripheral surface of the main platform.

The trans-platform apparatus 300 of the present invention uses a configuration and a driving principle of the above-described trans-platform apparatus 100, and common contents therebetween will be omitted in order to avoid making the present specification excessively complex.

The trans-platform apparatus 300 of the present invention using an electrical contact terminal may be applied even to a case where the working devices are mounted to the outside of the main platform not by the driving principle of the above-described trans-platform apparatus 100 but by another driving device (for example, Korean Patent Registration No. 10-1150350, "three-dimensional endoscopic surgical apparatus").

Unlike the trans-platform apparatus 100, the trans-platform apparatus 300 is characterized by controlling a position only by the positioner without the spin shaft.

The trans-platform apparatus 300 may additionally include (i) spin shafts 330 which are formed on the main platform or sides of the working devices, adjust the rotational motions and the linear motions of the working devices, and operate as linkage axes of the working devices, or (ii) linear motion units or linear motion guiding units which adjust the linear motions of the working devices in the horizontal direction of the main platform. For example, the trans-platform apparatus 300 may additionally include sliding channels, as a linear motion guiding unit, formed on the upper surfaces or the lower surfaces of the working devices, which are in contact with the main platform.

Meanwhile, for position control of the working devices, the trans-platform apparatus 300 may additionally include a transfer unit, and basically, the transfer unit operates in the same principle as for the transfer unit included in the above-described positioner.

According to the present invention, the electrical connection terminal 340 may be formed in (i) an "L" shape, (ii) a dot shape, (iii) a rectangular shape, or (iv) a combination of said shapes (see FIG. 36).

Meanwhile, when the trans-platform apparatus 300 is implemented by an endoscopic apparatus, the main platform moves to the inside of a human body, and thus, necessarily comes into contact with biofluid—moisture, blood, spit, mucus, synovial fluid of a joint, and the like. Further, since the electrical connection terminal is a portion through which a current flows, a means for preventing a contact between the biofluid and the electrical connection terminal is required. To this end, the entirety or a part of the outer peripheral surface of the main platform may be coated with a water repellent material. When a part of the outer peripheral surface is coated, only a portion around the electrical connection terminal 340 formed on the outer peripheral surface of the main platform may be subjected to water repellent coating. The water repellent coating material may include a wax and metallic soap, a formaldehyde compound, pyridine, a silicon-based compound, a fluorine-based compound, and the like. However, since the apparatus of the present invention should be used for mammals, materials having biocompatibility among the materials may be selectively used. That is, for example, fluorine resin of PolyTetraFluoroEthylene (PTFE), silicone, gelatin, rubber, and the like as biocompatible and nonconductive materials may be used as the water repellent material, but the present invention is not limited thereto.

Advantageous Effects

Features and advantages of the present invention are summarized as follows:

(a) The present invention relates to a trans-platform apparatus including a main platform and an operating device.

(b) The trans-platform apparatus of the present invention has the advantage of performing complex and various operations by inserting a maximum number/size of operating devices through a minimal number of openings within an operating space.

(c) In addition, since the trans-platform apparatus of the present invention does not use an additional connecting member for a spin shaft, the configuration thereof is further simplified, the operation thereof is easier, and power can be efficiently transmitted to an operating means.

(d) The trans-platform apparatus of the present invention is applicable to various fields including various medical devices, such as an endoscope for operation, which includes surgical instruments, an ultrasonic-assisted catheter provided with an ultrasonic probe and a multi-purpose robot arm having a medical device provided to the fore-end of a single main platform, and the like, and also an engine room or a device for operating the inside of a radiator and the like.

When the outer diameter of the main platform of the "trans-platform apparatus" of the present invention is equal to the outer diameter of the main tube of the "three-dimensional endoscopic surgical apparatus", the radiuses of the working devices mounted to the tip ends of the two apparatuses are as follows: (1) the radius of the working device mounted to the main platform of the "trans-platform apparatus" of the present invention is equal to the radius of the main platform, but (2) the radius of the working device mounted to the "three-dimensional endoscopic surgical apparatus" according to the related art is equal to a length obtained by subtracting the thicknesses of the outer tube and the inner tube and the diameter of the spin shaft hole from the radius of the main tube. In the apparatus of the present invention, since the diameter of the main platform is equal to the diameter of the working device, the diameter of the working device mounted to the main platform of the trans-platform apparatus of the present invention is larger than the diameter of the working device mounted to the "three-dimensional endoscopic surgical apparatus".

Figure 1:
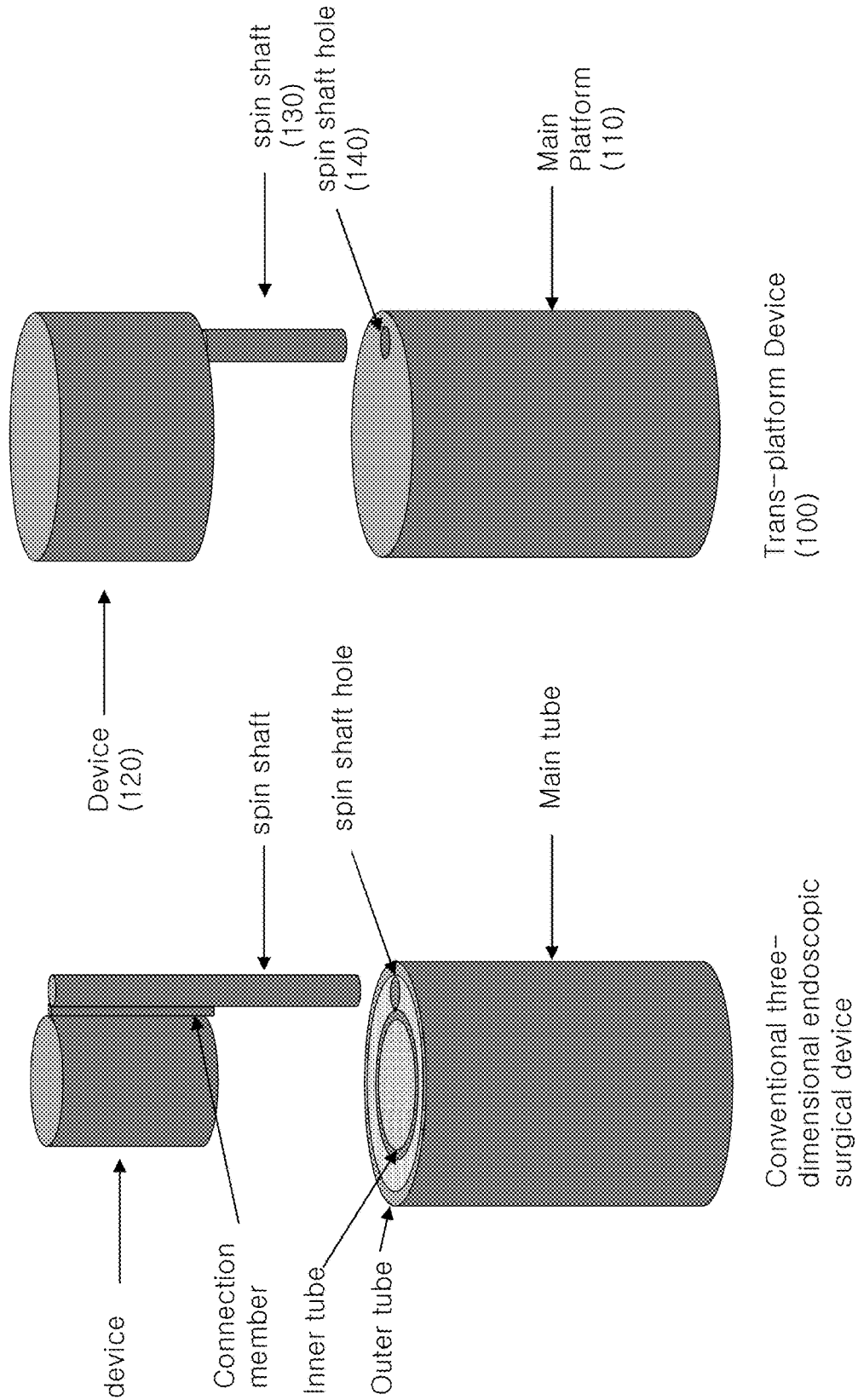
FIG. 1 is a perspective view illustrating the three-dimensional endoscopic surgical device according to the related art and the trans-platform apparatus of the present invention.
Figure 2:
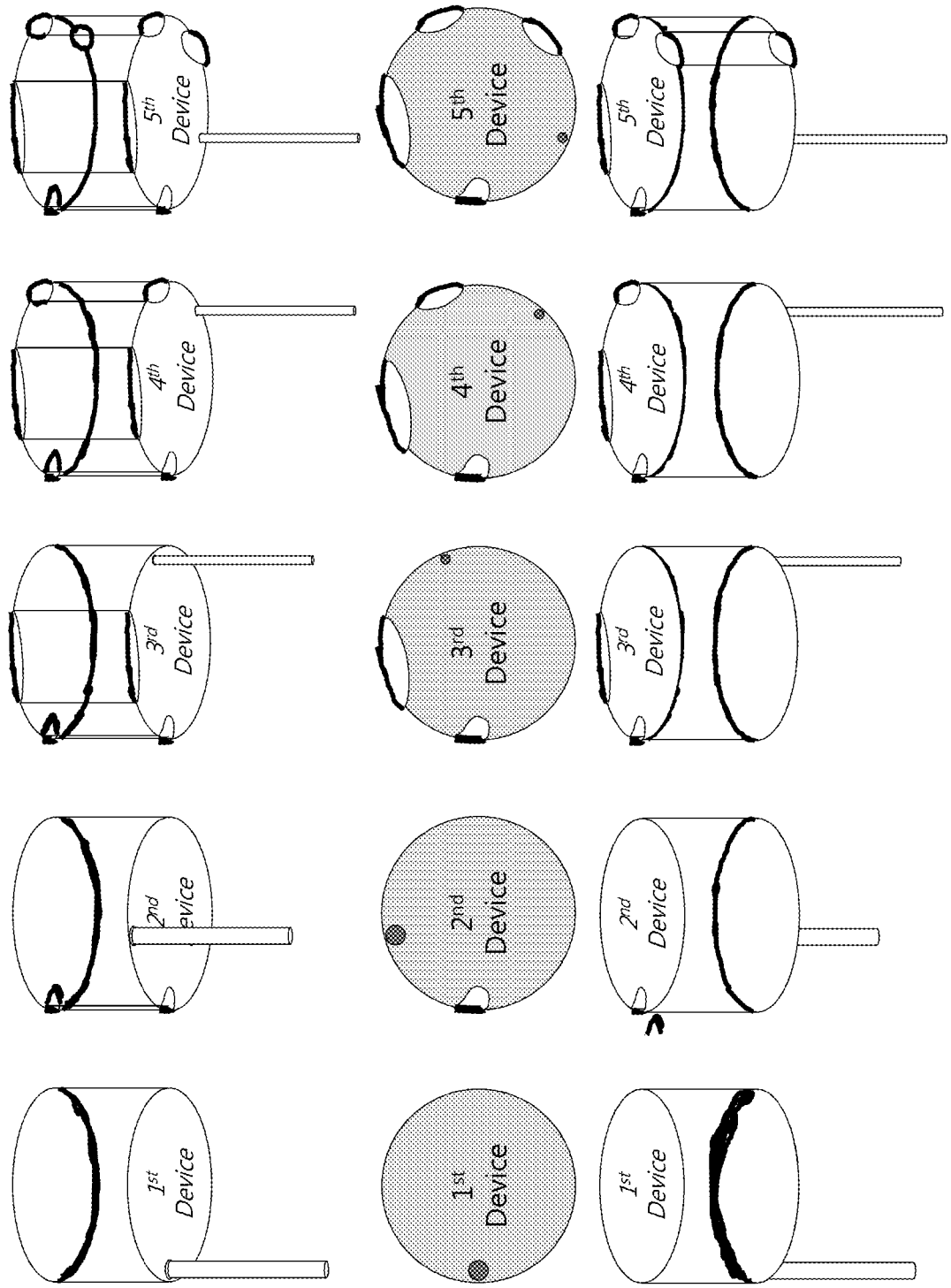

FIG. 2 illustrates a sectional view and a three-dimensional view of the working device mounted to the main platform of the trans-platform apparatus of the present invention. A yellow figure indicates the bottom surface of the working device, and a purple circle inside the yellow figure indicates the spin shaft. The three-dimensional view indicates a three-dimensional view when the working device is viewed from below and a three-dimensional view when the working device is viewed from above.

Figure 3:
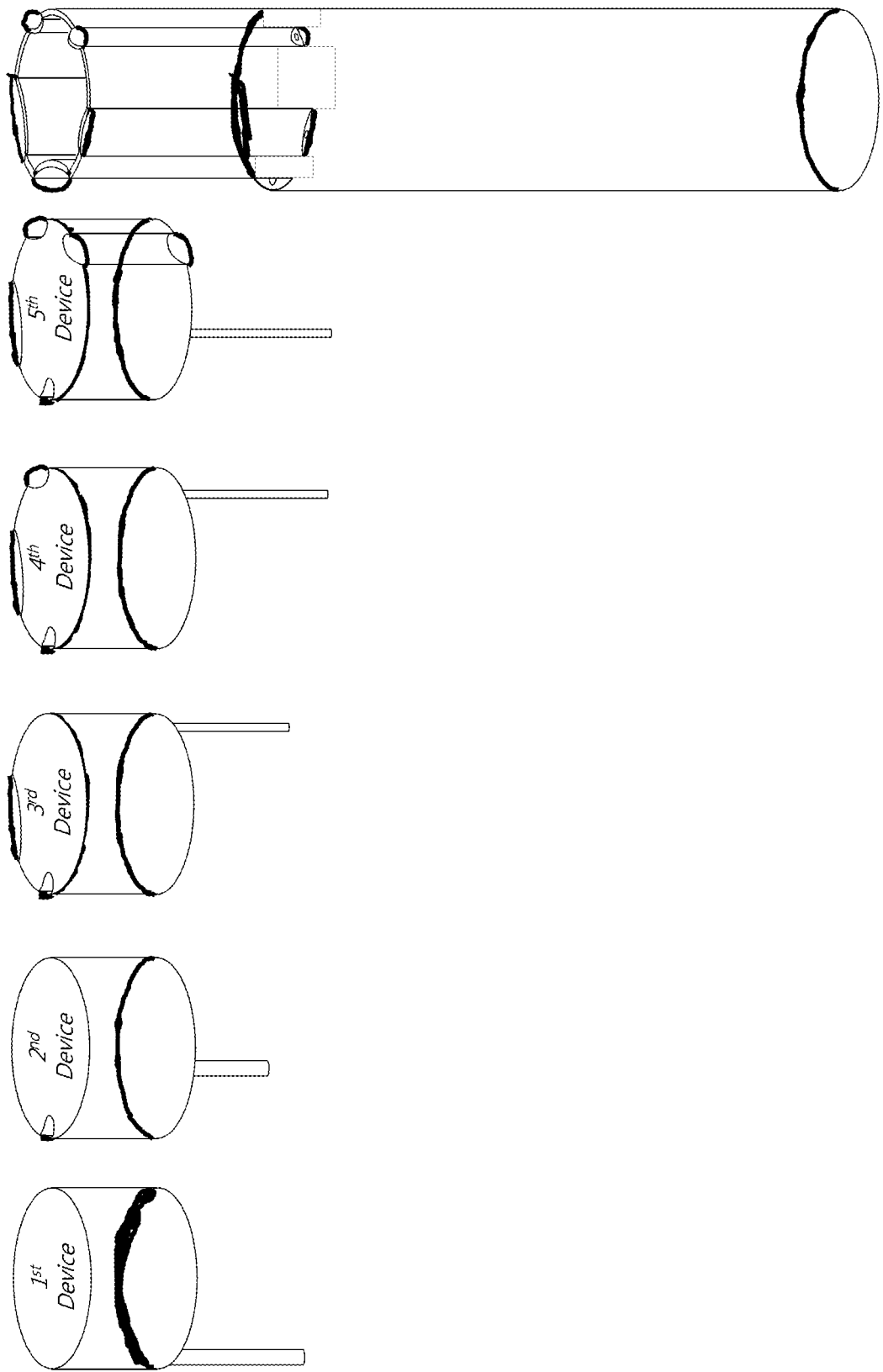

FIG. 3 a three-dimensional view illustrating the working device mounted to the main platform, and the main platform of the trans-platform apparatus of the present invention.

Figure 4:
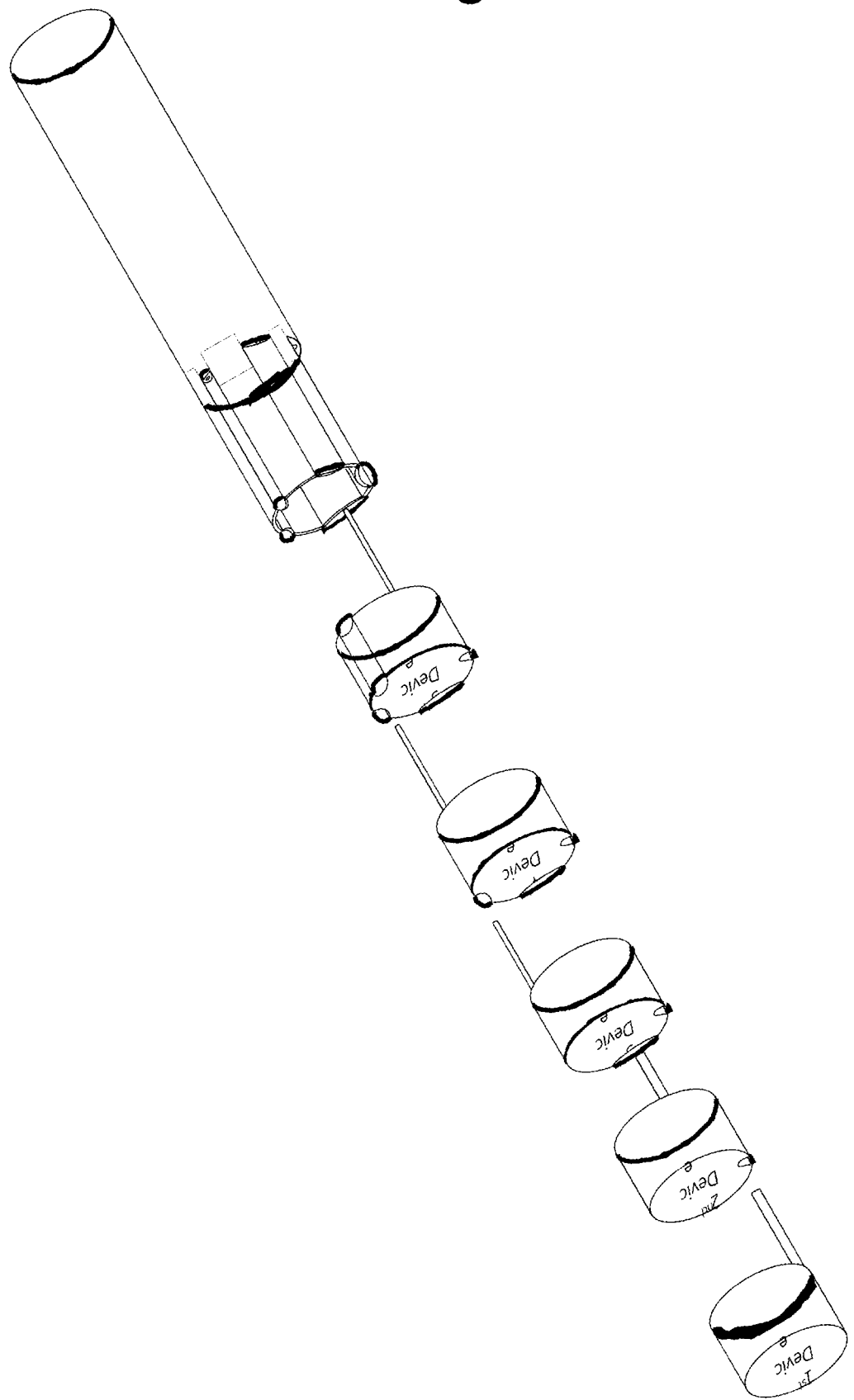
Figure 5:
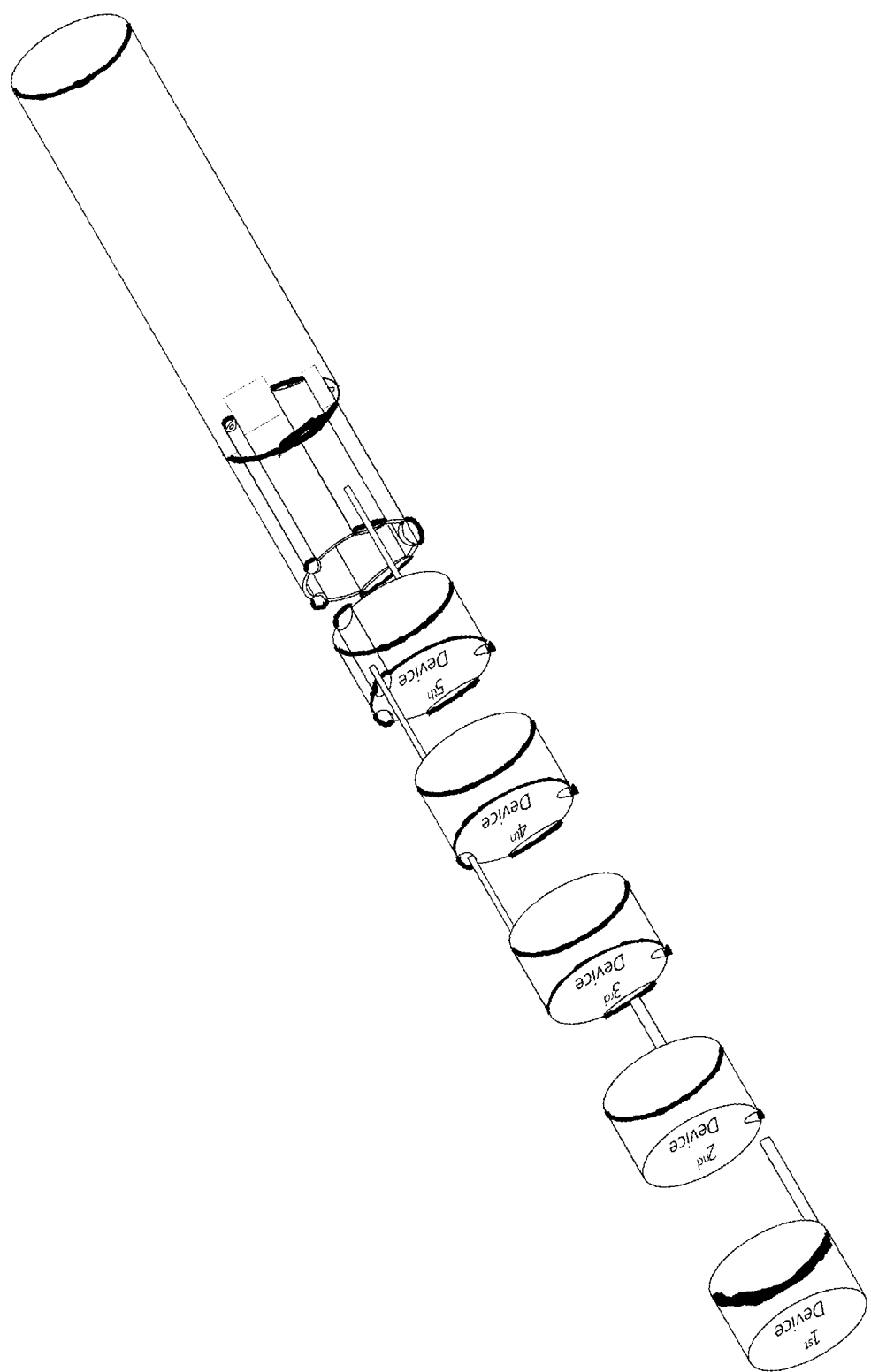
Figure 6:
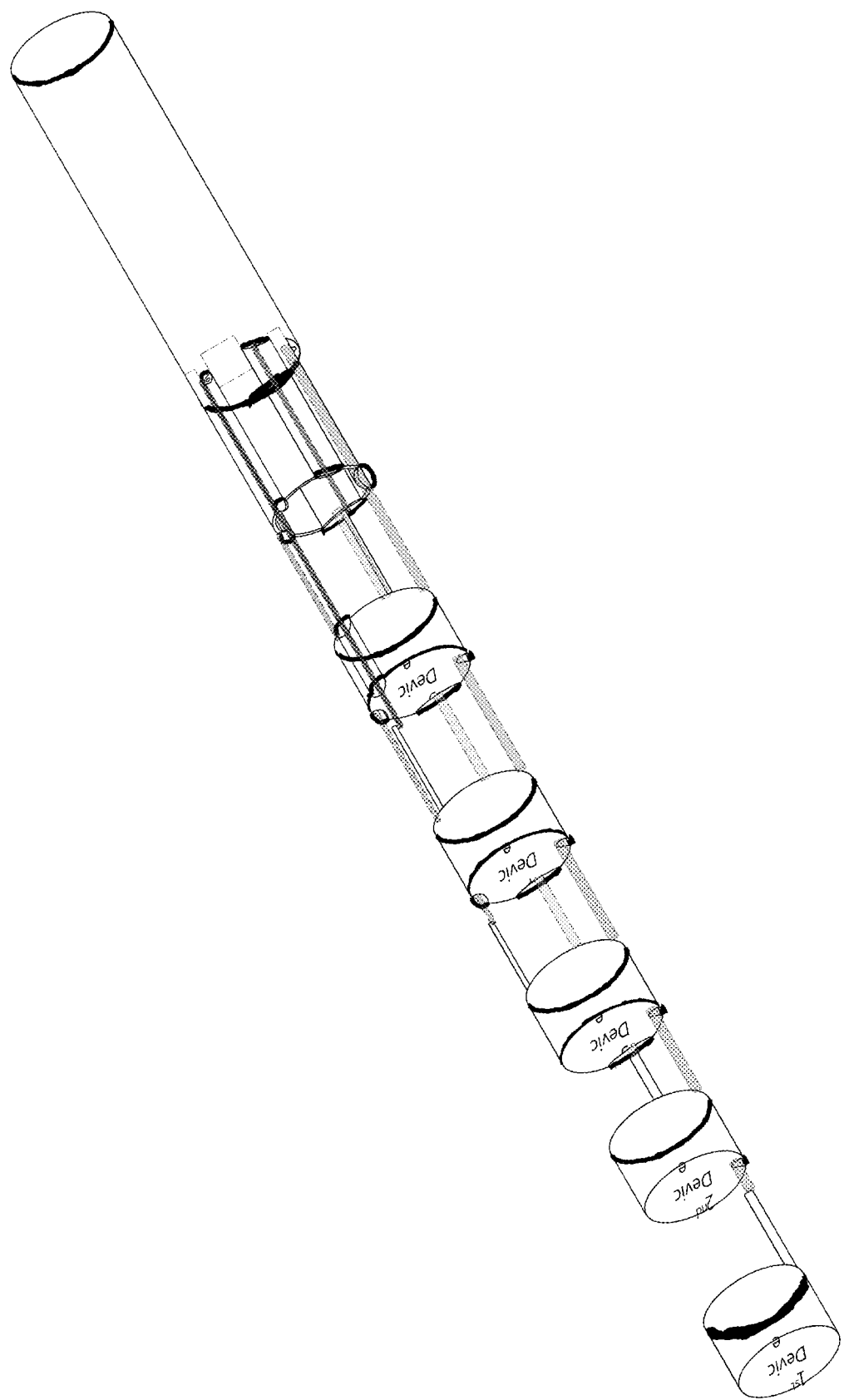

FIGS. 4 to 6 illustrate a configuration of the trans-platform apparatus and a flowchart for coupling each configuration according to an embodiment of the present invention.

Figure 7:
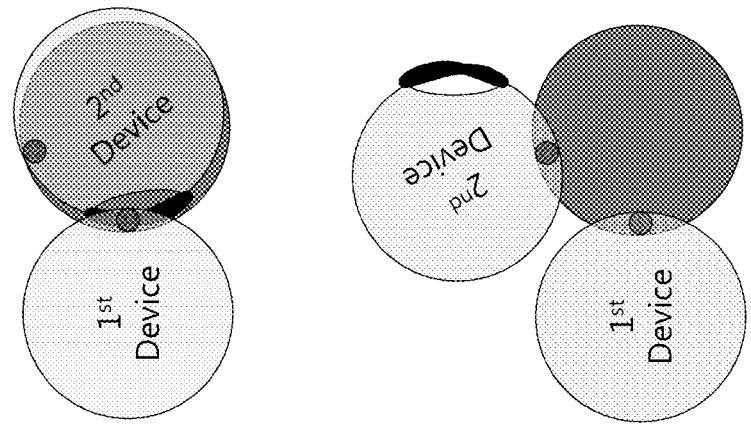
Figure 7:
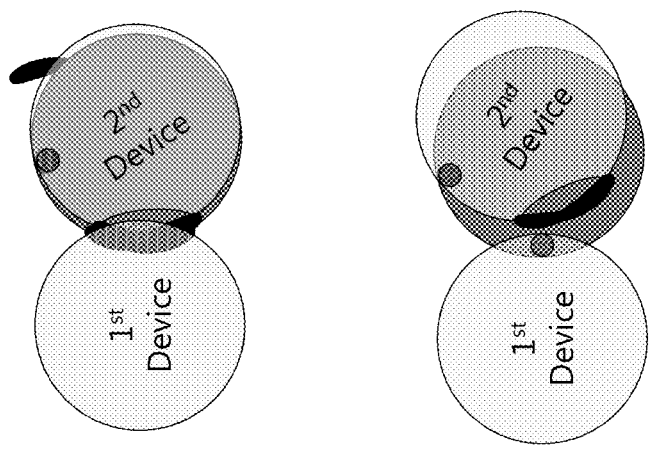
Figure 7:
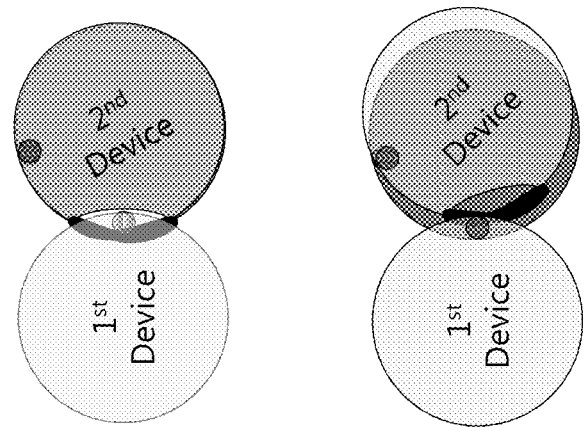

FIG. 7 is a plan view illustrating motions of the working devices according to positions thereof, and illustrates rotation of a spin shaft of a first working device and a second working device. When the first working device is mounted to the main platform by the backward motion of the first working device and the spin shaft, the first working device should not overlap the second working device, and thus, a space for the second working device is assigned to a space other than a predetermined space where the first working device and the spin shaft mounted to the first working device can perform a rotational motion and a vertical motion. The trans-platform apparatus may additionally include another auxiliary device as well as the spin shaft as a device for mechanically connecting and fixing each working device and the main platform.

Figure 8:
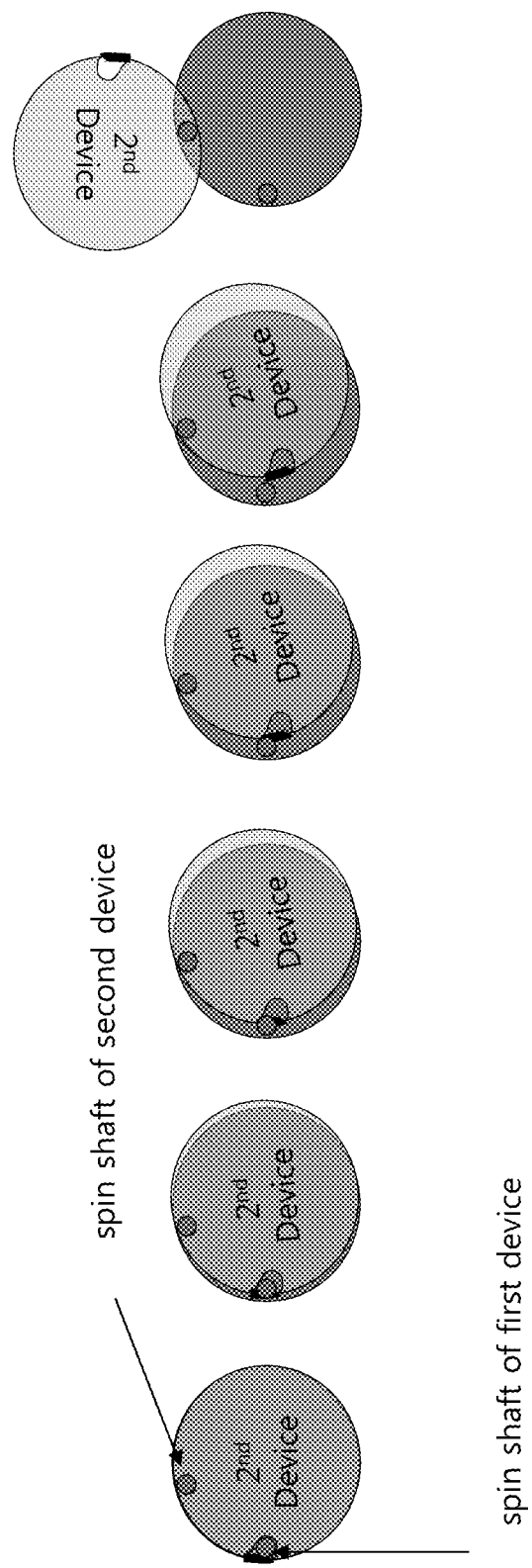

FIG. 8 is a plan view illustrating motions of the working devices according to positions thereof, and illustrates that the first working device moves backward and is not mounted to the main platform, and the second working device rotates. A cross-section of the second working device is designed to exclude a space where the rotation by the spin shaft of the first working device is not disturbed.

Figure 9:
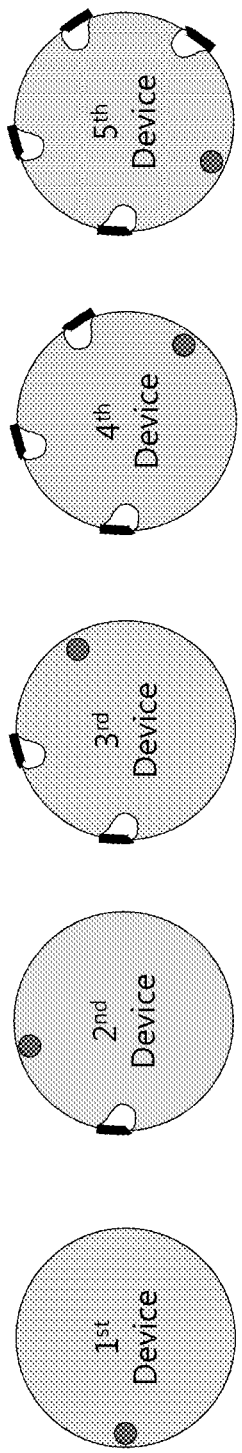

FIG. 9 illustrates the cross-sections of the working devices and the spin shafts when all the working devices do not move backward, are rotated, move backward, and are then mounted to the main platform. The views are a plan view when the spin shaft is mounted to the first working device; and plan views when spin shafts of the second working device to the fifth working device are mounted to a space other than a space of a spin shaft of a prior working device and a rotation space thereof.

Figure 10:
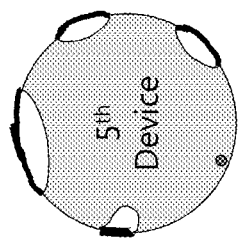
Figure 10:
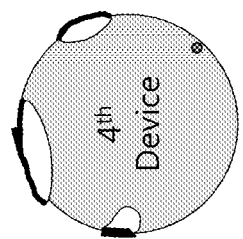
Figure 10:
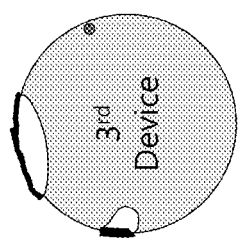
Figure 10:
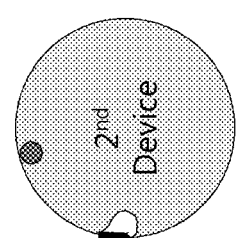
Figure 10:
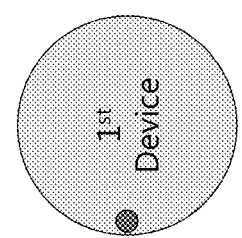

FIG. 10 is a plan view when spin shafts are mounted to working devices, respectively. The working devices mounted at the tip end of the main platform may not be mounted in a mounting order, that is, may not be mounted while rotating in order according to the numbers thereof, and the sizes of the spin shafts of all the working devices mounted at the tip end of the main platform may be changed according to the uses of the working devices. As illustrated in FIG. 10, spin shafts of the first working device and the second working device are large, and spin shafts of the third working device to the fifth working device are small. When a rotationally mounted order is an order of the second working device, the third working device, the fourth working device, the fifth working device, and the first working device, the lower plan view of each working device is identical to FIG. 10.

Figure 11:
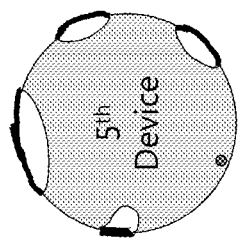
Figure 11:
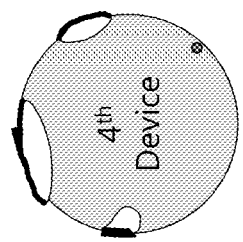
Figure 11:
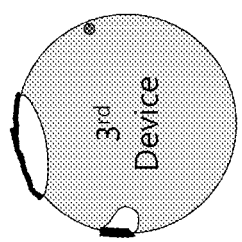
Figure 11:
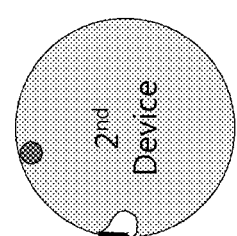
Figure 11:
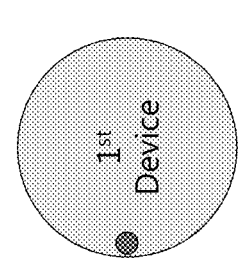

FIG. 11 is (a) a perspective view illustrating the main platform, (b) an upper plan view illustrating the main platform, and (c) an upper sectional view illustrating the main platform of the trans-platform apparatus of the present invention. The working devices are mounted to a recessed region of (c). The working devices mounted to the tip end of the main platform can be coupled to the spin shaft holes through the spin shafts, respectively.

Figure 12:
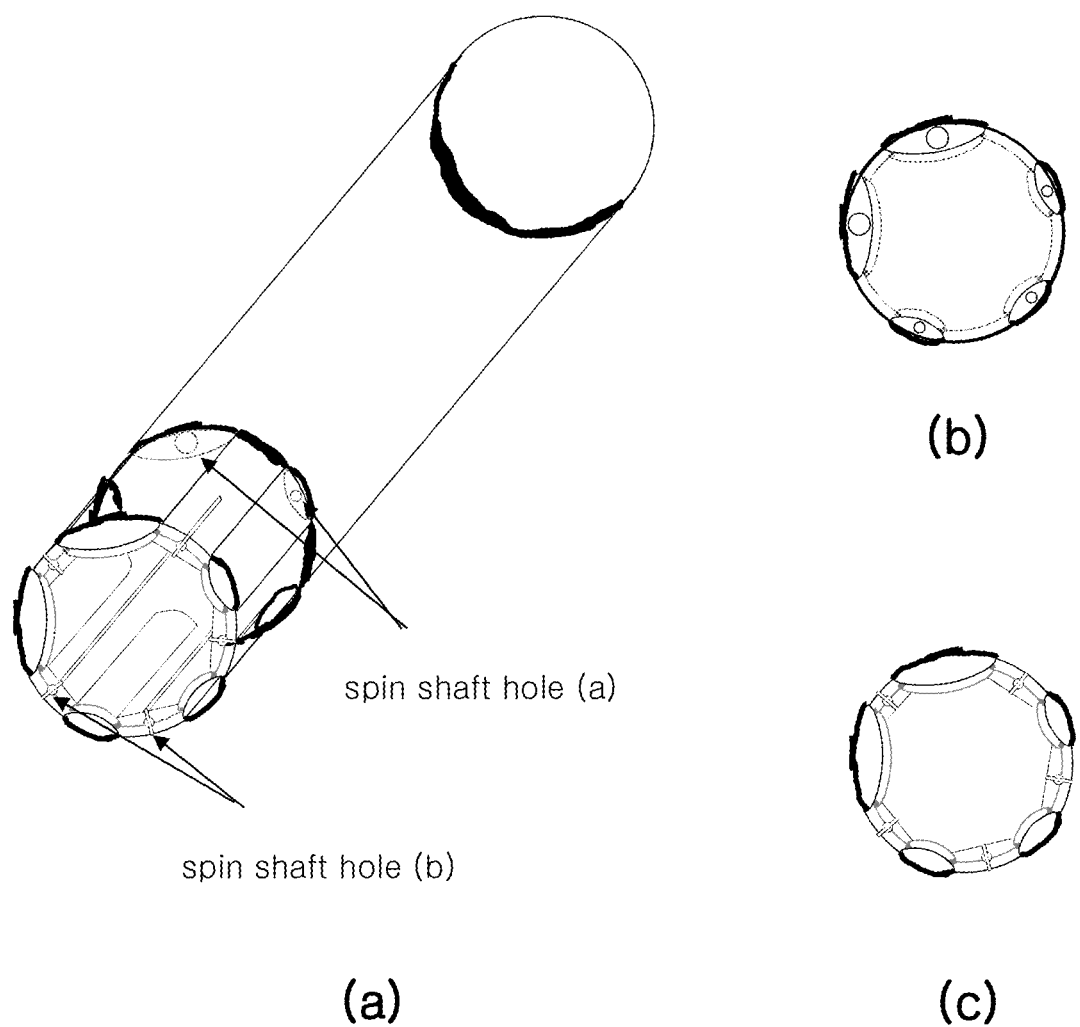

FIG. 12 illustrates the shape of the main platform having holes additionally installed therein to which the working devices mounted to the inside of the main platform are fixed. FIG. 12A is a perspective view illustrating the main platform, FIG. 12B is an upper plan view illustrating the main platform, and FIG. 12C is an upper sectional view illustrating the main platform except for a part of a working device mounted portion. The working devices mounted to the tip end of the main platform can be coupled to (a) the spin shaft holes through the spin shafts, respectively, and the working devices mounted to the inside of the main platform can be coupled to (b) the spin shaft holes, respectively. The spin shaft holes may be manufactured to have various sizes, and the sizes and the shapes of mounting portions may be changed according to the shapes of the working devices. In the drawings, a portion where the working devices are located at the tip end of the main platform and are then mounted is recessed. Further, a portion where the working devices which are located inside the main platform and are then mounted is not recessed, and in this case, although not illustrated, the working devices are recessed. When the working devices not having the spin shafts are mounted, the spin shaft holes may be omitted.

Figure 13:
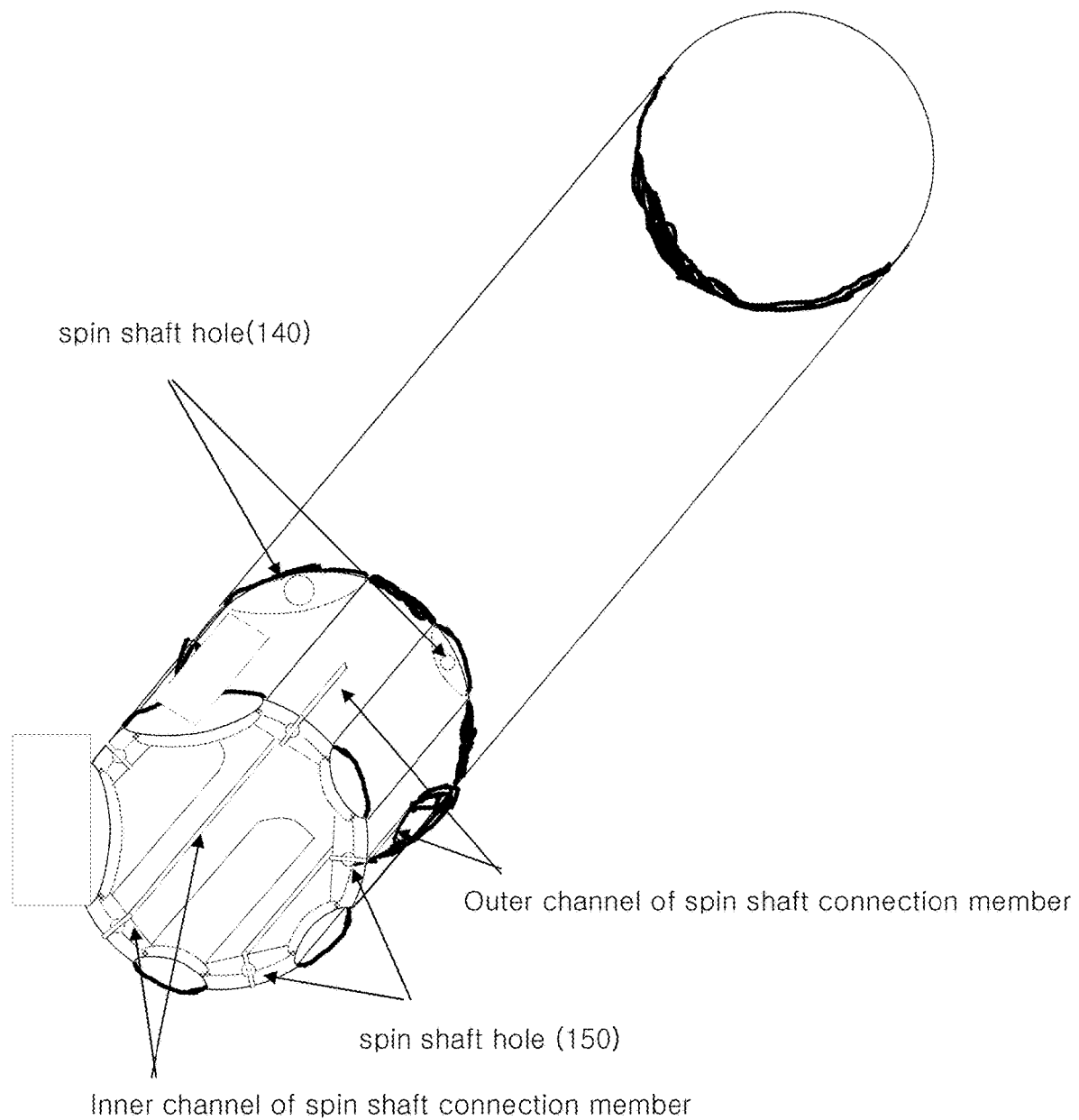

FIG. 13 is an enlarged view illustrating the main platform of FIG. 12.

Figure 14:
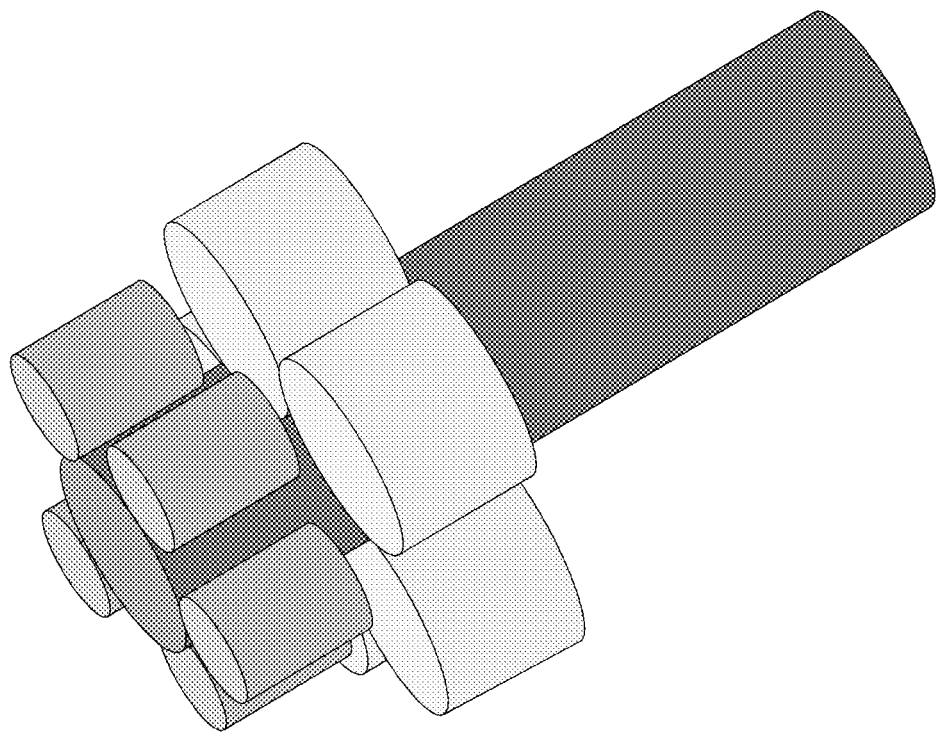

FIG. 14 is a perspective view illustrating a case where the working devices coupled to the tip end of the main platform and the working devices included inside the main platform are mounted all together. Blue color indicates the main platform, yellow color indicates the working devices mounted at the tip end of the main platform, and green color indicates the working devices included inside the main platform. The yellow and green working devices are driven individually or are driven while being mechanically coupled to each other. When being driven while being mechanically coupled to each other, the working devices can perform more complex and various functions.

Figure 15:
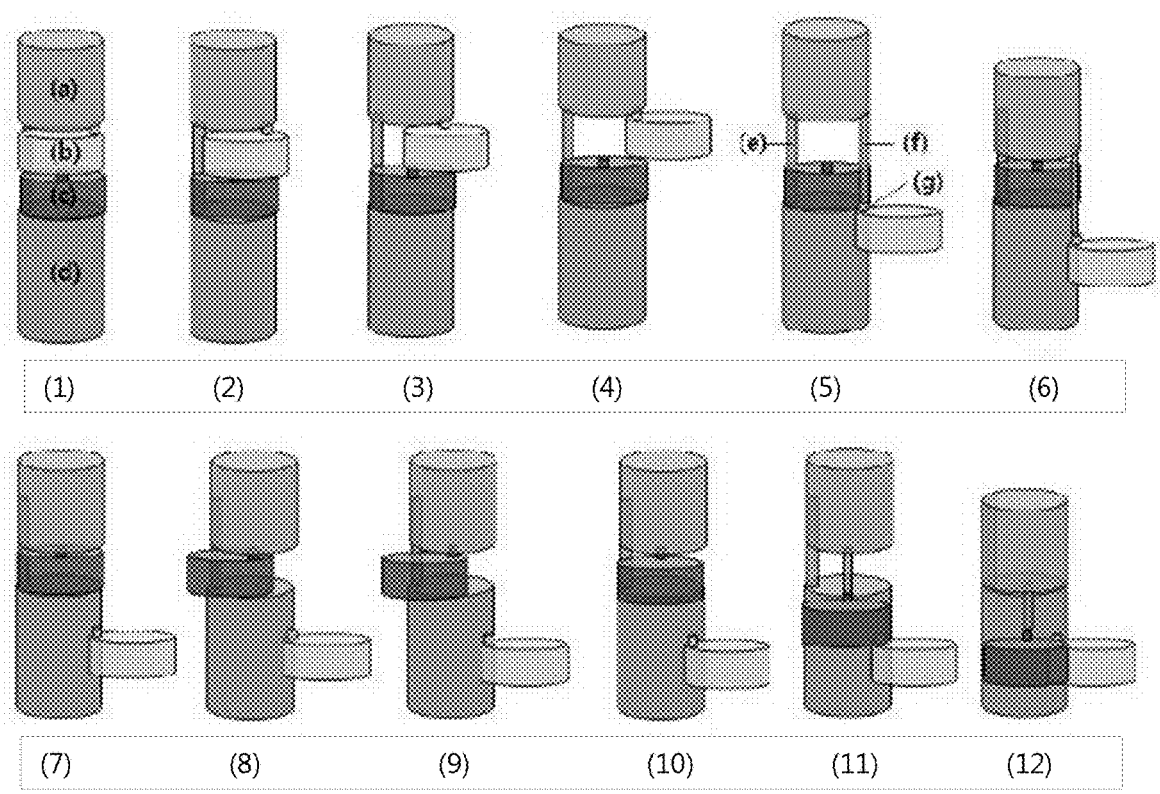
Figure 16:
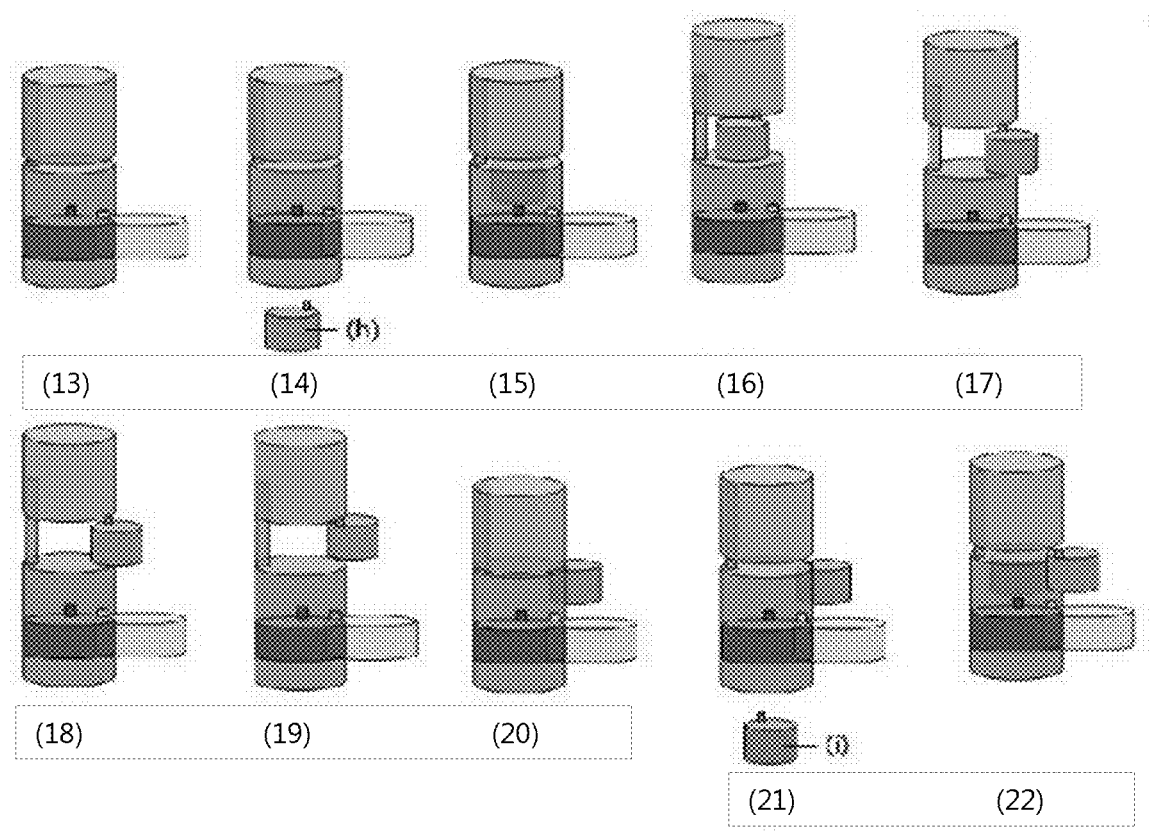
Figure 17:
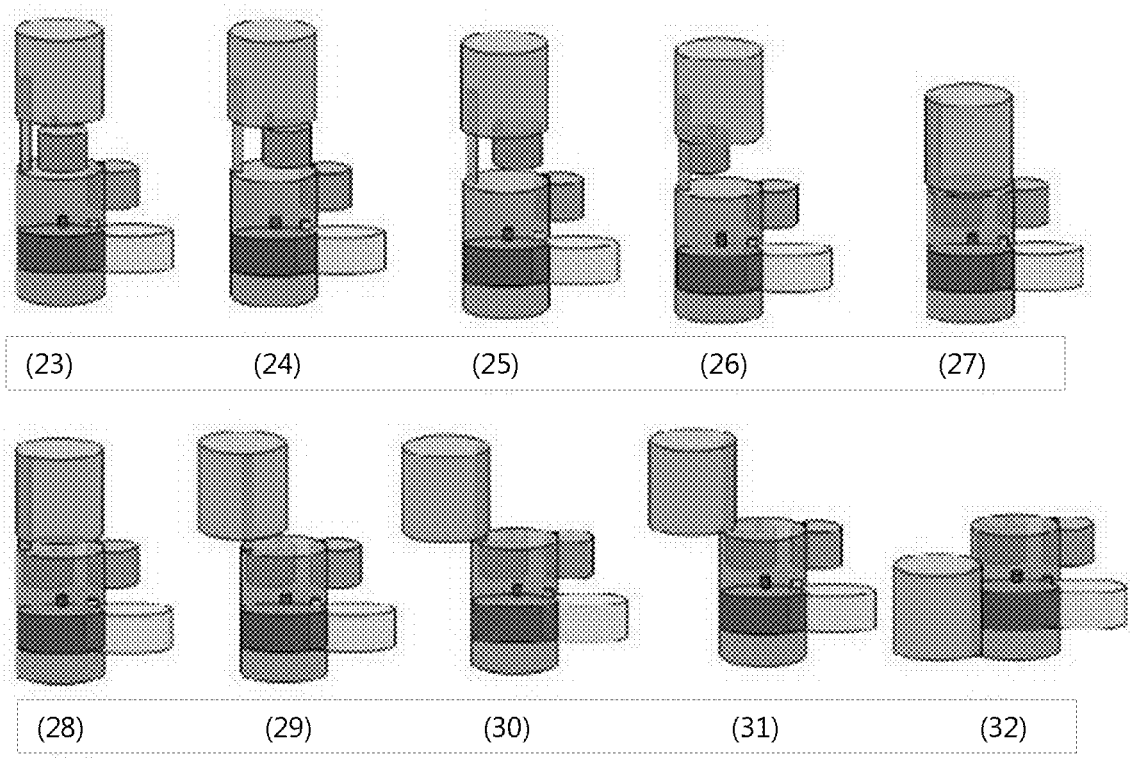

FIGS. 15 to 17 schematically illustrate a process of completing the shape of FIG. 14. The process of FIGS. 15 to 17 will be sequentially described as follows.

(1) The trans-platform apparatus of the present invention is configured by "positioner (a)—working device (b: yellow)—working device 2 (c: purple)—main platform (d)".

(2)(3)(4) The working device is rotated by 180 degrees by coupling a coupling protrusion (g) of the first working device and a transfer unit (f; figures of capturer unit and T spin shaft capturer are omitted) within the positioner to each other.

(5) (6) The transfer unit and the working device move backward while a capturer unit (g) and a spin shaft (f; T-spin shaft) are coupled to each other, so that the working device is coupled and mounted to the outer peripheral surface of the main platform. After the working device is mounted, the coupling between the coupling protrusion of the working device and the capturer unit is released (capturer unit (g), T-spin shaft (f)).

(7) The capturer unit and the coupling protrusion of the working device are separated from each other, and the T-spin shaft is retrieved to the inside of the positioner. Thereafter, a coupling protrusion of the second working device and a second capturer unit are coupled to each other.

(8)(9)(10) The second working device is rotated by rotation of a second T-spin shaft.

(11) The second T-spin shaft is moved backward so that the second working device is moved backward.

(12) When the second working device is not mounted to a desired position of the main platform by the operation of (11), the positioner itself is moved backward additionally by rotation of a P spin shaft so that the second working device can further move. Thereafter, the capturer unit and the coupling protrusion of the second working device are separated from each other.

(13) The T-spin shaft coupled to the second working device is retrieved to the inside of the positioner.

(14)(15)(16) A third working device (h; pink) is moved through the inside of the main platform so as to be located below the positioner. A coupling protrusion of the third working device and a capturer unit below the positioner are coupled to each other.

(17)(18)(19) The third working device is rotated by 180 degrees by rotating the T-spin shaft in a state in which a third capturer unit and the third working device are coupled to each other. Here, the third working device passes through the inside of the main platform and then moves to the outside. Thus, when the third working device is rotated about a central axis to which the protrusion of the working device and the capturer unit are coupled, it is difficult to mount the third working device to the outer peripheral surface of the main platform. Although not illustrated, the third capturer unit and a third T-spin shaft are connected to each other in a crank type, and thus, when the third T-spin shaft is rotated by 180 degrees, the third working device is located to a position to be mounted to the outer peripheral surface of the main platform.

(20) The positioner is moved backward through a screw motion of the P-spin shaft (e) so that the third working device is moved backward and is mounted to the main platform.

(21) to (27) A fourth working device (i; green) is mounted to the main platform by the same process of (14) to (20).

(28) The coupling between a fourth capturer unit and a coupling protrusion of the fourth working device is released.

(29)(30)(31) The positioner is rotated by 180 degrees by rotation of the P-spin shaft.

(32) The positioner is moved backward through the screw motion of the P-spin shaft so as to be mounted to the outer peripheral surface of the main platform.

Figure 18:
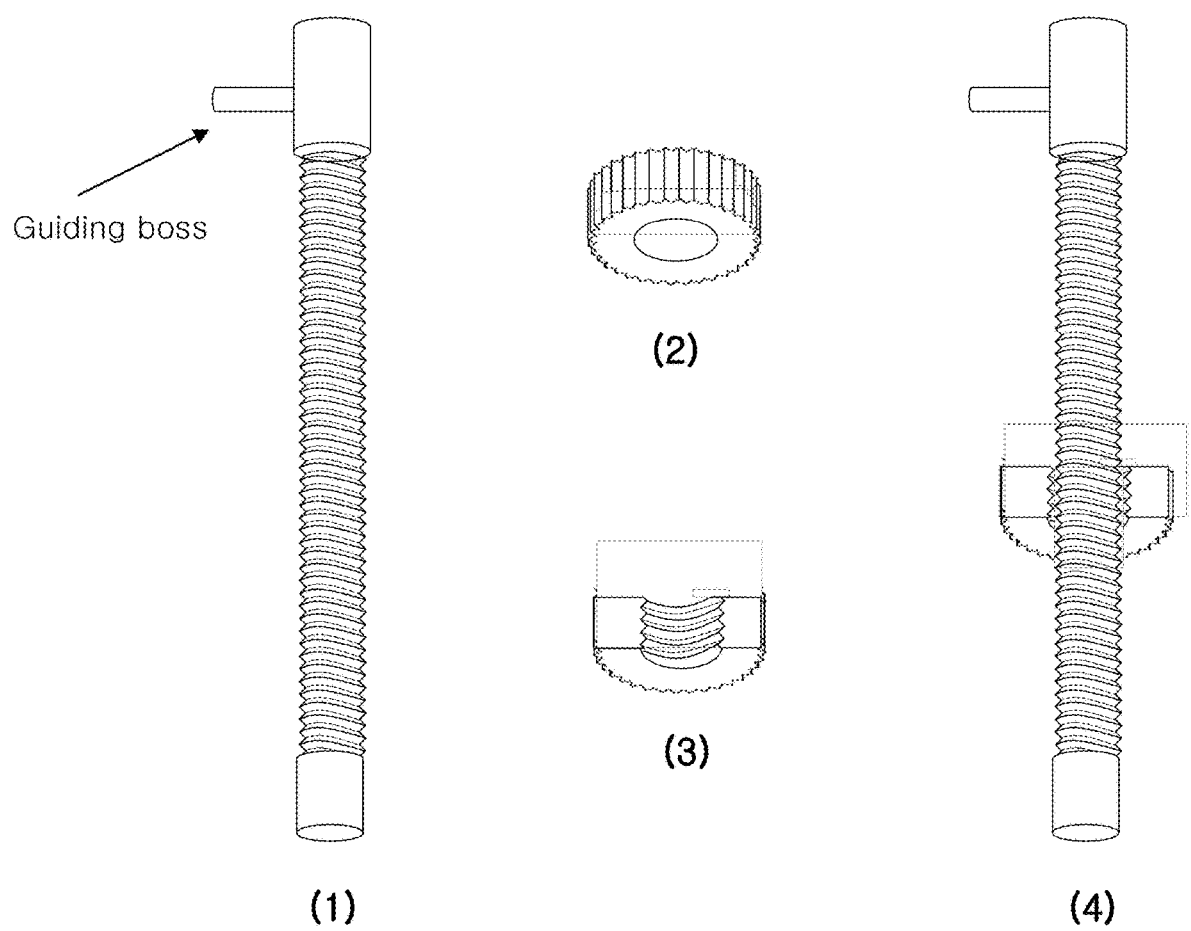

FIG. 18 illustrates coupling between the spin shaft and the nut among a configuration for the screw motion of the spin shaft. A male screw thread and a guiding boss used for a guiding tube is installed in a spin shaft (1). A power transmission gear, a capturer unit or the like may be coupled to an end of the spin shaft as needed. (2) and (3) are a three-dimensional view and a sectional view of a nut. A female screw thread is formed on the inner surface of the nut. Further, a gear may be installed on the outer surface or another structure may be coupled to the outer surface, as needed. In the drawing, the gear is installed. (4) is a three-dimensional view illustrating a state in which the nut and the spin shaft are coupled to each other.

Figure 19:
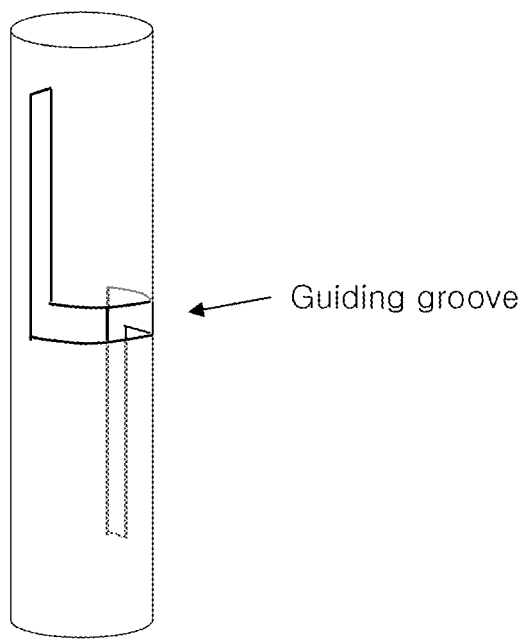

FIG. 19 illustrates a guiding tube having a guiding groove formed therein along which the guiding boss can be moved, according to the present invention. The guiding groove may be manufactured in various shapes in accordance with objects.

Figure 20:
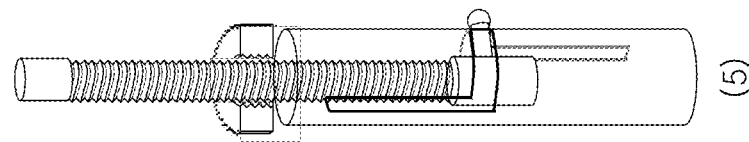
Figure 20:
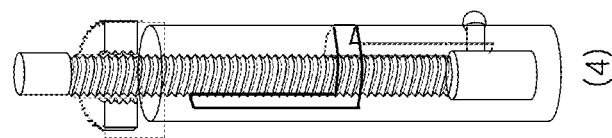
Figure 20:
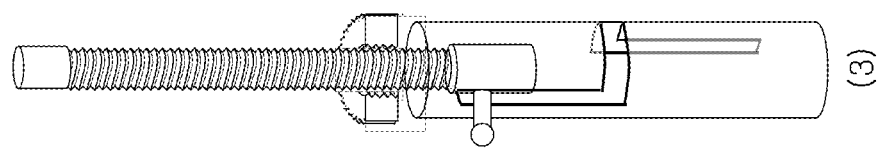
Figure 20:
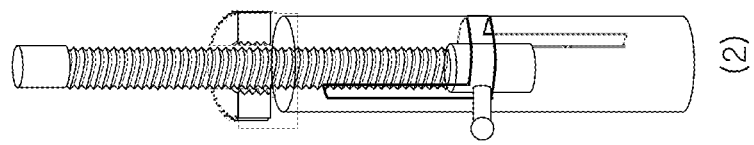
Figure 20:
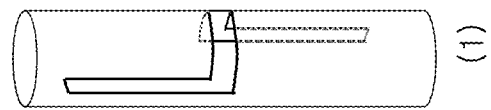

FIG. 20 illustrates the spin shaft, the nut, and the guiding tube which perform the screw motion when the moving system is formed inside the main platform. The working device (not illustrated) or the positioner (not illustrated) is coupled to the upper end of the spin shaft, the nut and the guiding tube are located on the main platform, and the nut is driven through the motor and the gear (not illustrated) located on the main platform. The spin shaft performs the screw motion by rotating the driving nut, and the rotational motion and the vertical linear motion of the spin shaft are determined by the guiding tube. (1) illustrates the guiding tube, wherein portions displayed in red color (front part) and pink color (rear part) illustrate guiding grooves. (2) illustrates positions of the spin shaft and the guiding tube at an initial position of the working device or the positioner, and when the driving nut is rotated in a clockwise direction, the spin shaft moves upward (3). When the driving nut is rotated in the counterclockwise direction, the spin shaft reaches at the position of (2) again, and when the driving nut is continuously rotated in the counterclockwise direction, the spin shaft is rotated to a position of (4) so that the working device or the positioner is rotated by 180 degrees. Thereafter, when the driving nut is continuously rotated in the counterclockwise direction, the spin shaft moves downward, is at a position of (5), and is mounted to the main platform. The above process may be performed in a reverse order, thereby adjusting the position of the spin shafts and the working devices coupled to the spin shafts. Thereafter, the distances of the rotation, the forward motion, and the backward motion can be adjusted according to the guiding groove.

Figure 21:
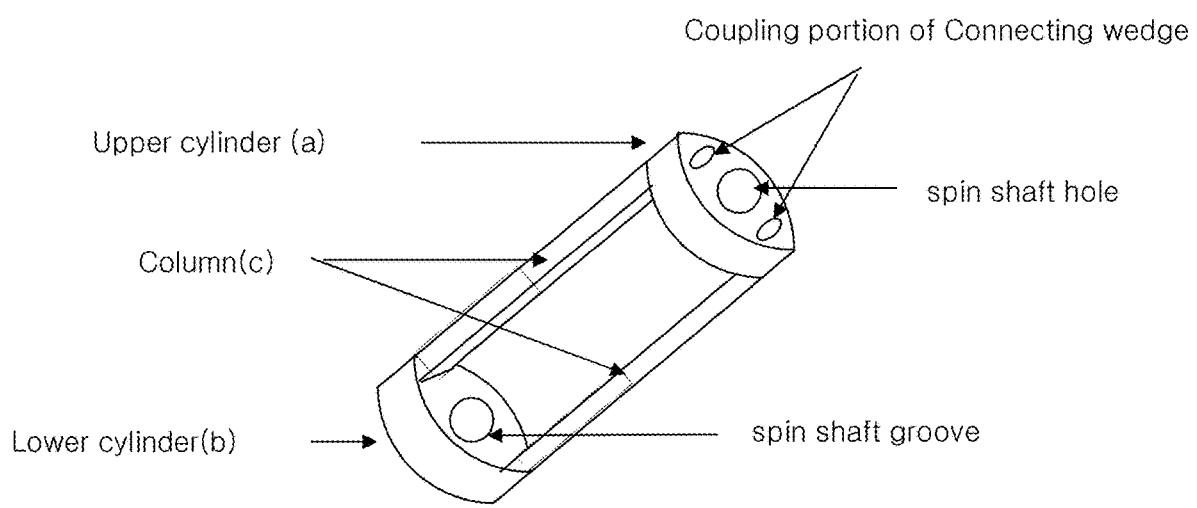

FIG. 21 illustrates a three-dimensional view illustrating a guiding bar of the present invention. The guiding bar includes (a) an upper portion and (b) a lower portion which have an approximately cylindrical shape, and (c) two columns for connecting the two cylinders to each other. The guiding bar is used while being mounted to the recessed region formed on the main platform, and thus, is designed in accordance with the shape of the recessed region. Thus, the guiding bar has not a complete cylindrical shape but an approximately cylindrical shape having an elliptical bottom surface, both ends of which are sharp, as illustrated in FIG. 21. Such a design is for maximizing space utilization of an empty space in a state in which the working device and the main platform are in close contact with each other. The upper cylinder has a coupling portion formed therein between the connection wedge and a hole through which the spin shaft passes. The lower cylinder has a groove through which the spin shaft passes, and has a space formed therein where the spin shaft tip may be positioned. Accordingly, the guiding bar performs the vertical motion together while being coupled to the spin shaft, but does not disturb the rotational motion of the spin shaft.

Figure 22:
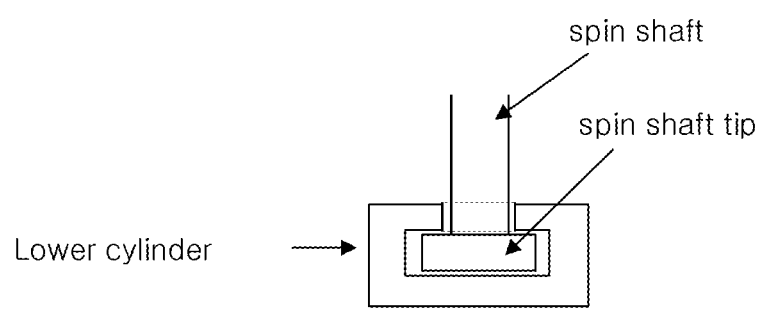

FIG. 22 illustrates the inside of the lower cylinder of the guiding bar. The lower cylinder and the spin shaft are fixed in a form in which the spin shaft tip is surrounded by the lower cylinder, and thus, are designed such that the lower cylinder and the spin shaft perform the linear vertical motion while being engaged with each other, and the spin shaft performs the rotational motion while being slid from the inside of the lower cylinder.

Figure 23:
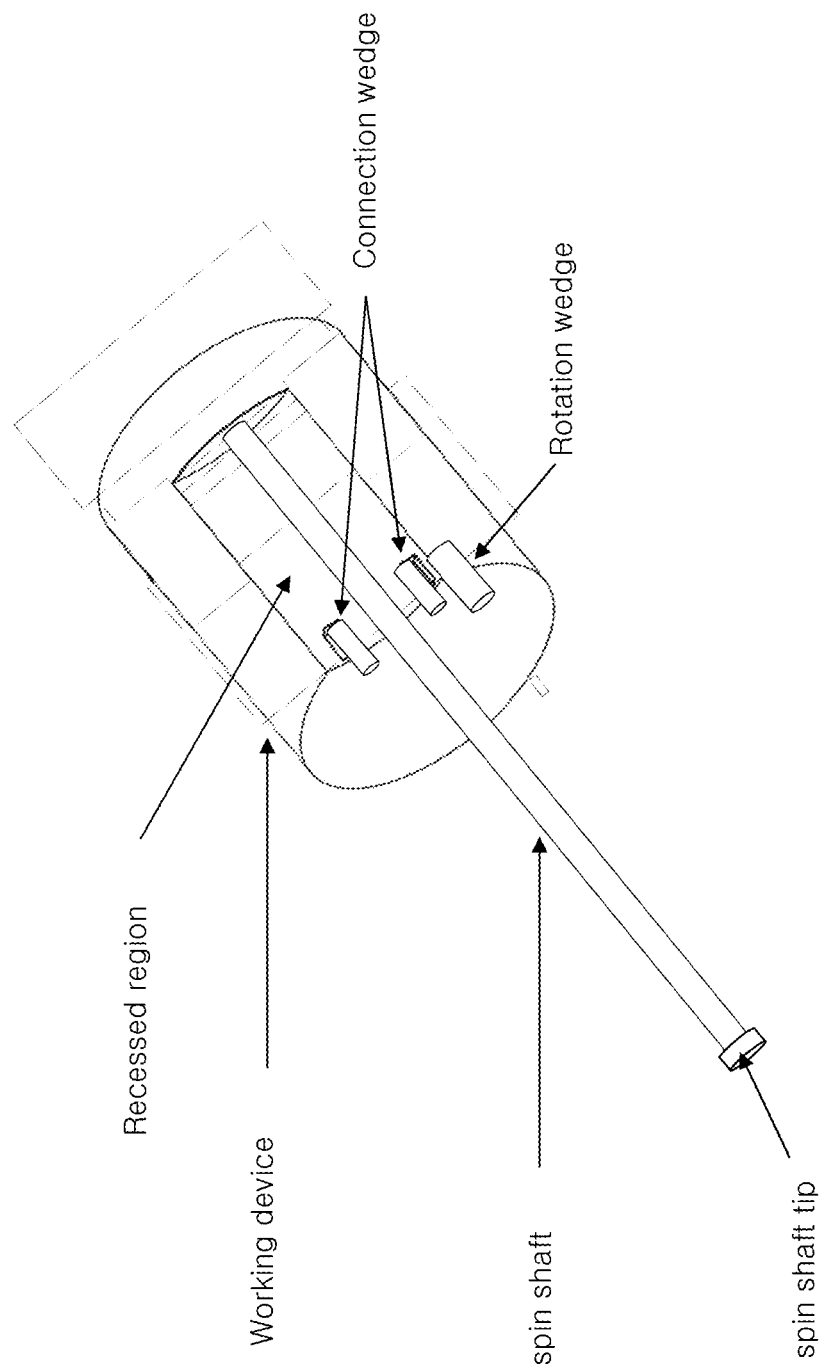

FIG. 23 is a schematic view illustrating a configuration in which a spin shaft, a connection wedge, and a rotation wedge are formed in a working device. The connection wedge serves to connect and couple the guiding bar and the working device. In order to transfer power to the spin shaft, a motor or a gear may be additionally mounted. The motor or the gear transfers rotational force to the spin shaft or the driving nut coupled to the spin shaft. The recessed region formed in the working device is engaged with the guiding bar such that the working device is coupled to the main platform. The connection wedge for mechanically connecting the guiding bar and the working device to each other may be formed in the recessed region. The spin shaft tip is coupled to the lower cylinder of the guiding bar.

Figure 24:
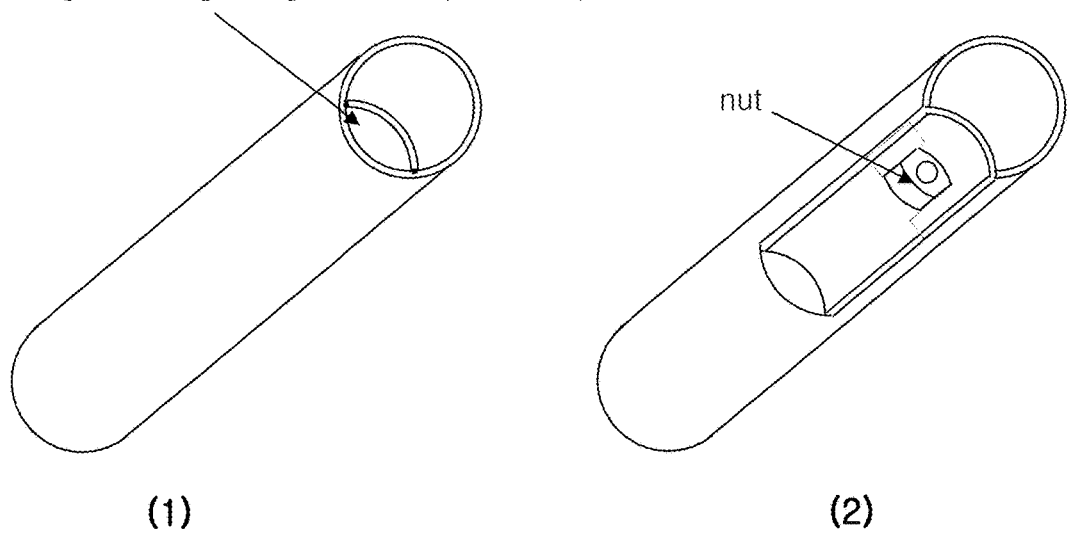

(1) of FIG. 24 illustrates the shape of the main platform when a space through which the guiding bar and the spin shaft pass is formed (see (1) of FIG. 24). (2) of FIG. 24 illustrates the inside of the main platform when a nut in addition to the guiding bar is formed additionally. A nut having a female screw formed therein to be engaged with the spin shaft is formed in the recessed region of the main platform.

Figure 25:
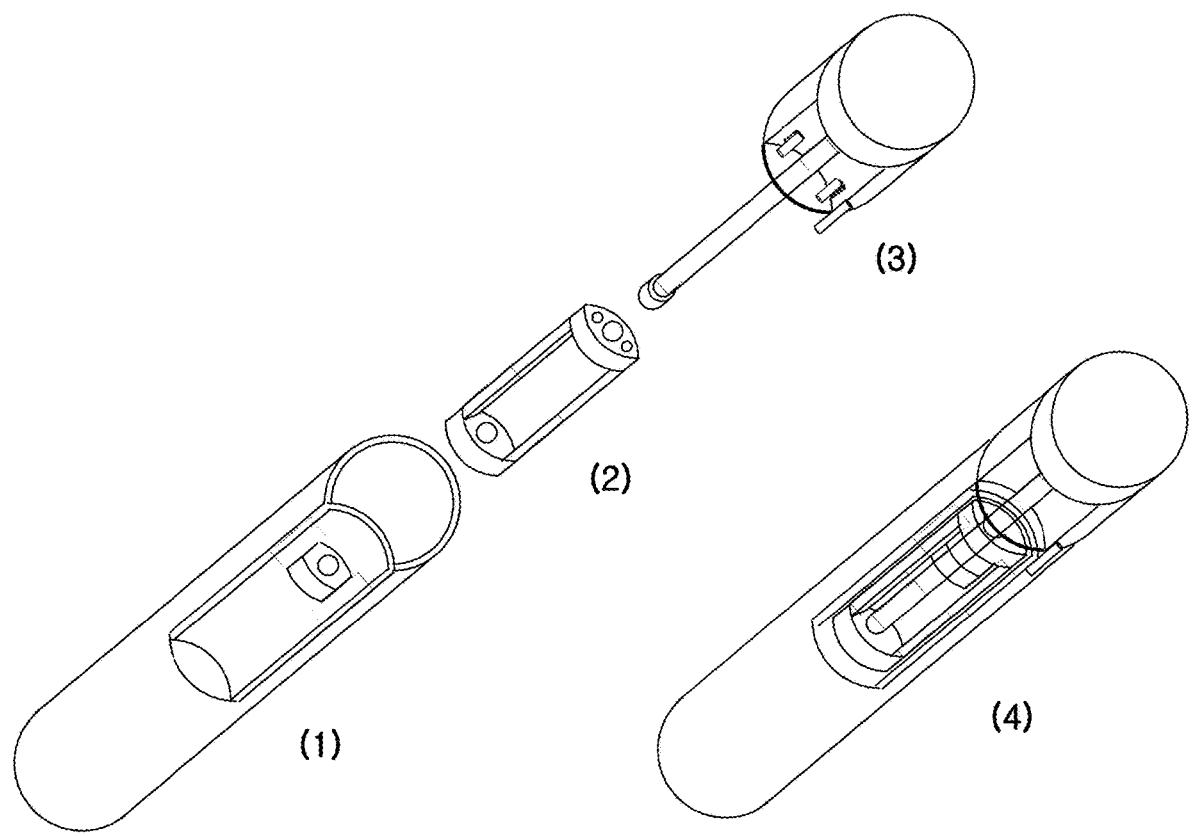
Figure 26:
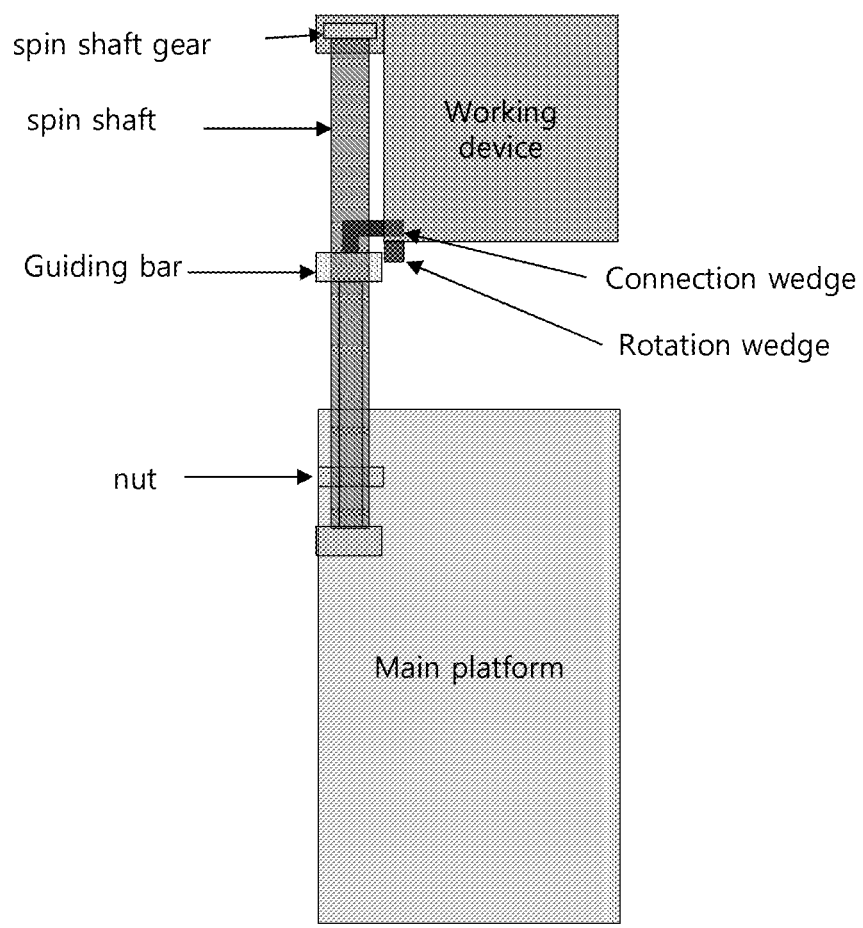

FIGS. 25 and 26 illustrate a case where the moving systems are complexly formed in the main platform and the working devices. The fixing nut and a space into which the guiding bar and the spin shaft are inserted are formed in the recessed region of the main platform. The rotational wedge and the connection wedge are formed in the working device, and the spin shaft tip is formed at an end of the spin shaft of the working device. FIG. 25 illustrates (1) the outer shape of the main platform, (2) the guiding bar, (3) the working device (the rotational wedge, the connection wedge, the spin shaft, and the spin shaft tip are formed), and (4) a form obtained by combining (1), (2), and (3).

FIG. 26 is a side view of (4) of FIG. 25. The spin shaft is coupled to the spin shaft gear, is rotatably and fixedly installed in the working device, and is rotated by the diving device (not illustrated) installed in the working device.

Figure 27:
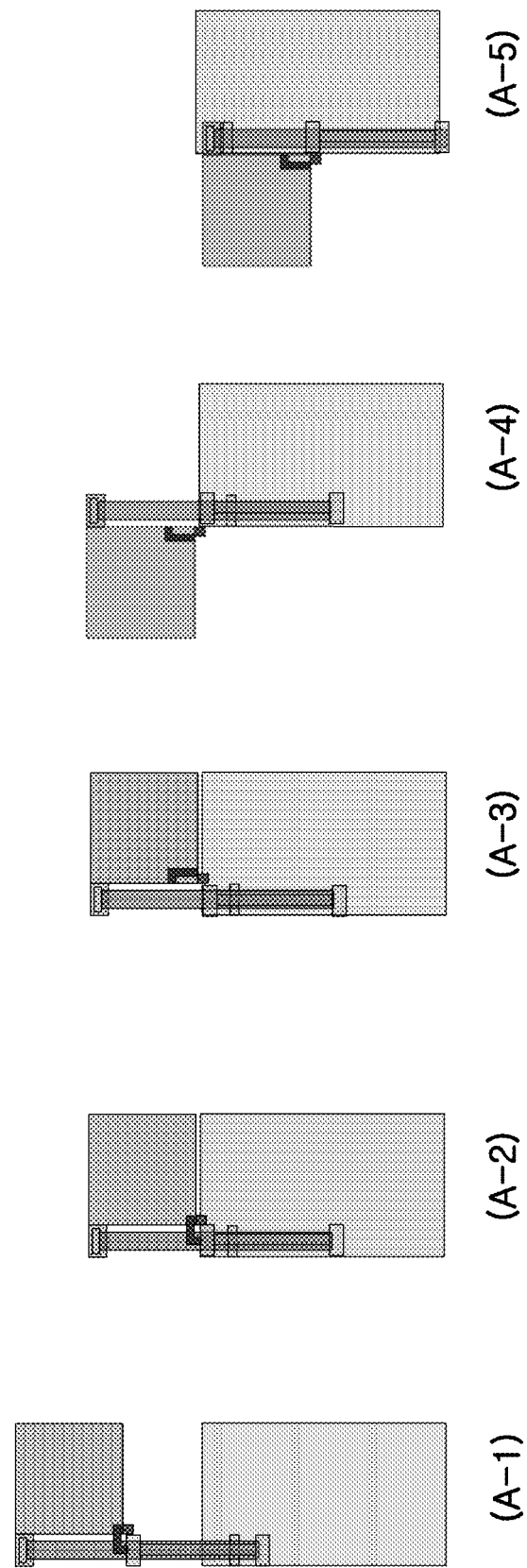

FIG. 27 schematically illustrates driving of the working devices when the moving systems of the working devices are complexly formed in the main platform and the working devices. (A-1) to (A-2) are views which illustrate that the working device moves forward and backward at the tip end of the main platform as the spin shaft is rotated, and illustrate that the working device, the spin shaft, the guiding bar, and the connection wedge are moved together while being engaged with each other. The guiding bar performs the linear motion while disturbing rotational force of the spin shaft, and the connection wedge serves to mechanically couple the guiding bar and the working device to each other such that the working device is not rotated arbitrarily. Accordingly, the working device may perform the forward motion and the backward motion without the rotational motion. (A-3) illustrates that the connection wedge is separated from the guiding bar in order to mount the working device to the outer peripheral surface of the main platform. Accordingly, the spin shaft can perform the rotational motion. (A-4) illustrates that when the working device is rotated by 180 degrees, the rotation wedge comes into contact with the outer peripheral surface of the main platform so that the rotation is terminated. The screw motion of the spin shaft is converted into the linear motion again so that the working device moves backward along the mounting part of the main platform while being rotated by 180 degrees. When the working device moves backward and reaches a position of (A-5), the working device is completely mounted to the outer peripheral surface of the main platform. Thereafter, the working device is retrieved in a reverse order of (A-1) to (A-5).

Figure 28:
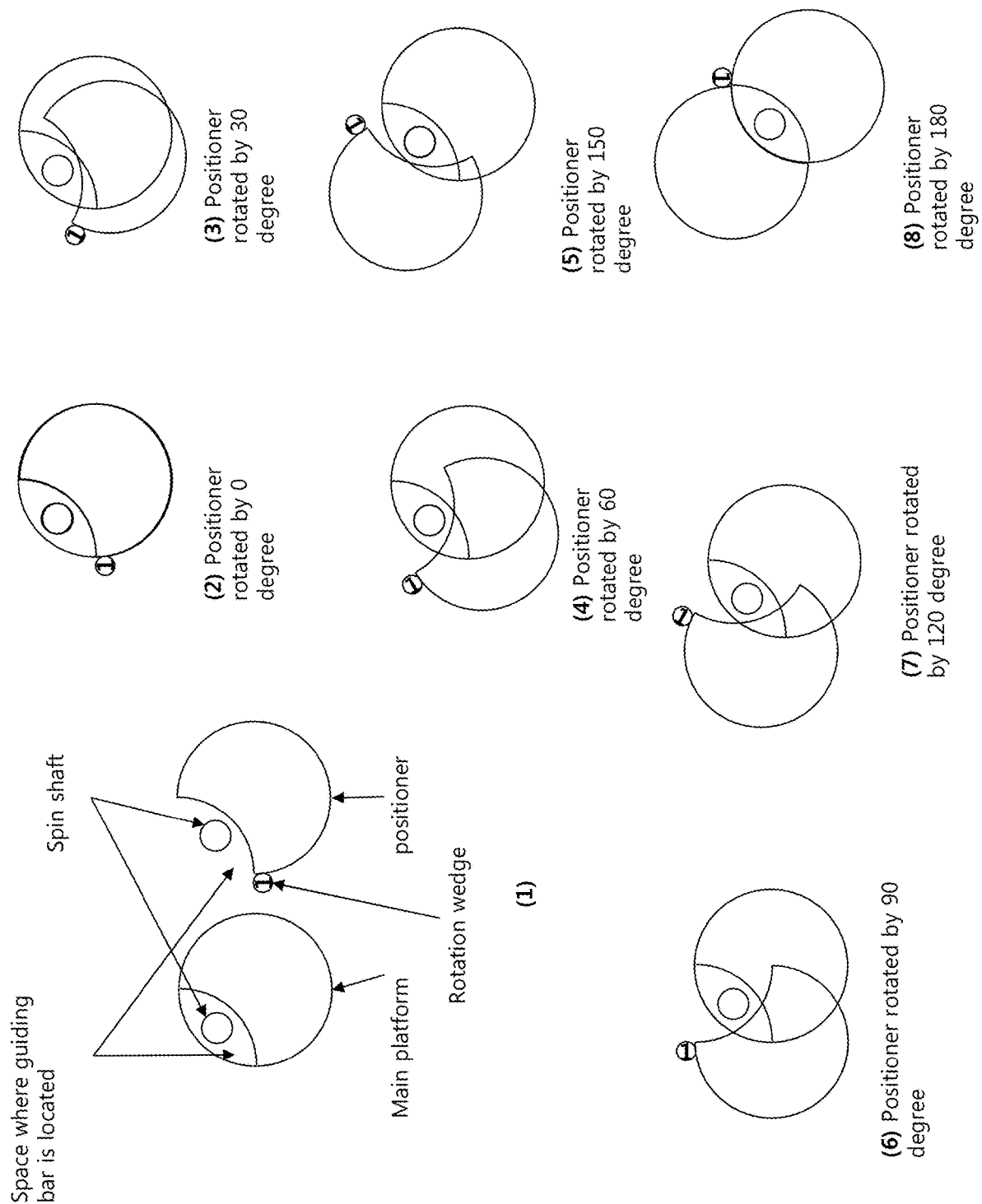

FIG. 28 is a schematic plan view illustrating a mechanism for adjusting a rotational angle by a rotation wedge. The rotation wedge may be formed on one side of the positioner, which is in contact with the outer peripheral surface of the main platform. The height of the rotation wedge is minimized, so that when the positioner is rotated, another structure is affected or obstructed. (2) is a view illustrating a state before the rotation, and (3) to (8) are views when a change in a position of the positioner (blue color) is viewed from above. The positioner is rotated about the spin shaft in a clockwise direction. When the positioner is rotated by 180 degrees, the rotation wedge is caught by the outer wall of the main platform, and the positioner stops the rotating. The above mechanism is applied even to the working devices.

Figure 29:
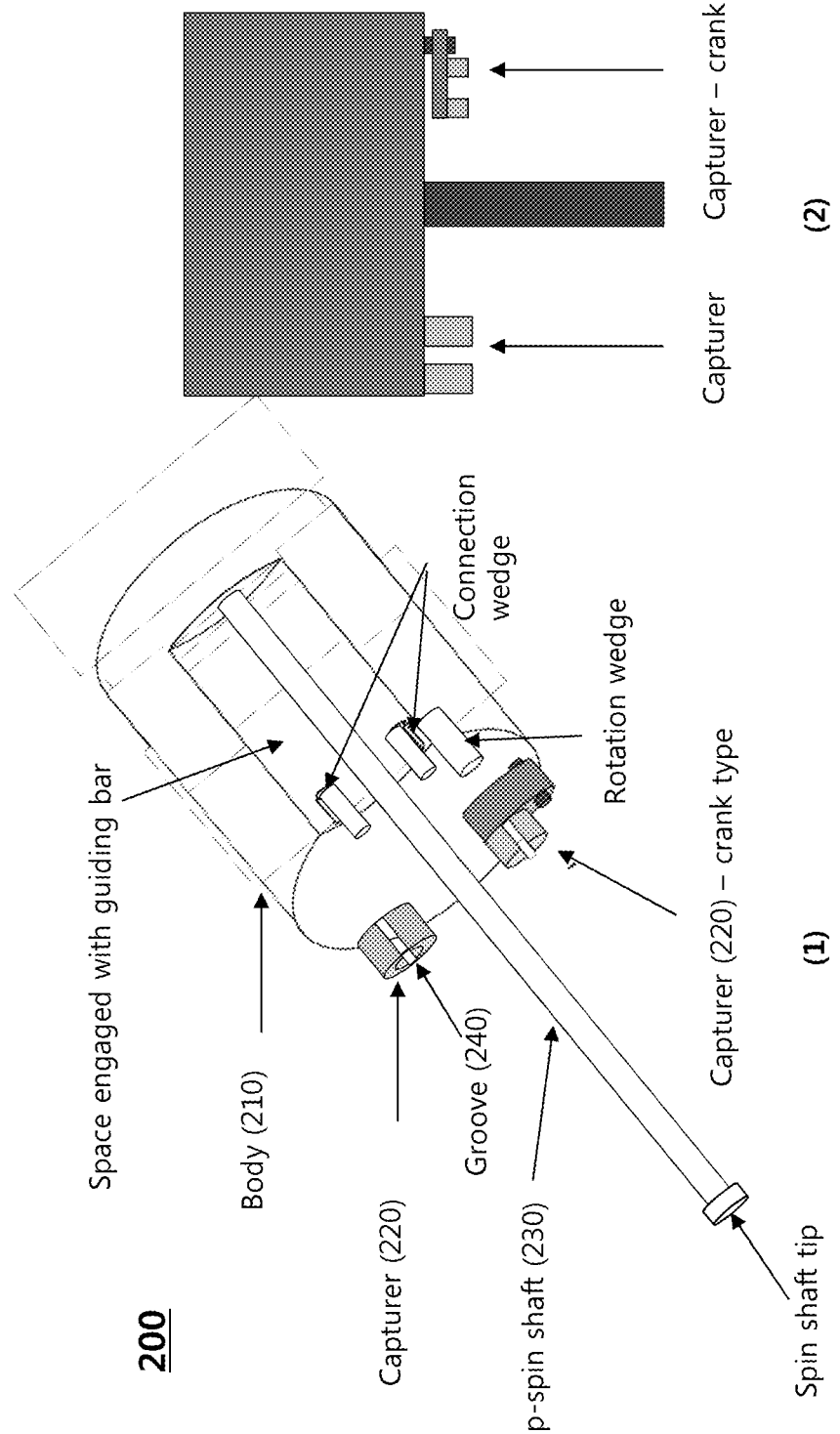

FIG. 29 illustrates a three-dimensional view and a front view of the positioner of the present invention. The P spin shaft, the connection wedge, the rotation wedge, and the capturer are coupled to the positioner. The capturer may generally have a cylindrical shape, but may have a link type or a crank type which is capable of rotational motion, as illustrated in FIG. 29. The capturer is coupled to the coupling boss formed on the upper surface of each of the working devices. Although not illustrated in the drawing, the T spin shaft is coupled to the upper portion of the capturer.

Figure 30:
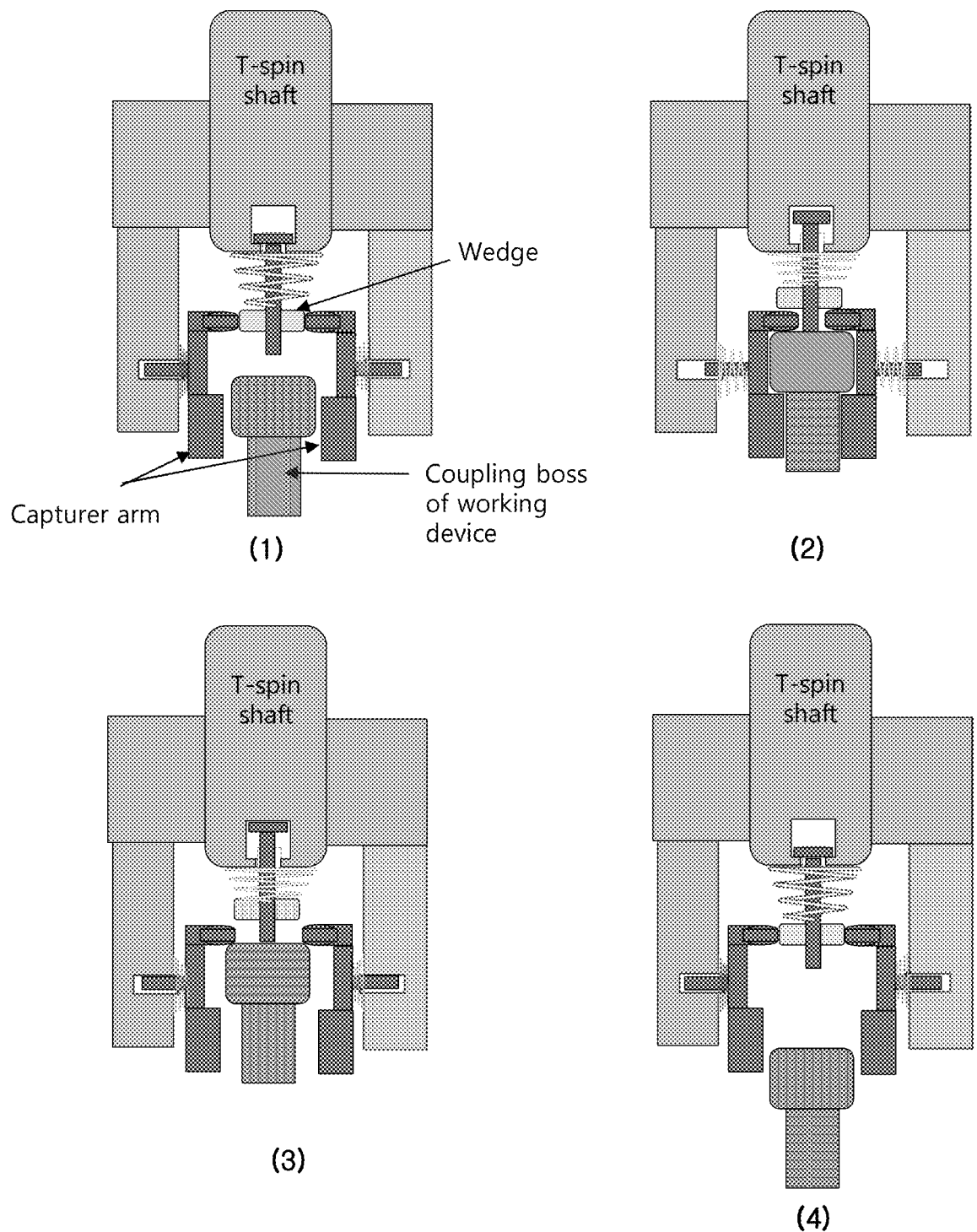

FIG. 30 schematically illustrates an operation order of the capturer unit.

Figure 31A:
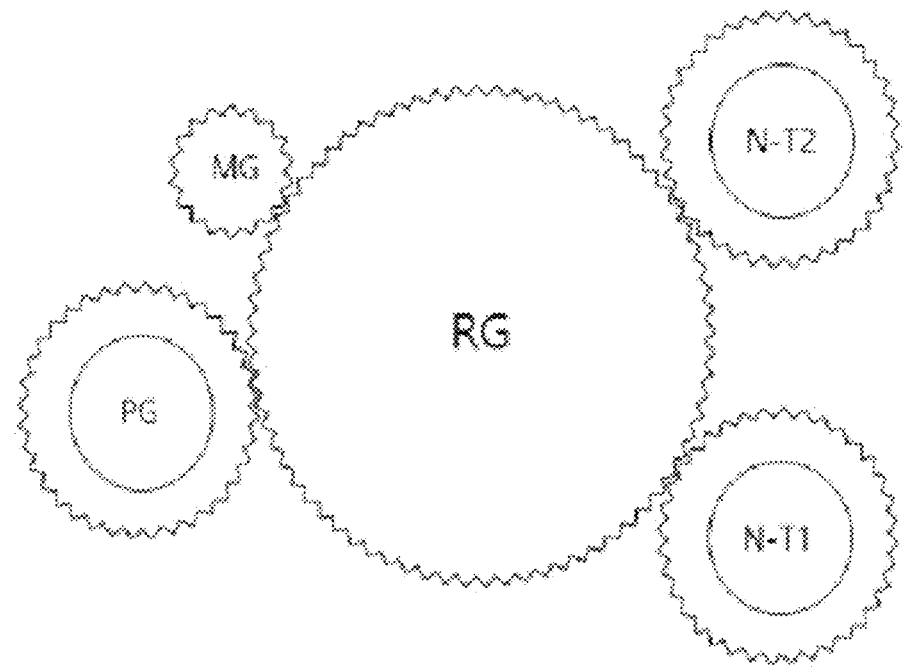
Figure 31B:
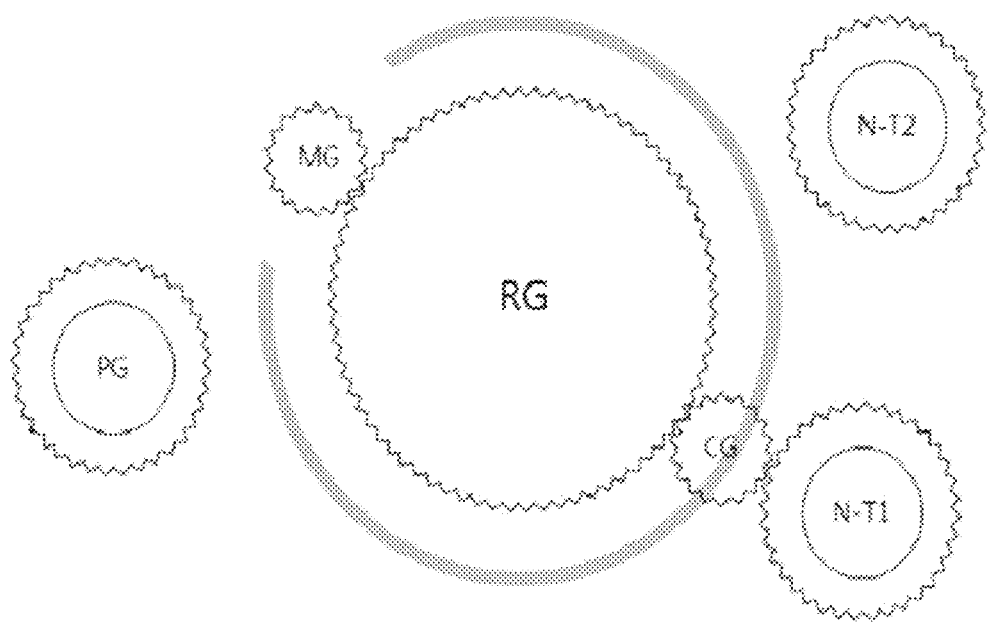

FIG. 31 is a schematic plan view illustrating positions of gears when a motor or a gear is additionally mounted in order to transfer power to the spin shaft, wherein these components transfer driving force to the spin shaft or the driving nut coupled to the spin shaft. The CG moves along a blue curved line, and is engaged with the driving gear (N-T1 or N-T2; and gear formed in driving nut of moving system for position control of each working device) so as to move a desired apparatus. The driving force can be transferred to the working devices, the positioner, or the spin shafts by using motors, the number of which is minimal, without mounting the respective working devices to the motor, by combining various gears. The gears of the spin shaft are connected to the CG of the driving motor (see FIG. 31B) or can perform a screw motion by driving the nut itself (see FIG. 31A). Although it is illustrated that the respective gears are located on one plane, the respective gears may be located substantially at different heights. For example, when a deceleration gear and a motor gear are located at the same height, and a positioner gear and a transfer system gear are located at different heights and are then located at the same height as for the deceleration gear, the gears receive power while being engaged with each other. PG (Positioner Gear): a gear of a spin shaft of a positioner, MG (motor gear): motor gear, RG (reducing gear): deceleration gear, CG (connecting gear): connection gear, and N-T1 and N-T2 (Nut-transfer 1, Nut-transfer 2): driving nuts of transfer systems of first and second working devices.

Figure 32:
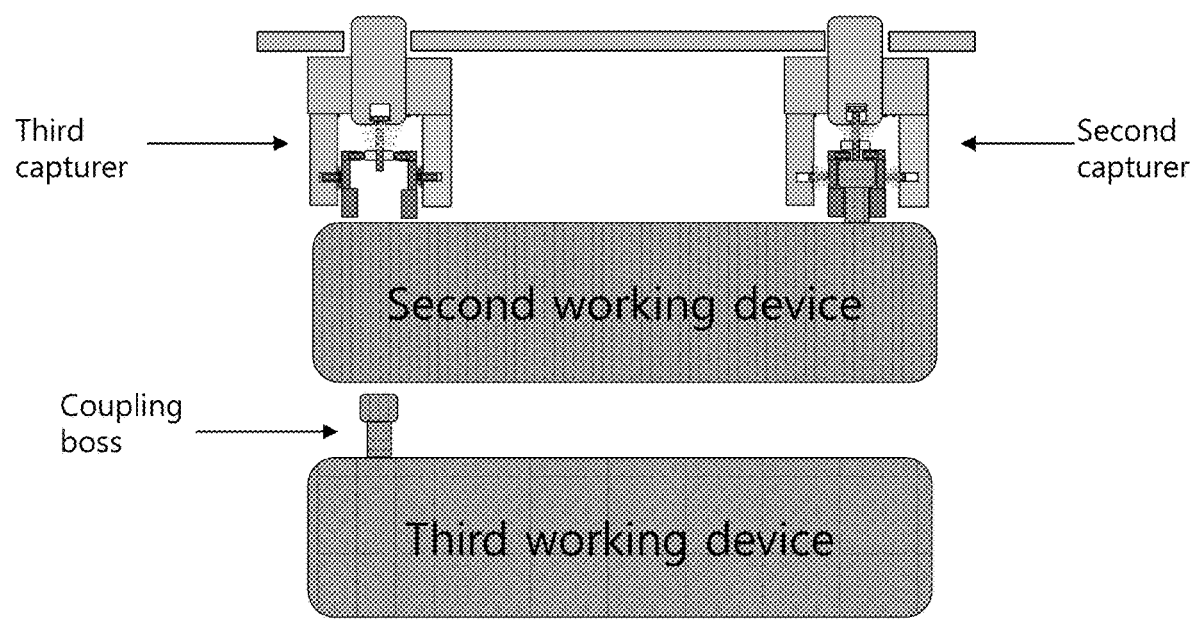

FIG. 32 illustrates a state in which the second working device and the second capturer unit of the positioner are coupled to each other. A method for selectively coupling the working device to the capturer unit is determined on the basis of the positions of the coupling boss of the working device and the capturer unit.

Figure 33A:
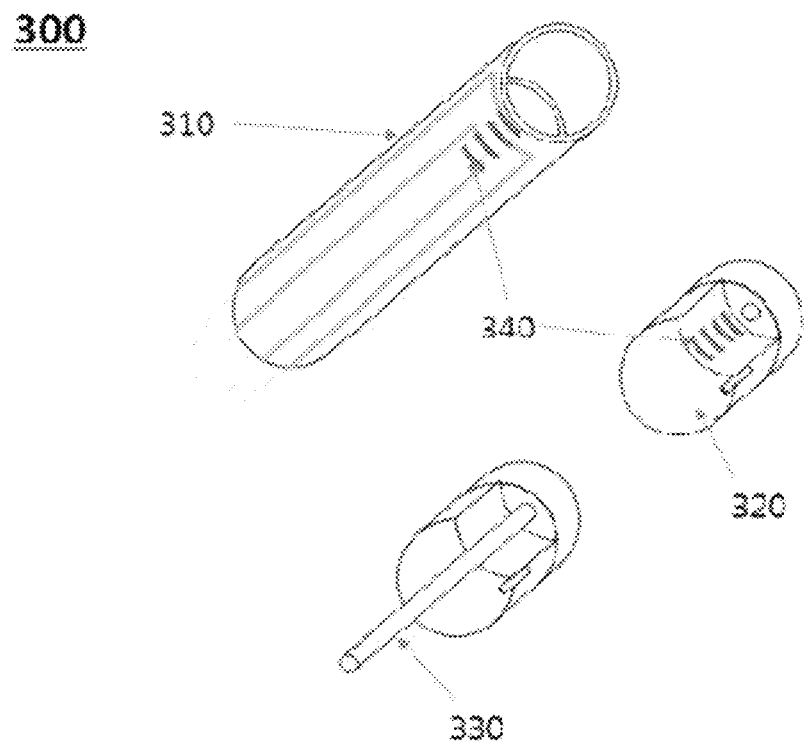
Figure 33B:
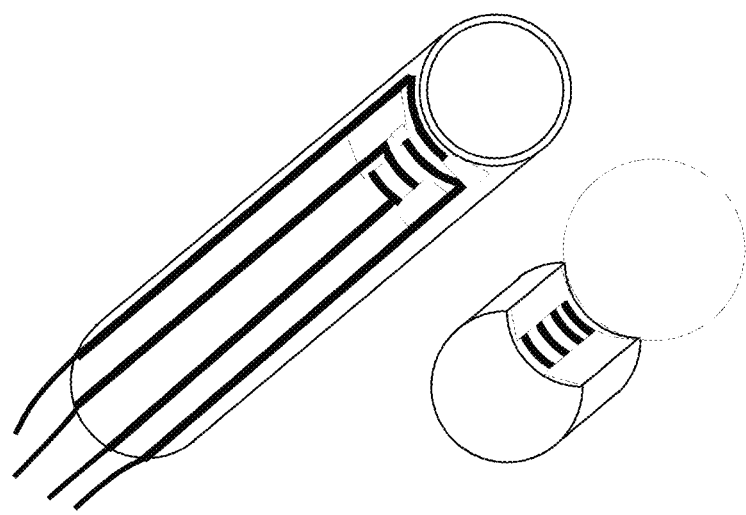

FIGS. 33A, 33B, and 33C schematically illustrate an apparatus in which an electrical connection terminal is formed. A yellow line, which is the inside of the outer wall of the main platform, may be coated with a recessed or insulating body, and a red line is exposed to the outside. A conductor for transferring an electrical signal are formed outside the main platform so as to transfer an external electrical signal to the working device, and an electrical connection terminal are formed at a portion in close contact with the working device so as to transfer an electrical signal to the working device. FIG. 33A illustrates the electrical connection terminal when the working device having the spin shaft is located at the tip end of the main platform. The conductor for transferring an electrical signal can be inserted into the outside of the main platform so as to transfer an external electrical signal and transfer an electrical signal to the portion in close contact with the working device. FIG. 33B illustrates an example where the working device not having the spin shaft is located inside the main platform. FIG. 33C illustrates an example where the working device having the spin shaft is located inside the main platform.

Figure 34:
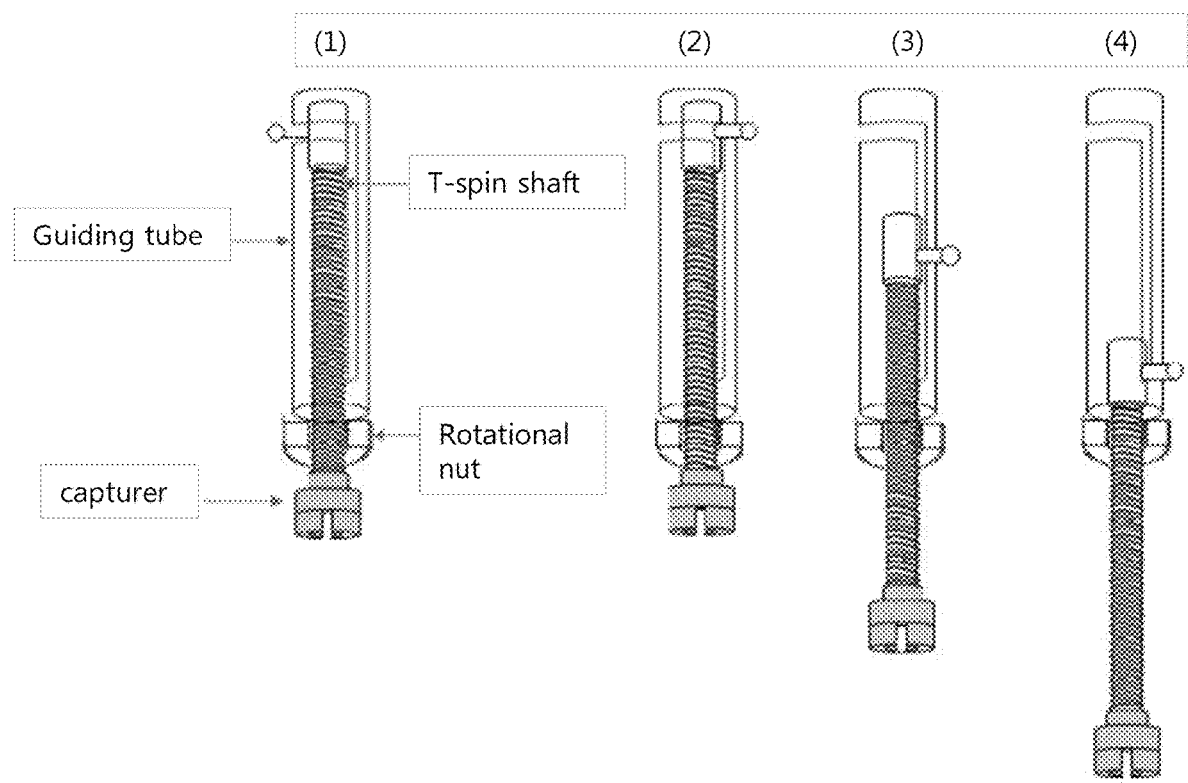

FIG. 34 illustrates a transfer unit for transferring a passive device and a driving form thereof. The transfer unit includes a guiding tube in which a guiding groove is formed, a passive device transfer spin shaft (T spin shaft) in which a guiding boss is formed, a driving nut, and a capturer.

Figure 35:
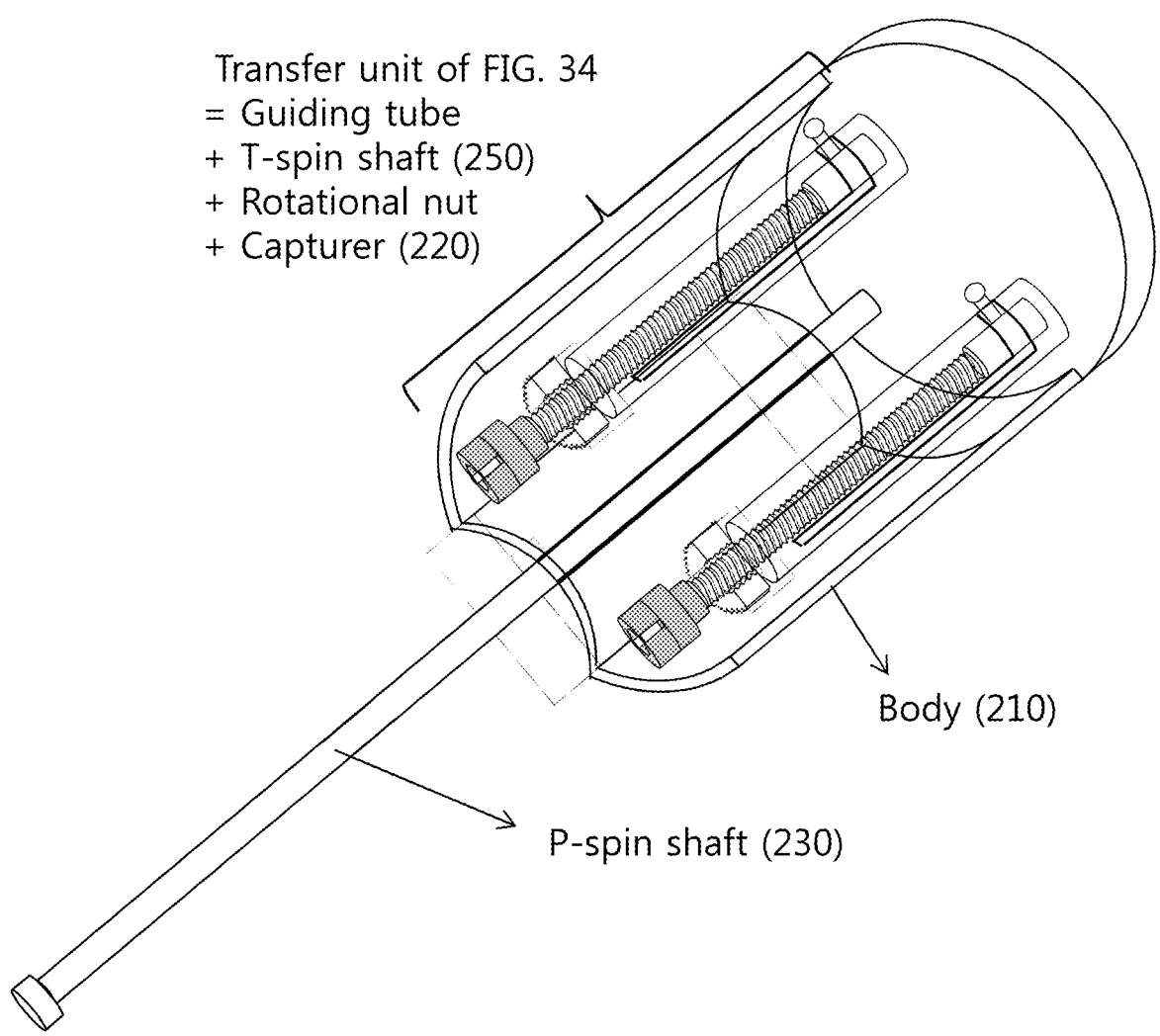

FIG. 35 illustrates an example of the position control apparatus 200 having a fixed transfer unit therein (transfer unit of FIG. 34). The position control apparatus 200 is an apparatus for transferring a passive working device having a spin shaft.

Figure 36:
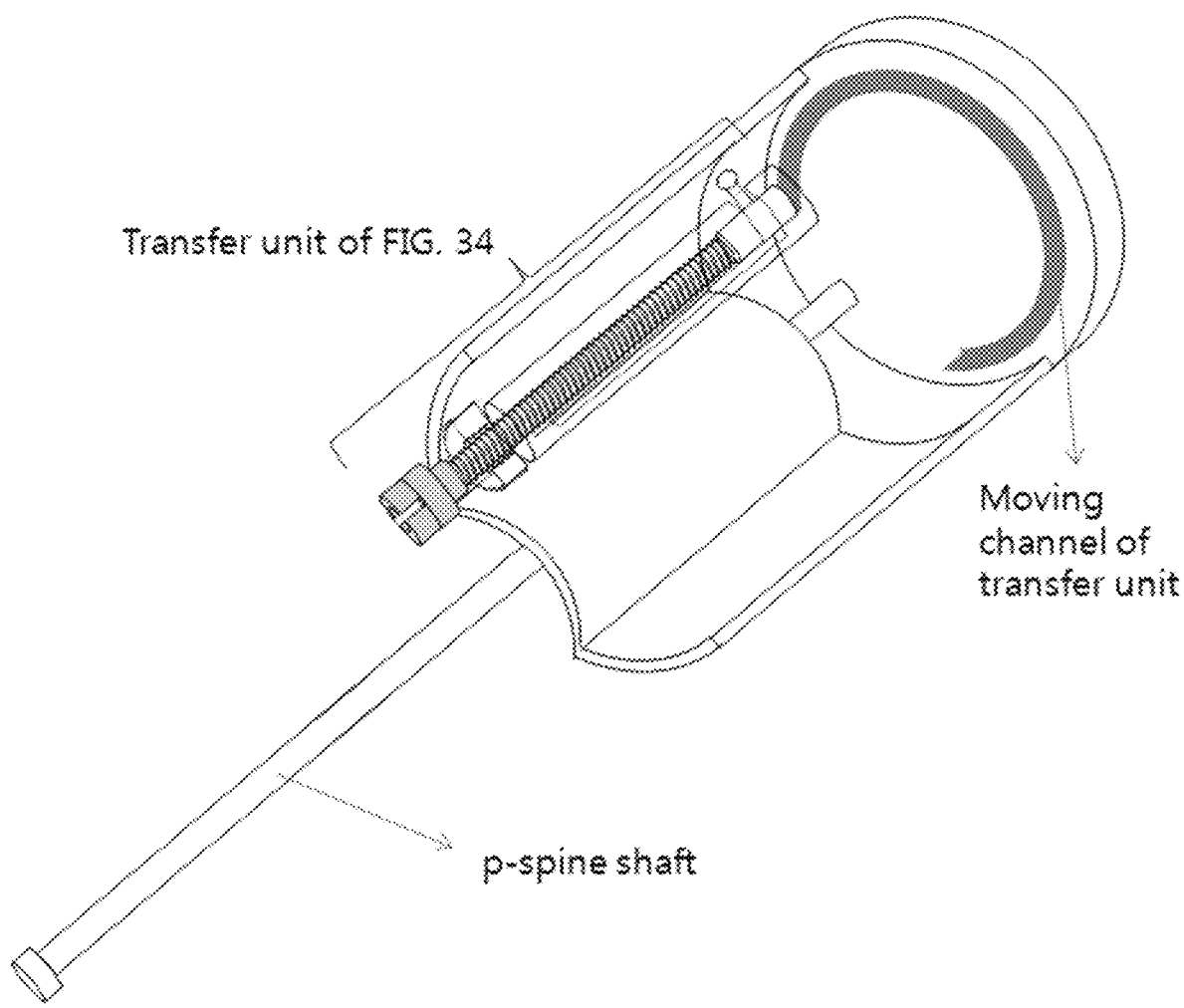

FIG. 36 illustrates an example of the position control apparatus 200 having a movable transfer unit therein (transfer unit of FIG. 34). The transfer unit is connected and coupled to the rotary shaft formed in the body so as to move along a circular arc (blue line), and couples the working device and the capturer to each other at respective positions so as to change the position of the working device.

Figure 37:
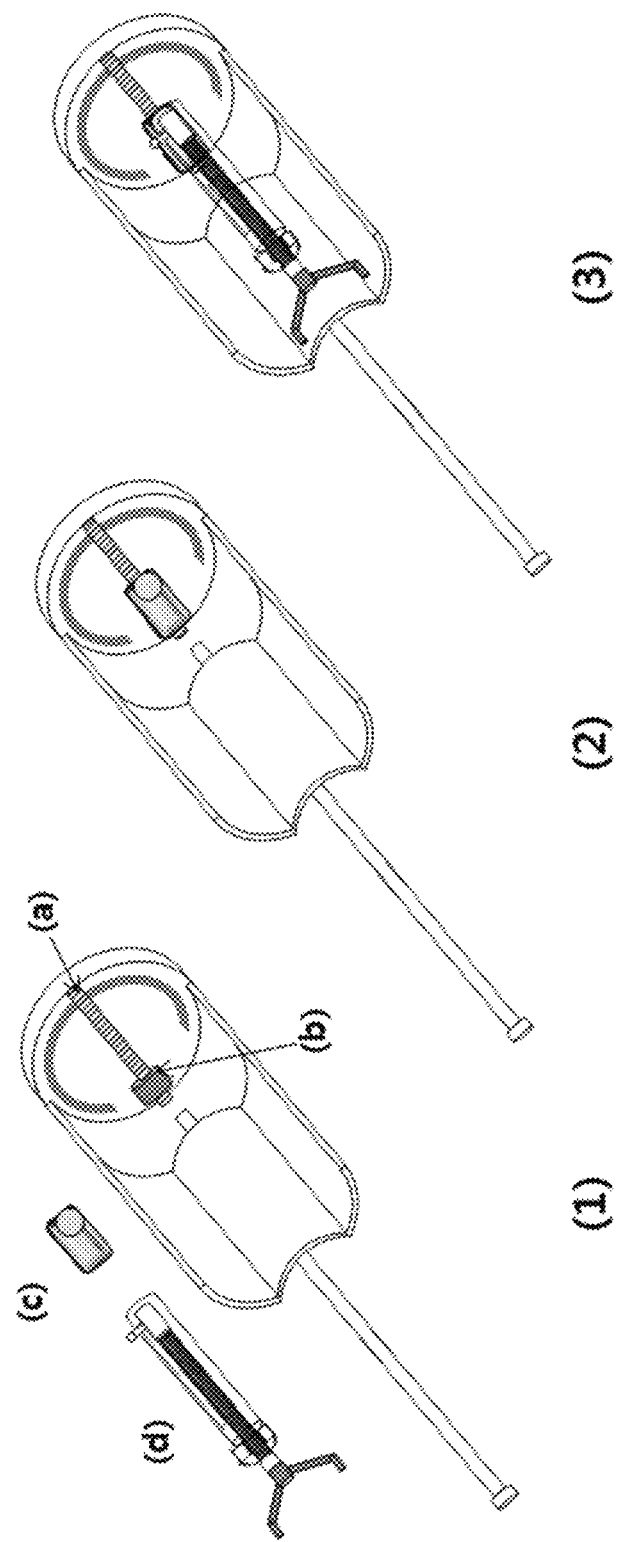

FIG. 37 illustrates a state in which a horizontal shaft (a) having a screw installed therein and a transfer nut (b) engaged with the horizontal shaft are installed inside the position control apparatus 200, wherein the horizontal shaft (a) is connected to the driving device (not illustrated), and is connected to the rotary shaft (not illustrated) installed in the position control apparatus. A blue circular arc indicates an arc through which the horizontal shaft may pass while rotating about the rotary shaft. Approximately, the recessed portion in the position control apparatus is an arc shape removed from a circle. (2) A form in which the connection member (c) is installed; the transfer unit is coupled to a sky-blue circular position at an end of the connection member, and the transfer nut is coupled to an opposite surface of the other end. Further, (3) a form in which the transfer unit (d) is installed; the transfer unit is coupled to the end of the connection member such that the longitudinal axis of the horizontal shaft is perpendicular to the longitudinal axis of the transfer unit.

Figure 38:
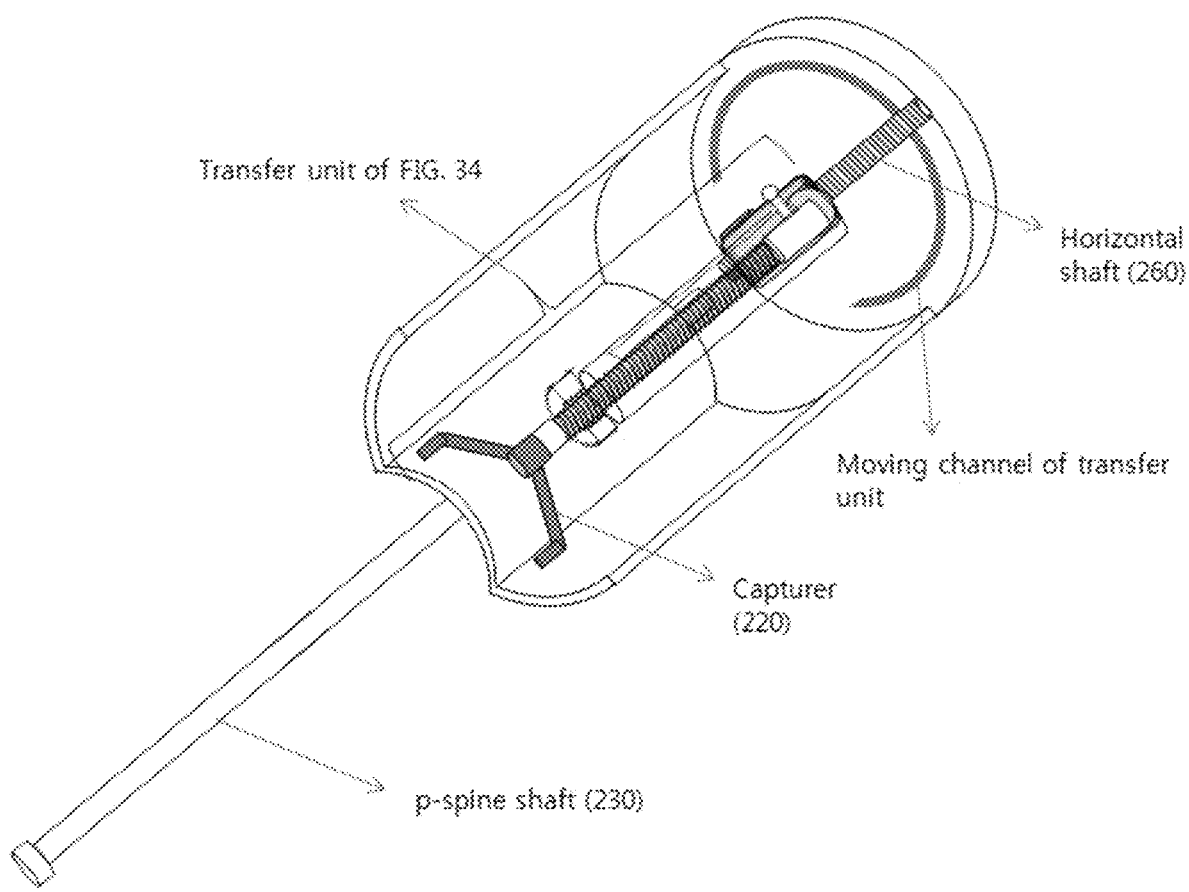

FIG. 38 is an enlarged view of (3) of FIG. 37, and the difference between the forms of the capturers of FIGS. 37 and 38 and the form of FIG. 36 indicates that the capturer has a proper form in accordance with the form of a device.

Figure 39:
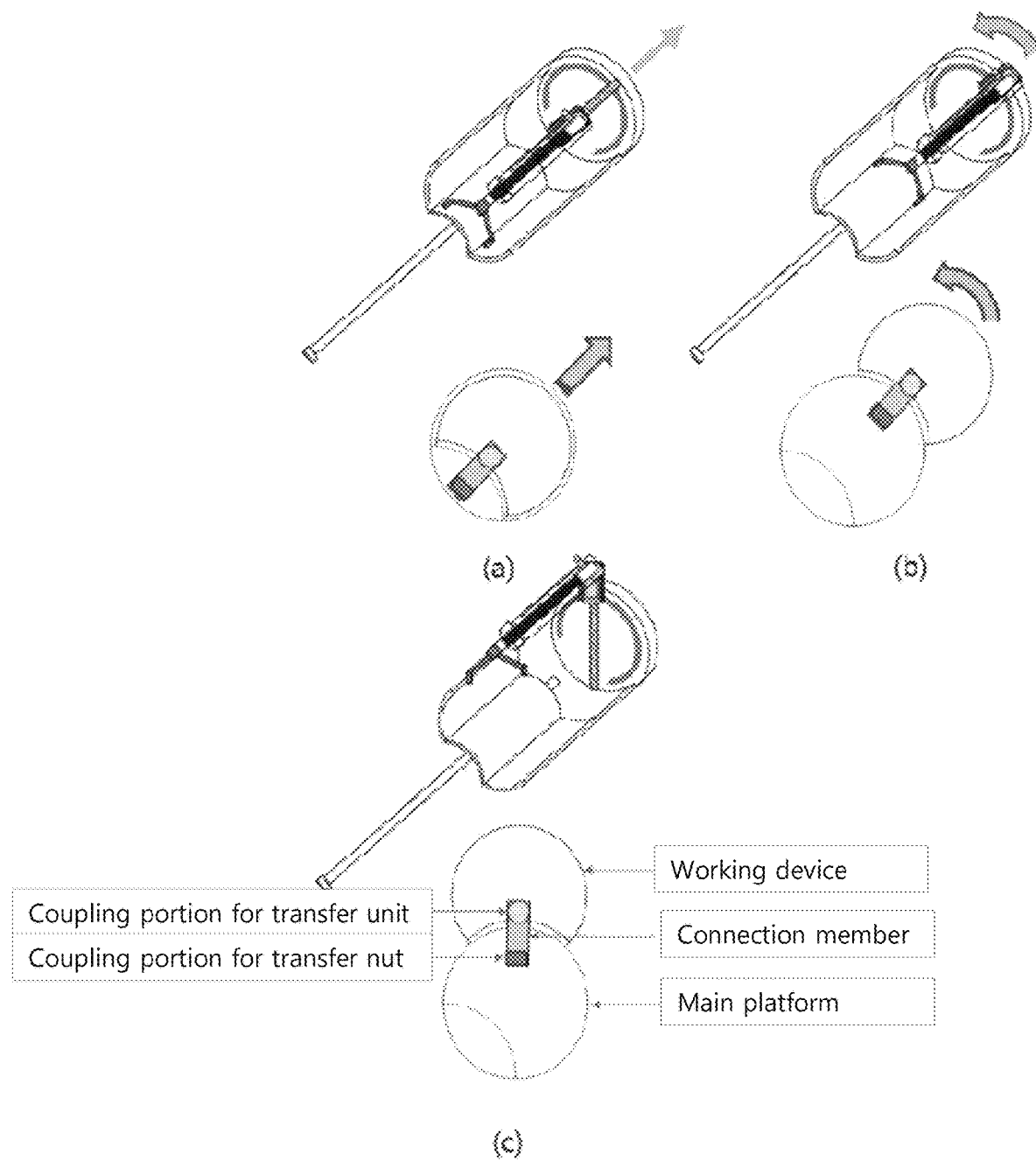

FIG. 39 illustrates a three-dimensional view of the position control apparatus to which the movable transfer unit having the horizontal shaft installed therein is mounted, and positions of the working device, the connection member installed in the transfer nut of the position control apparatus, and the main platform in the trans-platform apparatus having the position control apparatus installed therein when viewed from the horizontal axis, while the three-dimensional view and the positions overlap each other. A position where the transfer unit is coupled to the connection member and a position where the transfer nut is coupled are displayed so as to help three-dimensional understanding. (1) is an initial state in which the position control apparatus and the working device are coupled to each other. In this state, the working device within the main platform is lifted up and is moved to the outside of the main platform. Here, a coupling portion of the transfer nut of the connection member is shifted to one side of the position control apparatus, and a coupling portion of the transfer unit is located a little more inside, so that the transfer nut and the transfer unit do not overlap the guiding bar of the position control apparatus. (2) illustrates a state in which the transfer nut moves in an arrow direction of view (1) and reaches an end of the horizontal shaft. The coupling portion of the transfer unit of the connection member connected to the transfer nut moves outside the cross section of the main platform. That is, the transfer unit moves to the outside of the position control apparatus, and when it is rotated about the rotary shaft, is not caught by the position control apparatus. (3) is a result of rotating the transfer unit in an arrow direction of view (2). The rotation of the transfer unit occurs by rotating the rotary shaft connected to the horizontal shaft using the central axis of the main platform as a center. As a result of the rotation, the working device moves to a position to be mounted to the main platform. Thereafter, the working device is mounted to the main platform through a downward linear motion of the transfer unit. When the working device is removed from the main platform, the removal is possible by performing the above-described process in a reverse order.

Figure 40:
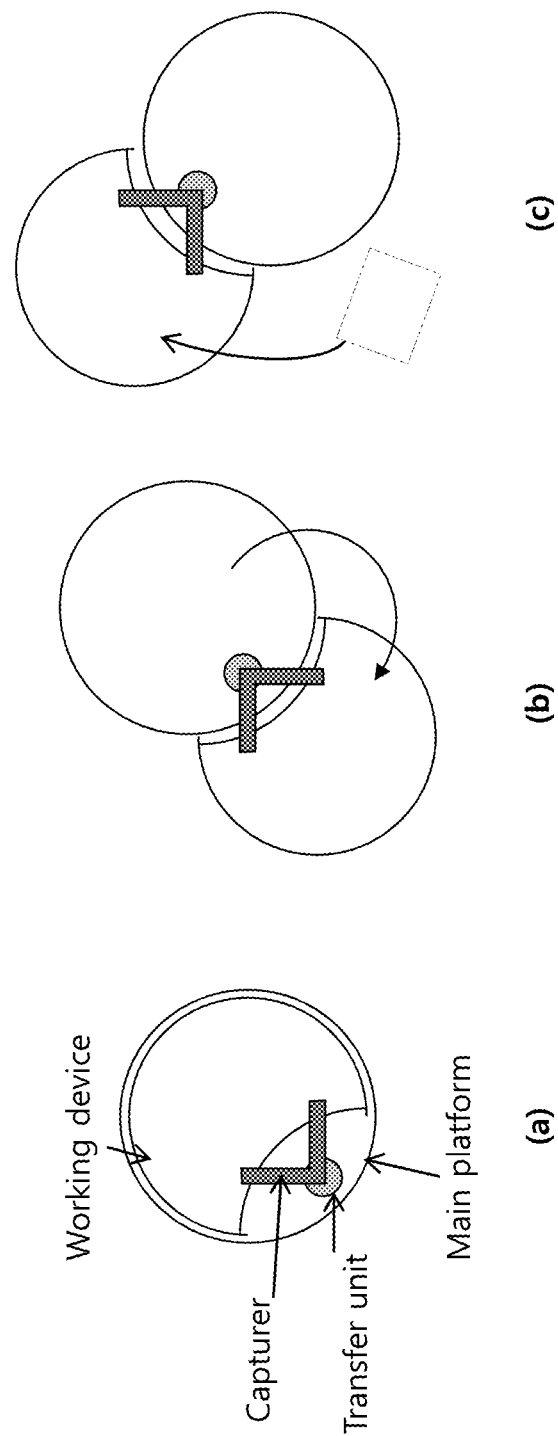

FIG. 40 is a plan view illustrating that the position control apparatus performs a position control below the working device when viewed from the horizontal direction, when the position control apparatus and the working device not having the spin shaft are located inside the main platform. The position control apparatus has the transfer unit formed on one side thereof, which can perform vertical motion, and the transfer unit is connected and coupled to the rotary shaft installed in the position control apparatus. (a) In a state in which the working device and the transfer unit are coupled to each other, the body of the position control apparatus is covered by the working device and is thus not viewed. In this state, the working device is moved forward, and is thus moved to the outside of the main platform (blue circle: main platform, red figure: working device, yellow circle: transfer unit, and blue figure: capturer); (b) in a state in which the transfer unit is rotated by 180 degrees, when the transfer unit is rotated about the central axis of the main platform, the mounting surface of the working device is located to be always in close contact with the mounting surface of the main platform; and (c) in a state in which the rotary shaft to which the transfer unit is connected is rotated by a predetermined angle (90 degrees), the mounting surface of the working device and the mounting surface of the main platform are located on the same horizontal axis. At this time, the center of the rotation is the central axis of the main platform. Thereafter, the transfer unit is moved backward so that the working device is mounted to the main platform. Even when the rotary shaft is rotated by any angle as well as 90 degrees, the transfer unit is moved backward toward the main platform and is thus at a mountable position, so that the working device can be mounted at a proper position.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

Embodiment

Embodiment 1: Manufacturing of Endoscopic Apparatus

An endoscopic apparatus of the present invention, which is an approximately tube-shaped flexible endoscopy, includes: a main tube 110 inserted into a human body of a patient, which is a working space; and a working device 120 which can be mounted to the tip end of the main tube, and can be rotated by a spin shaft 130. The working device includes the spin shaft 130 which is a connection means for connecting the main tube and the working device to each other, is inserted and installed inside the main tube and the working device, and operates as a rotary shaft of the working device.

The endoscopic apparatus is manufactured such that the cross-section of the main tube and the cross-section of the working device coincide with each other, and a plurality of working devices are mounted to the tip end of the main tube as illustrated in FIGS. 4 to 6. The working device has an approximately cylindrical shape such that the cross-section thereof coincides with the cross-section of the main tube. When there are a plurality of working devices, a space where spin shafts can be rotated should be formed. As illustrated in FIG. 14, in order to properly spatially arrange the respective working devices when reaching a final state for work, working devices except for the foremost working device are manufactured to have not a completely cylindrical shape but a cylindrical shape having a concave groove formed on the side surface thereof (see FIG. 2).

A camera, an ultrasonic wave probe, a robot arm, a surgical apparatus, or a surgical auxiliary apparatus may be mounted and used as the working device, and these components are coupled to the main tube through the spin shafts. An approximately cylindrical hole is formed at the tip end of the main platform such that the spin shaft can be insert-coupled thereto, and the spin shaft mounted to the working device is insert-coupled to such a hole. The size and the shape of the hole formed at the tip end of the main platform may be changed according to the length and the shape of the spin shaft, and the spin shaft may be manufactured to be changeable according to use of the working device, a power transmission method to the working device, an arrangement order of the working devices, and the like. For example, the length of the spin shaft can be adjusted variously in accordance with use thereof.

The spin shaft is formed on one side of the outside of the working device, can be rotated by 180 degrees, and is manufactured to be inserted and mounted to the outside of the main tube. Further, the flexibility of the spin shaft may be partially differently configured. For example, a portion thereof inserted into the main tube is configured by a hard portion, and a portion thereof coupled to the working device may be configured by a soft portion. Since the spin shaft should be manufactured to be capable of forward motion, backward motion, and rotational motion, the portion inserted into the main tube may be configured by a hard portion which makes driving relatively easy.

Meanwhile, although the spin shaft may have a smooth cylindrical shape, a screw groove or a position fixing protrusion wedge may be formed on the outer peripheral surface of the spin shaft according to the use of the working device and the driving apparatus of the spin shaft.

The endoscopic apparatus of the present invention may additionally include a positioner 140 which mounts the working device to the main tube (see FIG. 29). The positioner serves to mount the working device to the main tube by performing reciprocating motion including forward motion and rearward motion, and rotational motion, and may be installed at the tip end of the main tube or may be installed inside the main tube. When the positioner is installed inside the main tube, the working device located inside the main tube is rotated and is thus mounted to a predetermined position. In order to drive the positioner, a power transmission apparatus may be connected.

Embodiment 2: Manufacturing of Trans-platform Apparatus to which Positioner is Mounted The positioner of the present invention is a position control apparatus which performs vertical reciprocating motion and rotational motion or crank-rotational motion so as to mount the working device coupled to the positioner to a specific position. The positioner may be described as the position control apparatus 200 for controlling positions of working devices longitudinally connected to each other (see FIG. 29). The positioner may include: (a) a cylindrical body 210 which can be mounted to an upper portion of one of the working devices longitudinally connected to each other; and (b) a capturer 220 which is formed at a lower portion of the body 201 and connects the working device and the body to each other; and a spin shaft which operates as a linkage axis of the working device.

The capturer is coupled to the spin shaft mounted inside the body 201, a groove 240, which can be coupled to a coupling boss of the working device, is formed inside the capturer, and the spin shaft is mounted inside the body 201 and is moved outside the body together with the capturer 220, thereby adjusting the position of the working device. The spin shaft is located in the guiding tube installed inside the positioner, and is coupled to the driving nut.

The positioner may include one or more capturers or a plurality of spin shafts, and the capturers may be formed to be shifted to one side of the body. The positioner of the present invention can control positions of working devices longitudinally connected to each other, such as a camera, a light source, an ultrasonic wave probe, a robot arm, a position adjustment device, a surgical device, and a surgical auxiliary device.

The spin shaft (see (1) of FIG. 29) coupled to the outside of the positioner or the spin shaft coupled to the inside of the positioner is configured by a soft portion, a hard portion, or a soft portion and a hard portion, as needed.

Hereinabove, a particular portion of the present invention has been described in detail. It is obvious to those skilled in the art that such a detailed description is merely one embodiment, and does not limit the scope of the present invention. Thus, the substantial scope of the present invention is defined by appended claims and equivalents thereof.

DESCRIPTION OF REFERENCE NUMERALS

100: Trans-platform apparatus
110: Main platform
120: Working device
130: Spin shaft
140: Spin shaft hole
150: Spin shaft hole to which additional working device can be mounted
200: Position control apparatus
210: Body
220: Capturer
230: P-spin shaft
240: Groove
250: T-spin shaft
300: Trans-platform apparatus
310: Main platform
320: Working device
330: Spin shaft
340: Electrical connection terminal

The invention claimed is:

1. A trans-platform apparatus (100) comprising:
   (a) a cylindrical main platform (110) for insertion into a working space;
   (b) a cylindrical working device (120) inserted into a tip end or a central portion of the main platform; and
   (c) a positioner that (i) performs vertical motion and rotational motion, (ii) controls the position of the working device, and (iii) comprises a spin shaft and a connection wedge,
   wherein the working device can be mounted to an outside of the main platform through rotational motion or linear motion.

2. The trans-platform apparatus of claim 1, wherein an outline of a cross-section of the main platform and an outline of a cross-section of the working device coincide with each other.

3. The trans-platform apparatus of claim 2, wherein the cross-section is a circle, an ellipse, or a polygon.

4. The trans-platform apparatus of claim 1, wherein the trans-platform apparatus comprises one or more working devices.

5. The trans-platform apparatus of claim 4, wherein the working devices are longitudinally connected to the main platform.

6. The trans-platform apparatus of claim 1, wherein the trans-platform apparatus comprises: (i) a recessed region on an outer peripheral surface of the main platform, the working device being mounted to the recessed region; or (ii) a recessed region on an outer peripheral surface of the working device such that the working device is mounted to the outside of the main platform.

7. The trans-platform apparatus of claim 6, wherein the trans-platform apparatus comprises electrical connection terminals formed on contact surfaces of the main platform and the working device.

8. The trans-platform apparatus of claim 1, wherein the working device additionally comprises a rotation wedge or a connection wedge.

9. The trans-platform apparatus of claim 1, wherein the working device is a camera, a light source, an ultrasonic wave probe, a robot arm, a position adjustment device, a surgical device, or a surgical auxiliary device.

10. The trans-platform apparatus of claim 1, wherein the trans-platform apparatus additionally comprises a cylindrical cover for covering a tip end or a device of the main platform.

11. The trans-platform apparatus of claim 1, wherein the trans-platform apparatus additionally comprises a working device that is moved into a working space while being mounted inside the main platform, and is mounted to an outer peripheral surface of the main platform.

12. The trans-platform apparatus of claim 11, wherein the trans-platform apparatus has a spin shaft hole (150) formed at a tip end of the main platform, the additional working device being mounted to the spin shaft hole (150).

13. The trans-platform apparatus of claim 1, wherein the positioner is mounted at a tip end or a central portion of the main platform.

14. The trans-platform apparatus of claim 1, wherein the positioner additionally comprises a rotation wedge.

15. The trans-platform apparatus of claim 1, wherein the trans-platform apparatus additionally comprises a moving system of the working device.

16. The trans-platform apparatus of claim 15, wherein the moving system is selected from the group consisting of (i) a spin shaft (130) that is formed on one side of the main platform or the working device, adjusts rotational or linear motion of the working device, and operates as a linkage axis, (ii) a capturer that is formed on one side of the main platform or the working device, and is coupled to the working device, (iii) a linear motion unit or linear motion guiding unit that is formed on one side of the main platform or the working device, and adjusts linear motion of the working device in a horizontal direction of a central axis of the main platform, (iv) a combination thereof.

17. The trans-platform apparatus of claim 16, wherein the spin shaft is insert-coupled or screw-coupled to the main platform.

18. The trans-platform apparatus of claim 16, wherein the spin shaft is configured by a soft portion and a hard portion.

19. The trans-platform apparatus of claim 16, wherein the spin shaft additionally comprises an electric power transmission device, a fluid transmission tube, or a power transmission device.

20. The trans-platform apparatus of claim 16, wherein the trans-platform apparatus has a space and a spin shaft hole formed on an outside of the main platform, the spin shaft capable of rotational motion in the space.

21. The trans-platform apparatus of claim 15, wherein the moving system additionally comprises an element selected from the group consisting of (a) a driving or fixing nut, (b) a cylindrical guiding tube that controls linear or rotational motion of the spin shaft, (c) a guiding bar that comprises an upper cylinder, a lower cylinder and a body for connecting the upper cylinder and the lower cylinder, is mounted to a recessed region formed on an outer peripheral surface of the main platform, and guides linear motion of the working device, (d) a spin shaft, and (e) a combination thereof.

22. The trans-platform apparatus of claim 21, wherein the guiding tube has a guiding groove formed therein.

23. The trans-platform apparatus of claim 21, wherein the guiding bar has an elliptical bottom surface, both ends of which are sharp.

24. The trans-platform apparatus of claim 21, wherein an upper cylinder of the guiding bar has a hole through which the spin shaft coupled to the working device passes, and a lower cylinder of the guiding bar has a groove into which the spin shaft is inserted.

25. The trans-platform apparatus of claim 21, wherein a body of the guiding bar corresponds to two columns that connect the upper and lower cylinders to each other.

26. The trans-platform apparatus of claim 1, wherein the trans-platform apparatus additionally comprises a driving device that enables an operation of the working device.

27. The trans-platform apparatus of claim 26, wherein the driving device is a motor or a gear.

28. A position control apparatus (200) for controlling positions of working devices longitudinally connected to each other at a tip end of or inside a main platform, the position control apparatus comprising:
  (a) a cylindrical body (210) that is mountable to an upper portion or a lower portion of one of the working devices longitudinally connected to each other; and
  (b) a transfer unit that is formed inside the cylindrical body, is connectable to the working devices and is capable of moving positions of the working devices.

29. The position control apparatus of claim 28, wherein the transfer unit is selected from the group consisting of (a) a capturer (200) that connects the working devices and the transfer unit, (b) a rotary shaft that rotates the capturer, (c) a driving shaft for vertical motion of the capturer, (d) a driving or fixing nut, (e) a guiding tube that is a cylindrical tube, and controls linear and rotational motion of a T-spin shaft, (f) a guiding bar that includes an upper cylinder, a lower cylinder, and a body for connecting the upper cylinder and the lower cylinder, is mounted inside a body of a positioner, and guides linear motions of the working devices, (g) the T-spin shaft (250) capable of rotational and vertical reciprocating motion, and (h) a combination thereof.

30. The position control apparatus of claim 29, wherein the capturer is insert-coupled, screw-coupled, ratchet-coupled, rack-pinion-coupled, or magnetic-coupled to the working devices.

31. The position control apparatus of claim 29, wherein the capturer comprises a crank capable of reciprocating or rotational motion.

32. The position control apparatus of claim 28, wherein the transfer unit additionally comprises a linear motion unit or linear guiding unit that adjusts linear motion in a horizontal axis direction of the main platform.

33. The position control apparatus of claim 28, wherein the position control apparatus additionally comprises a moving system of the body (210).

34. The position control apparatus of claim 33, wherein the moving system is selected from the group consisting of (a) a driving or fixing nut, (b) a guiding tube that is a cylindrical tube, and controls linear motion and rotational motion of a spin shaft, (c) a guiding bar that includes an upper cylinder, a lower cylinder, and a body for connecting the upper cylinder and the lower cylinder, is mounted to a recessed region formed on an outer peripheral surface of the main platform, and guides linear motions of the working devices, (d) a P-spin shaft (230) that is mounted to the body (210), adjusts rotational and linear motion of the body, and operates as a linkage axis of the body, and (e) a combination thereof.

35. The position control apparatus of claim 34, wherein the guiding tube has a guiding groove formed therein.

36. The position control apparatus of claim 34, wherein the guiding bar has an elliptical bottom surface, both ends of which are sharp.

37. The position control apparatus of claim 34, wherein an upper cylinder of the guiding bar has a hole through which the spin shaft coupled to a working device can pass, and a lower cylinder of the guiding bar has a groove into which the spin shaft can be inserted.

38. The position control apparatus of claim 34, wherein a body of the guiding bar corresponds to two columns for connecting upper and lower cylinders.

39. The position control apparatus of claim 29, wherein the spin shaft is configured by a soft portion and a hard portion.

40. The position control apparatus of claim 28, wherein the working devices include a camera, a light source, an ultrasonic wave probe, a robot arm, a position control apparatus, a surgical apparatus, or a surgical auxiliary apparatus.

41. The position control apparatus of claim 28, wherein the position control apparatus additionally includes a driving device that enables an operation of the transfer unit or the moving system.

42. A trans-platform apparatus (300) comprising:
  (a) a cylindrical main platform (310) for insertion into a working space, wherein electrical connection terminals (340) are formed on an outer peripheral surface of the main platform;
  (b) a cylindrical working device (320) mounted on the outer peripheral surface of the main platform, wherein electrical connection terminals (340) are formed on a contact surface of the working device, which is in contact with the outer peripheral surface of the main platform; and
  (c) a positioner that (i) performs vertical motion and rotational motion, (ii) controls the position of the working device, and (iii) comprises a spin shaft and a connection wedge.

43. The trans-platform apparatus of claim 42, wherein the trans-platform apparatus additionally comprises (i) a spin shaft (330) that is formed on one side of the main platform or the working device, adjusts rotational and linear motion of the working device, and operates as a linkage axis of the working device, or (ii) a linear motion unit or linear motion guiding unit that enables linear motion of the working device in a horizontal direction of a central axis of the main platform.

44. The trans-platform apparatus of claim 42, wherein the electrical connection terminals (340) is formed in (i) an "L" shape, (ii), a dot shape, (iii) a rectangular shape, or (iv) a combination of the shapes.

45. The trans-platform apparatus of claim 42, wherein the entirety or a part of the outer peripheral surface of the main platform is subjected to water repellent coating.

46. The trans-platform apparatus of claim 42, wherein, in the trans-platform apparatus, a vicinity of the electrical connection terminals (340) formed on the outer peripheral surface of the main platform is subjected to water repellent coating.

47. The trans-platform apparatus of claim 45, wherein the outer peripheral surface of the main platform is subjected to water repellent coating by fluorine resin, silicone, gelatin, or rubber.

* * * * *